US012338443B2

(12) United States Patent
Imayoshi et al.

(10) Patent No.: US 12,338,443 B2
(45) Date of Patent: Jun. 24, 2025

(54) PHOTOACTIVATABLE TET EXPRESSION CONTROL SYSTEM

(71) Applicant: JAPAN SCIENCE AND TECHNOLOGY AGENCY, Saitama (JP)

(72) Inventors: Itaru Imayoshi, Kyoto (JP); Mayumi Yamada, Kyoto (JP); Yusuke Suzuki, Kyoto (JP); Shinji Nagasaki, Kyoto (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 1099 days.

(21) Appl. No.: 17/271,037

(22) PCT Filed: Aug. 30, 2019

(86) PCT No.: PCT/JP2019/034217
§ 371 (c)(1),
(2) Date: Feb. 24, 2021

(87) PCT Pub. No.: WO2020/045651
PCT Pub. Date: Mar. 5, 2020

(65) Prior Publication Data

US 2021/0340548 A1 Nov. 4, 2021

(30) Foreign Application Priority Data

Aug. 31, 2018 (JP) ................................ 2018-163617

(51) Int. Cl.
*C12N 15/62* (2006.01)
*C07K 14/47* (2006.01)
*C12N 15/63* (2006.01)

(52) U.S. Cl.
CPC .......... *C12N 15/62* (2013.01); *C07K 14/4702* (2013.01); *C12N 15/63* (2013.01)

(58) Field of Classification Search
CPC ........ C12N 15/62; C12N 15/63; C12N 15/66; C12N 15/635; C07K 14/4702
See application file for complete search history.

(56) References Cited

U.S. PATENT DOCUMENTS

2015/0291966 A1* 10/2015 Zhang .................... C12N 15/63
2018/0245097 A1* 8/2018 Vogel .................. C12Q 1/6897

FOREIGN PATENT DOCUMENTS

WO 2015/041219 A1 3/2015

OTHER PUBLICATIONS

Urlinger, S. et al. "The p65 domain from NF-kB is an efficient human activator in the tetracycline-regulatable gene expression system." Gene, vol. 247 (Feb. 21, 2000), pp. 103-110) (Year: 2000).*

Konermann, S. et al. "Optical control of mammalian endogenous transcription and epigenetic states." Nature, vol. 500, No. 7463 (2013), pp. 472-476. (Year: 2013).*

Scholz, O. et al. "Activity reversal of Tet repressor caused by single amino acid exchanges". Molecular Microbiology, vol. 53, No. 3 (2004), pp. 777-789 (Year: 2004).*

Henßler, E-M. et al. "Tet repressor mutants with altered effector binding and allostery". The FEBS Journal, vol. 272 (2005), pp. 4487-4496 (Year: 2005).*

Chan, Y-B. et al. "Optogenetic control of gene expression in *Drosophila*". PLOS One, vol. 10, No. 9 (2015), p. e0138181. (Year: 2015).*

Kaberniuk, A.A. et al. "A bacterial phytochrome-based optogenetic system controllable with near-infrared light" Nature Methods, vol. 13, No. 7 (Jul. 2016), pp. 591-597. (Year: 2016).*

Spangler, S.M. et al. "Optogenetic approaches for dissecting neuromodulation and GPCR signaling in neural circuits". Current Opinion in Pharmacology, vol. 32 (2017), pp. 56-70. (Year: 2017).*

Mansouri, M. et al. "Light-controlled mammalian cells and their therapeutic applications in Synthetic Biology". Advanced Science, vol. 6 (2019), p. 1800952. (Year: 2019).*

Hughes, R. "A compendium of chemical and genetic approaches to light-regulated gene transcription". Critical Reviews in Biochemistry and Molecular Biology, vol. 53, No. 5 (Jul. 2018), pp. 453-474. (Year: 2018).*

Japan Patent Office, "International Search Report for PCT Application No. PCT/JP2019/034217", Japan, Dec. 3, 2019.

Das, Atze T. et al., "Tet-On Systems for Doxycycline-inducible Gene Expression", Current Gene Therapy, 2016, 16, pp. 156-167.

Imayoshi, Itaru et al., "Oscillatory Control of Factors Determining Multipotency and Fate in Mouse Neural Progenitors", Science, vol. 342, 2013, pp. 1203-1208.

Imayoshi, Itaru et al., "bHLH Factors in Self-Renewal, Multipotency, and Fate Choice of Neural Progenitor Cells", Neuron 82, 2014, pp. 9-23.

(Continued)

*Primary Examiner* — Neil P Hammell
*Assistant Examiner* — Alexandra Geraldine Dace Denito
(74) *Attorney, Agent, or Firm* — Troutman Pepper Locke LLP; Tim Tingkang Xia, Esq.

(57) ABSTRACT

The present invention provides a photoactivatable Tet-OFF/ON system that can precisely control temporal and spatial gene expression. The present invention is a PA-Tet-OFF/ON system that includes a target gene expression cassette including a TRE having a TetO sequence, a promoter which is controlled by the TRE, and a target gene whose expression is controlled by the promoter; a first fusion protein expression cassette containing a gene which encodes a first fusion protein containing TetR or rTetR and a first protein; and a second fusion protein expression cassette containing a gene which encodes a second fusion protein containing p65AD and a second protein, in which the first protein and the second protein bind to each other to form a heterodimer only in a state of being irradiated with light at a specific wavelength.

12 Claims, 16 Drawing Sheets

Specification includes a Sequence Listing.

(56) References Cited

OTHER PUBLICATIONS

Duan, Liting et al., "Understanding CRY2 interactions for optical control of intracellular signaling", Nature Communications, 8: 547, 2017.
Jeong Rae-Dong et al., "Cryptochrome 2 and phototropin 2 regulate resistance proteinmediated viral defense by negatively regulating an E3 ubiquitin ligase", PNAS, Jul. 27, 2010, vol. 107, No. 30, 13538-13543.
Keller, Mercedes M. et al., "Cryptochrome 1 and phytochrome B control shadeavoidance responses in *Arabidopsis* via partially independent hormonal cascades", The Plant Journal (2011) 67, 195-207.
Wu, Liang et al., "Cryptochrome 1 is Implicated in Promoting R Protein-Mediated Plant Resistance to Pseudomonas syringae in *Arabidopsis*", Molecular Plant, vol. 3, No. 3, pp. 539-548, 2010.
Yu, Xuhong et al., "The Cryptochrome Blue Light Receptors", The *Arabidopsis* Book, 2010, vol. 8, Article No. e0135.
Kennedy, Matthew J. et al., "Rapid blue-light-mediated induction of protein interactions in living cells, nature methods", vol. 7, No. 12, 2010, pp. 973-975.
Liu, Xu et al., "Optogenetic stimulation of a hippocampal engram activates fear memory recall", Nature, vol. 484, 2012, pp. 381-385.
Taslimi, Amir et al., "Optimized second-generation CRY2-CIB dimerizers and photoactivatable Cre recombinase", Nature Chemical Biology, vol. 12, 2016, pp. 425-430.
Szulc, Jolanta et al., "A versatile tool for conditional gene expression and knockdown", Nature Methods, vol. 3, No. 2, 2006, pp. 109-116.
Wang, Xue et al., "Spatiotemporal control of gene expression by a light-switchable transgene system", Nature Methods, vol. 9, No. 3, 2012, pp. 266-269.
Hallett, Ryan A. et al., "Correlating in Vitro and in Vivo Activities of Light-Inducible Dimers: A Cellular Optogenetics Guide", ACS Synth. Biol. 2016, 5, pp. 53-64.
Mizushima, Seiichi et al., "pEF-BOS, a powerful mammalian expression vector", Nucleic Acids Research, vol. 18, No. 17, 1990, p. 5322.
Masamizu, Yoshito et al., "Real-time imaging of the somite segmentation clock: Revelation of unstable oscillators in the individual presomitic mesoderm cells", PNAS, 2006, vol. 103, No. 5, pp. 1313-1318.
Miyoshi, Hiroyuki, "Chapter 28 Gene Delivery to Hematopoietic Stem Cells Using Lentiviral Vectors, Gene Delivery to Mammalian Cells, vol. 2: Viral Gene Transfer Techniques", Methods in Molecular Biology, 2004, vol. 246, pp. 429-438.
Kawashima, Takashi et al., "Functional labeling of neurons and their projections using the synthetic activity-dependent promoter E-SARE", Nature Methods, vol. 10, No. 9, 2013, pp. 889-895.
Pédelacq, Jean-Denis et al., "Engineering and characterization of a superfolder green fluorescent protein", Nature Biotechnology, vol. 24, No. 1, Jan. 2006, pp. 79-88.
Nonaka, Mio et al., "Region-Specific Activation of CRTC1-CREB Signaling Mediates Long-Term Fear Memory", Neuron 84, 2014, pp. 92-106.
Okuno, Hiroyuki et al., "Inverse Synaptic Tagging of Inactive Synapses via Dynamic Interaction of Arc/Arg3.1 with CaMKIIβ", Cell, 149, 886-898, 2012.
Isomura, Akihiro et al., "Optogenetic perturbation and bioluminescence imaging to analyze cell-to-cell transfer of oscillatory information", Genes & Development, 31:524-535.
Hand, Randal et al., "Phosphorylation of Neurogenin2 Specifies the Migration Properties and the Dendritic Morphology of Pyramidal Neurons in the Neocortex", Neuron, vol. 48, 45-62.
Peters, Andrew J. et al., "Emergence of reproducible spatiotemporal activity during motor learning", Nature, vol. 510, 2014, pp. 263-267.
Pathak, Gopal P. et al., "Benchmarking of Optical Dimerizer Systems", ACS Synth. Biol. 2014, 3, pp. 832-838.
Sano, Hiromi et al., "Striatal Medium Spiny Neurons Terminate in a Distinct Region in the Lateral Hypothalamic Area and Do Not Directly Innervate Orexin/Hypocretin- or Melanin-Concentrating Hormone-Containing Neurons", The Journal of Neuroscience, 2007, 27(26):6948-6955.
Kabernuik, Andrii A et al., "A bacterial phytochrome-based optogenetic system controllable with near-infrared light", Nature Methods, vol. 13, No. 7, Jul. 2016, pp. 591-597.
Redchuk, Taras A et al., "Near-infrared optogenetic pair for protein regulation and spectral multiplexing", Nat Chem Biol, 2017, 13(6): 633-639.
Redchuk, Taras A et al., "Near-infrared light controlled systems for gene transcription regulation, protein targeting and spectral multiplexing", Nat Protoc, 2018, 13(5): 1121-1136.
Müller, Konrad et al., "An Optogenetic Upgrade for the Tet-OFF System", Biotechnology and Bioengineering, Jul. 2015, vol. 112, No. 7, pp. 1483-1487.
Konermann, Silvana et al., "Optical control of mammalian endogenous transcription and epigenetic states", Nature, Aug. 2013, 500 (7463), pp. 472-476.
Imayoshi, Itaru et al., "Latest technologies and models for studying the brain development and reorganization structure, 4. Light control technology of gene expression and application to neural stem cell research", Aug. 2018, vol. 36, No. 12, pp. 2127-2132.
Yamada, Mayumi et al., "Light Control of the Tet Gene Expression System in Mammalian Cells", Cell Reports, Oct. 2018, vol. 25, No. 2, pp. 487-500.

* cited by examiner

PHOTOACTIVATABLE TET EXPRESSION CONTROL SYSTEM

CROSS-REFERENCE TO RELATED PATENT APPLICATION

This application claims priority to Japanese Patent Application No. 2018-163617, filed Aug. 31, 2018, the content of which is incorporated herein by reference.

TECHNICAL FIELD OF THE INVENTION

The present invention relates to a tetracycline gene expression control system capable of controlling the expression of target genes by both light irradiation and a tetracycline (Tet)-based compound.

BACKGROUND OF THE INVENTION

The Tet-OFF/ON system utilizes the interaction between a Tet response element (TRE) having a Tet operator (TetO) sequence and a Tet repressor (TetR), and regulates the expression of exogenous genes in target cells by treating the cells with Tet or doxycycline (Dox), which is a more stable Tet analog (for example, see Non-Patent Literature 1). In the Tet-OFF system, a fusion protein consisting of TetR and a transactivation domain binds to TRE in the absence of Dox, which activates the minimal promoter that controls the expression of downstream genes. In the Tet-ON system, a fusion protein consisting of reverse TetR (rTetR) and a transactivation domain binds to TRE in the presence of Dox, which activates the minimal promoter that controls the expression of downstream genes. The Tet-OFF/ON system is a chemically controlled system that is most commonly used in mammalian cells. However, because this system uses Dox, which is a small molecule, for expression control, it is difficult for this system to induce target gene expression in a limited time frame or in cells within a limited space. For example, it is known that dynamic gene expression in stem cells or progenitor cells plays a key role in the retention, growth, and differentiation of stem cells in the ontogeny and maintenance of tissue homeostasis. Furthermore, it is known that these phenomena are closely correlated with the function of clock genes that control circadian rhythms or ultradian rhythms. However, the Tet-OFF/ON system cannot be operated with excellent time resolution•spatial resolution required to study these phenomena. Therefore, this system is not suited for studies•experiments that require rapid activation or inactivation of target genes described above.

As a gene expression system that overcomes the technical limitations of the conventional chemically controlled gene expression systems and can take temporal•spatial control, a system capable of controlling gene expression (ON/OFF) by light irradiation, that is, a photoactivatable (PA) expression system has been developed. In the technique of controlling gene expression by light, simply by adjusting the area to be irradiated with light or adjusting irradiance, it is possible to easily induce the target gene expression only in cells within a certain space in a limited time frame. For example, there is a report regarding the analysis of the functional importance of dynamic change in gene expression in basic helix-loop-helix (bHLH) transcription by using a PA-Gal4/UAS system (Light-ON system) which uses GAVPO as a photoactivatable transcription factor (see Non-Patent Literature 2 and Non-Patent Literature 3). Because GAVPO has a high activation and deactivation reaction rate, by changing the light irradiation pattern, it is possible to artificially induce the Ascl1 gene expression in neural stem cells in various dynamic phases (for example, persistent expression or oscillatory expression).

Examples of protein modules having light-dependent interaction include a blue light-responsive heterodimer formation module derived from *Arabidopsis thaliana*. This module consists of a Cryptochrome 2 (Cry2) photoreceptor and cryptochrome-interacting basic helix-loop-helix 1 (CIB1), which is a protein specifically binding to the Cry2 photoreceptor (for example, Non-Patent Literatures 4 to 8). *Arabidopsis thaliana* Cry2 is a photolyase-like photoreceptor that regulates the development and growth of plants by regulating circadian rhythms. Cry2 has two domains, the N-terminal photolyase homology region (PHR) and the Cryptochrome C-terminal extension (CCE or CCT). PHR is a chromophore-binding domain that non-covalently binds to the chromophore flavin adenine dinucleotide (FAD). Cry2 can bind to the bHLH transcription factor CIB1 in a blue light-specific manner. The truncating variant of the Cry2 and CIB1 essential domain acts as a blue light-dependent heterodimer formation module. In addition, it has been revealed that some point mutations of Cry2 induce a faster or slower light cycle (Non-Patent Literature 9, Non-Patent Literature 10, and Non-Patent Literature 11).

Examples of the near-infrared light-responsive heterodimer formation module include a protein module consisting of BphP1, which is a phytochrome derived from the photosynthetic bacterium *Rhodopseudomonas palustris*, and PpsR2, which is a protein specifically binding to BphP1. (For example, Non-Patent Literature 27). In a case where BphP1 and PpsR2 are irradiated with near-infrared light at 740 to 780 nm, the proteins bind to each other and form a heterodimer. This heterodimer is formed by the absorption of near-infrared light by using Biliverdin (BV), which is an endogenous chromophore of eukaryotes including mammals. PpsR2 is a relatively large protein having many domains. Therefore, by reengineering the BphP1/PpsR2 system so that the N-terminal side and the C-terminal side are deleted, a BphP1/Q-PAS1 system was developed which uses a PpsR2 deletion variant (Q-PAS1) consisting only of a Q-linker and a downstream PAS1 domain of the Q-linker (for example, Non-Patent Literatures 28 and 29).

CITATION LIST

Non-Patent Literature 1: Das et al., Current gene therapy, 2016, vol. 16, p. 156-167.

Non-Patent Literature 2: Imayoshi et al., Science, 2013, vol. 342, p. 1203-1208.

Non-Patent Literature 3: Imayoshi and Kageyama, Neuron, 2014, vol. 82, p. 9-23.

Non-Patent Literature 4: Duan et al., Nature Communications, 2017, vol. 8, Article number: 547.

Non-Patent Literature 5: Jeong et al., Proceedings of the National Academy of Sciences of the United States of America, 2010, vol. 107 (30), p. 13538-13543.

Non-Patent Literature 6: Keller et al., The Plant Journal, 2011, vol. 67 (2), p. 195-207.

Non-Patent Literature 7: Wu and Yang, Molecular plant, 2010, vol. 3 (3), p. 539-548.

Non-Patent Literature 8: Yu et al., The *Arabidopsis* Book, 2010, vol. 8, Article number: e0135.

Non-Patent Literature 9: Kennedy et al., Nature Methods, 2010, vol. 7 (12), p. 973-975.

Non-Patent Literature 10: Liu et al., Nature, 2012, vol. 484, p. 381-385.

Non-Patent Literature 11: Taslimi et al., Nature chemical biology, 2016, vol. 12, p. 425-430.

Non-Patent Literature 12: Szulc et al., Nature Methods, 2006, vol. 3 (2), p. 109-116.

Non-Patent Literature 13: Wang et al., Nature Methods, 2012, vol. 9 (3), p. 266-269.

Non-Patent Literature 14: Hallett et al., ACS Synthetic Biology, 2016, vol. 5, p. 53-64.

Non-Patent Literature 15: Mizushima and Nagata, Nucleic Acids Research, 1990, vol. 18 (17), p. 5322.

Non-Patent Literature 16: Masamizu et al., Proceedings of the National Academy of Sciences of the United States of America, 2006, vol. 103 (5), p. 1313-1318.

Non-Patent Literature 17: Miyoshi, 'Chapter 28 Gene Delivery to Hematopoietic Stem Cells Using Lentiviral Vectors', Methods in Molecular Biology, 2004, vol. 246 ("Gene Delivery to Mammalian Cells Volume 2: Viral Gene Transfer Techniques"), p. 429-438.

Non-Patent Literature 18: Kawashima et al, Nature Methods, 2013, vol. 10 (9), p. 889-895.

Non-Patent Literature 19: Pedelacq et al., Nature Biotechnology, 2006, vol. 24 (1), p. 79-88.

Non-Patent Literature 20: Nonaka et al., Neuron, 2014, vol. 84, p. 92-106.

Non-Patent Literature 21: Okuno et al., Cell, 2012, vol. 149, p. 886-898.

Non-Patent Literature 22: Isomura et al., Genes & Development, 2017, vol. 31, p. 524-535.

Non-Patent Literature 23: Hand et al., Neuron, 2005, vol. 48, p. 45-62.

Non-Patent Literature 24: Peters et al., Nature, 2014, vol. 510, p. 263-267.

Non-Patent Literature 25: Pathak et al., ACS Synthetic Biology, 2014, vol. 3, p. 832-838.

Non-Patent Literature 26: Sano and Yokoi, Journal of Neuroscience, 2007, vol. 27 (26), p. 6948-6955.

Non-Patent Literature 27: Kaberniuk et al., NATURE METHODS, 2016, vol. 13, p. 591-597.

Non-Patent Literature 28: Redchuk, et al., Nature Chemical Biology, 2017, vol. 13, p. 633-639.

Non-Patent Literature 29: Redchuk, et al., Nature Protocols, 2018, vol. 13 (5), p. 1121-1136.

SUMMARY OF THE INVENTION

Technical Problem

An object of the present invention is to provide a photoactivatable Tet-OFF/ON system that can precisely control temporal and spatial gene expression.

Solution to Problem

As a result of intensive studies, the inventors of the present invention have found that by incorporating a photoactivatable binding switch consisting of Cry2/CIB1 (hereinafter, called "Cry2/CIB1-PA binding switch" in some cases) or a photoactivatable binding switch consisting of BphP1/Q-PAS1 (hereinafter, called "BphP1/Q-PAS1-PA binding switch" in some cases) into a Tet-OFF/ON system, it is possible to obtain a system (hereinafter, called "PA-Tet-OFF/ON system" in some cases) that can control the expression of target genes by both light irradiation and a Tet-based compound. Based on this finding, the inventors have accomplished the present invention.

That is, a PA-Tet-OFF/ON system and the like according to the present invention are the following [1] to [27].

[1] A photoactivatable tetracycline gene expression control system, including a target gene expression cassette including a tetracycline response element having a TetO sequence, a promoter which is positioned downstream of the tetracycline response element and controlled by the tetracycline response element, and a target gene which is positioned downstream of the promoter and of which expression is controlled by the promoter, a first fusion protein expression cassette including a gene which encodes a first fusion protein containing a Tet repressor protein or a reverse Tet repressor protein and a first protein, and a second fusion protein expression cassette including a gene which encodes a second fusion protein containing a transactivation domain of a transactivation element p65 and a second protein, in which the first protein and the second protein bind to each other and form a heterodimer only in a state of being irradiated with light at a specific wavelength.

[2] The PA-Tet-OFF/ON system described in [1], in which the TetR or the rTetR has a threonine residue as an amino acid residue corresponding to the 194th isoleucine of wild-type TetR of *Escherichia coli.*

[3] The photoactivatable tetracycline gene expression control system described in [1] or [2], in which the Tet repressor protein or the reverse Tet repressor protein has a threonine residue as an amino acid residue corresponding to the 194th isoleucine of a wild-type Tet repressor protein of *Escherichia coli.*

[4] The photoactivatable tetracycline gene expression control system described in any one of [1] to [3], in which the first protein is CIB1 or a variant thereof and the second protein is Cry2 or a variant thereof, or the first protein is Cry2 or a variant thereof and the second protein is CIB1 or a variant thereof.

[5] The PA-Tet-OFF/ON system described in [4], in which the first protein is CIB1 or a variant thereof, and the second protein is Cry2 or a variant thereof.

[6] The PA-Tet-OFF/ON system described in [5], in which in the first fusion protein, CIB1 or a variant thereof is linked to a C-terminal side of the Tet repressor protein or the reverse Tet repressor protein.

[7] The PA-Tet-OFF/ON system described in [5] or [6], in which CIB1 or a variant thereof contained in the first fusion protein is a C-terminal deletion variant of CIB1 that consists of a partial protein corresponding to a region consisting of the 1st to 170th amino acids of wild-type CIB1 of *Arabidopsis thaliana*, or a variant that is obtained by deleting a nuclear localization signal from the C-terminal deletion variant of CIB1.

[8] The photoactivatable tetracycline gene expression control system described in [7], in which CIB1 or a variant thereof contained in the first fusion protein is a variant obtained by deleting a nuclear localization signal from a C-terminal deletion variant of CIB1 consisting of a partial protein corresponding to a region consisting of the 1st to 170th amino acids of wild-type CIB1 of *Arabidopsis thaliana*, and the second fusion protein contains a nuclear localization signal on the N-terminal or the C-terminal.

[9] The PA-Tet-OFF/ON system described in any one of [5] to [8], in which Cry2 or a variant thereof contained in the second fusion protein is a C-terminal deletion variant having an N-terminal photolyase homology region or a variant obtained by substituting an amino acid residue in the C-terminal deletion variant with phenylalanine, and the amino acid residue corresponds to the 348th leucine of wild-type Cry2 of *Arabidopsis thaliana.*

[10] The photoactivatable tetracycline gene expression control system described in any one of [1] to [3], in which the first protein is Bphp1 or a variant thereof and the second protein is Q-PAS1 or a variant thereof, or the first protein is Q-PAS1 or a variant thereof and the second protein is Bphp1 or a variant thereof.

[11] The photoactivatable tetracycline gene expression control system described in [10], in which the first protein is Bphp1 or a variant thereof, and the second protein is Q-PAS1 or a variant thereof.

[12] The photoactivatable tetracycline gene expression control system described in [11], in which the second fusion protein contains a nuclear localization signal on the N-terminal, and Q-PAS1 or a variant thereof is linked to the C-terminal side of the transactivation domain of the transactivation element p65.

[13] The photoactivatable tetracycline gene expression control system described in [11] or [12], in which in the first fusion protein, Bphp1 or a variant thereof is linked to the N-terminal side of the Tet repressor protein or the reverse Tet repressor protein, and in the second fusion protein, Q-PAS1 or a variant thereof is linked to the C-terminal side of the transactivation domain of the transactivation element p65.

[14] The PA-Tet-OFF/ON system described in any one of [1] to [13], further including, in addition to the target gene expression cassette: an expression cassette for a protein in which the first fusion protein and the second fusion protein are linked to each other through a T2A self-cleaving peptide; or an expression cassette for bicistronically expressing the first fusion protein and the second fusion protein.

[15] The PA-Tet-OFF/ON system described in any one of [1] to [14], in which the target gene is a gene that encodes a protein modified with ubiquitin.

[16] A cell including the PA-Tet-OFF/ON system described in any one of [1] to [15].

[17] A method for controlling target gene expression, including controlling expression of the target gene in the cell described in [16] by adjusting conditions so that the cell is irradiated or not irradiated with blue light or near-infrared light and treated or not treated with a Tet-based compound.

[18] A kit for a PA-Tet-OFF/ON system, including a target gene expression vector including TRE having a TetO sequence, a minimal promoter which is positioned downstream of the TRE and controlled by the TRE, and a multicloning site which is positioned downstream of the minimal promoter and into which a target gene will be inserted, a first expression vector including a first fusion protein expression cassette containing a gene that encodes a first fusion protein in which TetR or rTetR is linked to CIB1 or a variant thereof, and a second expression vector including a second fusion protein expression cassette containing a gene that encodes a second fusion protein in which a transactivation domain of a transactivation element p65 is linked to Cry2 or a variant thereof.

[19] A kit for a photoactivatable tetracycline gene expression control system, including a target gene expression vector including a tetracycline response element having a TetO sequence, a promoter which is positioned downstream of the tetracycline response element and controlled by the tetracycline response element, and a multicloning site which is positioned downstream of the promoter and into which a target gene will be inserted; a first expression vector including a first fusion protein expression cassette containing a gene that encodes a first fusion protein in which a Tet repressor protein or a reverse Tet repressor protein is linked to Bphp1 or a variant thereof, and a second expression vector including a second fusion protein expression cassette containing a gene that encodes a second fusion protein in which a transactivation domain of a transactivation element p65 is linked to Q-PAS1 or a variant thereof.

[20] The kit for a PA-Tet-OFF/ON system described in [18] or [19], including, instead of the first expression vector and the second expression vector, an expression vector including an expression cassette for a protein in which the first fusion protein and the second fusion protein are linked to each other through a T2A self-cleaving peptide, or an expression cassette for bicistronically expressing the first fusion protein and the second fusion protein.

[21] The kit for a PA-Tet-OFF/ON system described in [18] to [20], in which the TetR or rTetR has a threonine residue as an amino acid residue corresponding to the 194th isoleucine of wild-type TetR of *Escherichia coli.*

[22] An expression vector including an expression cassette for expressing a fusion protein in which TetR or rTetR is linked to CIB1 or a variant thereof.

[23] An expression vector including an expression cassette for expressing a fusion protein in which a transactivation domain of a transactivation element p65 is linked to Cry2 or a variant thereof.

[24] An expression vector including an expression cassette for expressing a fusion protein in which a Tet repressor protein or a reverse Tet repressor protein is linked to Bphp1 or a variant thereof.

[25] An expression vector including an expression cassette for expressing a fusion protein in which a transactivation domain of a transactivation element p65 is linked to Q-PAS1 or a variant thereof.

[26] An expression vector including an expression cassette for a protein in which a fusion protein, in which a Tet repressor protein or a reverse Tet repressor protein is linked to CIB1 or a variant thereof, and a fusion protein, in which a transactivation domain of a transactivation element p65 is linked to Cry2 or a variant thereof, are linked to each other through a T2A self-cleaving peptide, or an expression cassette for bicistronically expressing a fusion protein in which a Tet repressor protein or a reverse Tet repressor protein is linked to CIB1 or a variant thereof and a fusion protein in which a transactivation domain of a transactivation element p65 is linked to Cry2 or a variant thereof.

[27] An expression vector including an expression cassette for a protein in which a fusion protein, in which a Tet repressor protein or a reverse Tet repressor protein is linked to Bphp1 or a variant thereof, and a fusion protein, in which a transactivation domain of a transactivation element p65 is linked to Q-PAS1 or a variant thereof, are linked to each other through a T2A self-cleaving peptide, or an expression cassette for bicistronically expressing a fusion protein in which a Tet repressor protein or a reverse Tet repressor protein is linked to Bphp1 or a variant thereof and a fusion protein in which a transactivation domain of a transactivation element p65 is linked to Q-PAS1 or a variant thereof.

Advantageous Effects of the Invention

The PA-Tet-OFF/ON system according to the present invention is obtained by incorporating a Cry2/CIB1-PA binding switch or a BphP1/Q-PAS1-PA binding switch into the conventional Tet-OFF/ON system, and can control the expression of target genes not only by the treatment with a Tet-based compound that has been performed conventionally, but also by an irradiation treatment with blue light or near-infrared light. Therefore, this system can precisely control the temporal and spatial gene expression, and is useful as a tool for various biological experiments that require spatial expression control and rapid activity control.

Furthermore, in a case where the kit for a PA-Tet-OFF/ON system or the expression vector according to the present invention is used, it is possible to more conveniently control the target gene expression by operating the system.

BRIEF DESCRIPTION OF DRAWINGS

FIG. 10(A) is a view showing the blue light intensity dependence at each blue light intensity. FIG. 10(B) is a view showing the Dox concentration dependence at each Dox concentration. FIG. 10(C) is a matrix in which the blue light intensity is plotted on the Y-axis, the Dox concentration is plotted on the X-axis, and the transcriptional activity (luminescence signal intensity) is plotted on the Z-axis.

DESCRIPTION OF EMBODIMENTS OF THE INVENTION

Figure 1:
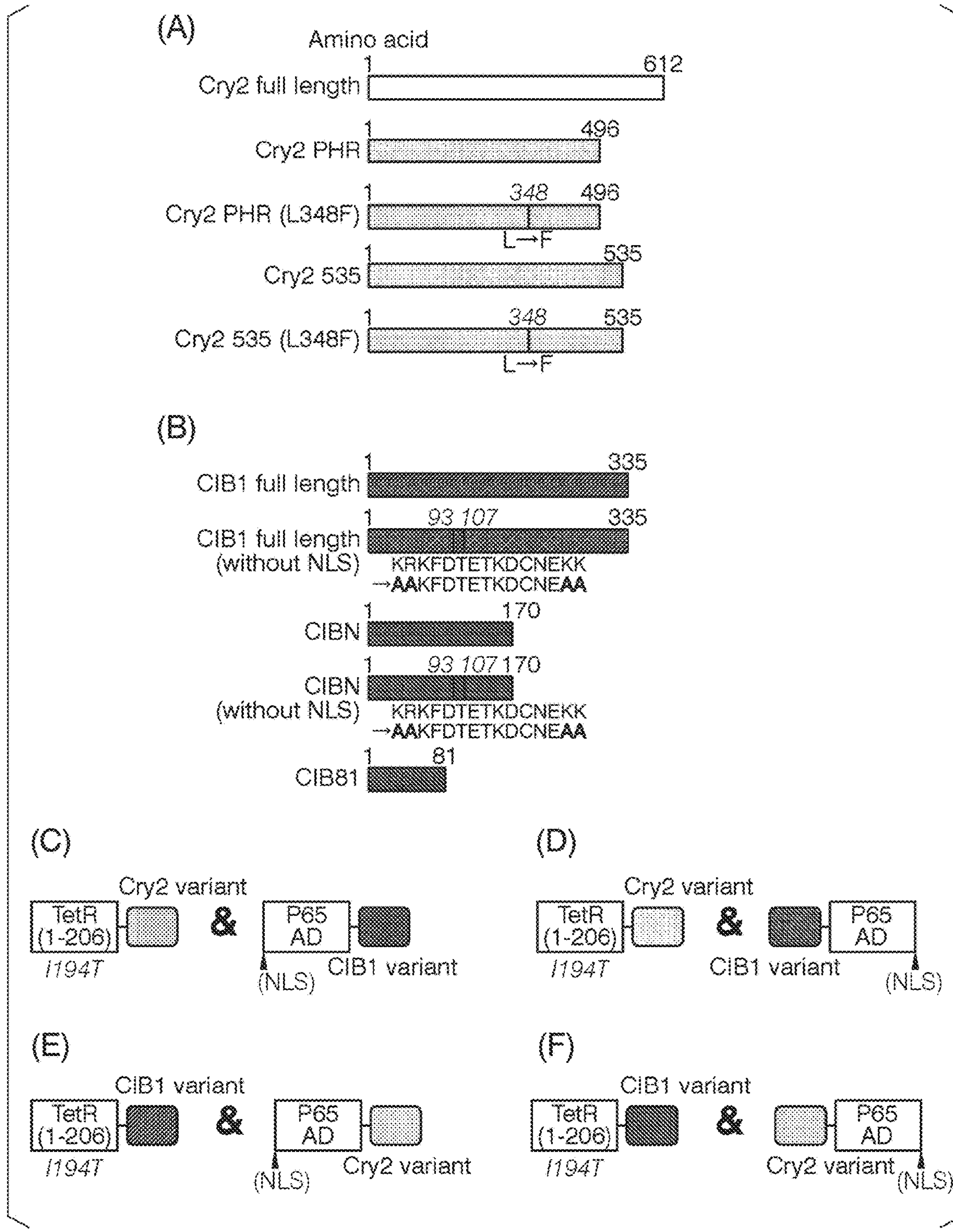
FIG. 1 is a view schematically showing PA-Tet-OFF candidate constructs used in Example 1.

Unlike in the conventional Tet-OFF/ON systems in which TetR (rTetR in the case of PA-Tet-ON system) and a transactivation domain are in the form of a fusion protein, in the PA-Tet-OFF/ON system according to the present invention, TetR and a transactivation domain are present as different molecules, and the complexation of these molecules is controlled using a photoresponsive binding switch. The photoresponsive binding switch is a module consisting of two kinds of proteins that bind to each other and form a heterodimer only in a state where the proteins are irradiated with light at a specific wavelength. In the present specification, one of the proteins forming a heterodimer is called first protein, and the other is called second protein. In the present invention, a fusion protein in which TetR is linked to one of the first protein and the second protein is called first fusion protein, and a fusion protein in which a transactivation domain is linked to the remaining other one is called second fusion protein. In a case where the first fusion protein and the second fusion protein are irradiated with light at a specific wavelength to cause the heterodimerization of the first protein and the second protein, the first fusion protein and the second fusion protein form a complex through the heterodimerization. As a result, a complex consisting of TetR and a transactivation domain is formed, and a target gene is expressed downstream of TRE in the absence of a Tet-based compound. In an environment where the proteins are not irradiated with light at a specific wavelength, the first protein and the second protein do not form a heterodimer, and the expression of a target gene is not induced. In this way, the PA-Tet-OFF/ON system according to the present invention can control the expression of a target gene by both light irradiation and a Tet-based compound by means of controlling the complexation of TetR and a transactivation domain by light irradiation.

For example, the PA-Tet-OFF/ON system according to the present invention is controlled using a Cry2/CIB1-PA binding switch. That is, one of the first protein and the second protein is Cry2 or a variant thereof, and the other is CIB1 or a variant thereof. The Cry2/CIB1-PA binding switch is a blue light-responsive heterodimer formation module derived from *Arabidopsis thaliana*. In a case where this module is irradiated with blue light, a complex consisting of a Cry2 dimer and a CIB1 dimer is formed. In the present invention, one of Cry2 and CIB1 is linked to TetR to form a fusion protein, and the remaining other one of Cry2 and CIB1 is linked to a transactivation domain to form a fusion protein. Therefore, for example, in the PA-Tet-OFF system, under the conditions where blue light irradiation is not carried out, TetR and a transactivation domain do not form a complex, and a target gene is not expressed downstream of TRE even in the absence of a Tet-based compound. In contrast, in a case where blue light irradiation is carried out, a Cry2/CIB1 heterodimer is formed. As a result, a complex of TetR and a transactivation domain is formed, and a target gene is expressed downstream of TRE in the absence of a Tet-based compound. Here, in the presence of a Tet-based compound, the complex of TetR and a transactivation domain cannot bind to TRE, and a target gene is not expressed.

For example, the PA-Tet-OFF/ON system according to the present invention is controlled using a BphP1/Q-PAS1-PA binding switch. That is, one of the first protein and the second protein is BphP1 or a variant thereof, and the other is Q-PAS1 or a variant thereof. The BphP1/Q-PAS1-PA binding switch is a near-infrared light-responsive heterodimer formation module derived from *Rhodopseudomonas palustris*. In a case where this module is irradiated with near-infrared light, a heterodimer consisting of BphP1 and Q-PAS1 is formed. In the present invention, one of BphP1 and Q-PAS1 is linked to TetR to form a fusion protein, and the remaining other one of BphP1 and Q-PAS1 is linked to a transactivation domain to form a fusion protein. Therefore, for example, in the PA-Tet-OFF system, under the conditions where near-infrared light irradiation is not carried out, TetR and a transactivation domain do not form a complex, and a target gene is not expressed downstream of TRE even in the absence of a Tet-based compound. In contrast, in a case where near-infrared light irradiation is carried out, a BphP1/Q-PAS1 heterodimer is formed. As a result, a complex of TetR and a transactivation domain is formed, and a target gene is expressed downstream of TRE in the absence of a Tet-based compound. Here, in the presence of a Tet-based compound, the complex of TetR and a transactivation domain cannot bind to TRE, and a target gene is not expressed.

Specifically, the PA-Tet-OFF/ON system according to the present invention includes a target gene expression cassette including TRE having a TetO sequence, a minimal promoter which is positioned downstream of TRE and controlled by the TRE, and a target gene which is positioned downstream of the minimal promoter and of which the expression is controlled by the minimal promoter, a first fusion protein expression cassette including a gene that encodes a first fusion protein containing TetR or rTetR, and a second fusion protein expression cassette including a gene that encodes a second fusion protein including a transactivation domain of a transactivation element p65 (region corresponding to residues 286 to 550 of human p65, hereinafter, represented by "p65AD"). In the present invention, p65AD is used as a transactivation domain. Therefore, the target gene expression is induced to a higher level in the present invention than in a system using a transactivation domain of VP16.

The first fusion protein contains TetR or rTetR and the first protein. That is, TetR or rTetR and the first protein are directly or indirectly linked to each other. In the first fusion protein, any of TetR, rTetR, or the first protein may be on the N-terminal side. The second fusion protein contains p65AD and the second protein. That is, p65AD and the second protein are directly or indirectly linked to each other. In the second fusion protein, any of p65AD or the second protein may be on the N-terminal side.

In a case where the PA-Tet-OFF/ON system according to the present invention uses the Cry2/CIB1-PA binding switch, and the first fusion protein containing TetR or rTetR is CIB1 or a variant thereof, the second fusion protein containing p65AD contains Cry2 or a variant thereof. In a case where the first fusion protein containing TetR or rTetR contains Cry2 or a variant thereof, the second fusion protein containing p65AD contains CIB1 or a variant thereof.

In a case where the PA-Tet-OFF/ON system according to the present invention uses the BphP1/Q-PAS1-PA binding switch, and the first fusion protein containing TetR or rTetR contains BphP1 or a variant thereof, the second fusion protein containing p65AD contains Q-PAS1 or a variant thereof. In a case where the first fusion protein containing TetR or rTetR contains Q-PAS1 or a variant thereof, the second fusion protein containing p65AD contains BphP1 or a variant thereof.

In the present invention and the present specification, a Tet-based compound is a compound having a function of binding to a complex consisting of TetR and p65AD just as Tet so as to inhibit the complex from binding to a TetO sequence. Furthermore, the compound also has a function of binding to a complex consisting of rTetR and p65AD so as to cause the complex to bind to a TetO sequence. The Tet-based compound includes Tet and analogs thereof. Examples of Tet analogs include Dox, anhydrotetracycline, cyanotetracycline, and the like.

TetR used in the present invention is a protein that binds to TRE in a state of not binding to Tet and does not bind to TRE in a state of binding to Tet. TetR is not particularly limited. For example, it is possible to use TetR appropriately selected from TetRs that can be used in the conventional Tet-OFF/ON system. Specifically, examples of usable TetR include TetR of Tet-resistant operons in Tet-resistant microorganisms or a variant thereof. It is preferable to use TetR of *Escherichia coli* or a variant thereof which has been very frequently used in the conventional Tet-OFF/ON system.

TetR used in the present invention may be the wild-type TetR of any Tet-resistant microorganisms existing in nature. However, as TetR, variant TetR is preferable which has a threonine residue as an amino acid residue corresponding to the 194th isoleucine in the wild-type TetR (tetracycline repressor protein class B from transposon Tn10) of *Escherichia coli* (hereinafter, called "TetR (I194T)" in some cases). In the conventional Tet-OFF/ON system, the TetR (I194T) expression efficiency induced by a Tet-based compound is substantially the same as the wild-type TetR expression efficiency. However, in the PA-Tet-OFF/ON system according to the present invention, PA-Tet-controlled expression efficiency of this variant is higher than the expression efficiency of the wild-type TetR. By substituting an amino acid residue which corresponds to the 194th isoleucine in the wild-type TetR of *Escherichia coli* in TetR used in the conventional Tet-OFF/ON system with a threonine residue, TetR suitable for the PA-Tet-OFF/ON system according to the present invention is obtained.

rTetR used in the present invention is a protein that binds to TRE in a state of binding to Tet and does not bind to TRE in a state of not binding to Tet. rTetR is obtained by introducing a reverse phenotype-inducing mutation into TetR. Examples of the reverse phenotype-inducing mutation include rtTA (E71K, D95N, L101S, and G102D), S2 (E19G, A56P, D148E, and H179R), M2 (S12G, E19G, A56P, D148E, and H179R), V10 (E19G, A56P, F67S, F86Y, D148E, R171K, and H179R), V16 (V9I, E19G, A56P, F67S, F86Y, D148E, R171K, and H179R) (Non-Patent Literature 1), and the like. These mutations are based on the amino acid sequence of wild-type TetR of *Escherichia coli*. As a mutation to be introduced into rTetR used in the present invention, M2, V10, or V16 is preferable, and V10 is more preferable, because such a mutation further increases the PA-Tet-controlled expression efficiency of a target gene.

The I194T mutation brings about the effect of improving the PA-Tet-controlled expression efficiency, not only in TetR but also in rTetR. Therefore, rTetR used in the present invention is preferably prepared by introducing I194T and reverse phenotype-inducing mutations into TetR, more preferably prepared by introducing I194T and M2, V10, or V16 mutations into TetR, and even more preferably prepared by introducing I194T and V10 mutations into TetR.

In the present invention and the present specification, a target gene is a gene whose expression is controlled by the PA-Tet-OFF/ON system. The target gene may be a natural gene of any of naturally occurring organisms or viruses, an artificially modified gene, or an artificially designed and synthesized gene. The method for artificially modifying a natural gene is not particularly limited. Examples thereof include a method of modifying a natural gene into a gene that encodes a protein obtained by the substitution, addition, or deletion of one or more amino acids in a protein encoded by the natural gene, a method of modifying a natural gene into a gene that encodes a fusion protein consisting of two or more proteins which are linked to each other directly or through an appropriate linker, and the like. These can be carried out by conventional methods using gene recombination techniques.

In the present invention and the present specification, a target gene may be a gene that encodes a fluorescent protein or a protein linked to an enzyme marker, such as luciferase or β-galactosidase, directly or through a T2A self-cleaving peptide, because it is easy to tell whether or not these genes are expressed. In addition, the target gene may be linked to a gene encoding a fluorescent protein or an enzyme marker by a bicistronic expression element such as an internal ribosomal entry site (IRES). Furthermore, in a case where a target protein to be expressed is modified with ubiquitin, and a gene encoding this protein is used as a target gene, it is possible to inhibit the long-term accumulation of the protein in cells and to strictly control the time for which the target gene is expressed.

In the present invention and the present specification, an expression cassette is DNA necessary for expressing a protein, and contains at least a gene that encodes the protein and a promoter that controls the expression of the gene. The promoter contained in various expression cassettes used in the present invention is not particularly limited as long as the promoter functions in an expression system (host expression system) to be transfected with the PA-Tet-OFF/ON system to express a target gene. The promoter may be a promoter intrinsic to cells derived from the host expression system, a promoter derived from cells of bio species other than the above cells, or an artificially synthesized promoter. Examples of promoters contained in various expression cassettes used in the present invention include promoters used in various expression vectors, such as the hCMV promoter, the SV40 promoter, the CAG promoter, and the EF1α promoter.

The expression cassette may further contain a terminator positioned downstream of the target gene to be expressed. Furthermore, one or more 5'-untranslated regions (UTR) or one or more 3'-UTRs may be contained in the expression cassette. In a case where the host expression system is a eukaryotic cell expression system, the expression cassette may have a polyadenylation sequence positioned downstream of the gene. The terminator, 5'-UTR, 3'-UTR, and the like to be incorporated into the expression cassette can be appropriately selected from those generally used in the field of protein expression using cells and the like.

The target gene expression cassette used in the present invention contains TRE, a minimal promoter positioned downstream of TRE, and a target gene for which the minimal promoter determines a transcription initiation site. The minimal promoter means a partial promoter that determines the transcription initiation site but is incapable of initiating transcription by itself. In a state where a complex consisting of TetR and a transactivation domain or a complex consisting of rTetR and a transactivation domain is not bound to TRE, the minimal promoter in the target gene expression cassette cannot induce the expression of the target gene. Only after being activated by TRE bound to a complex consisting of TetR and a transactivation domain or a complex consisting of rTetR and a transactivation domain, the minimal promoter can initiate the transcription of the target gene. The minimal promoter contained in the target gene expression cassette is not particularly limited. For example, it is possible to use a partial promoter of promoters, such as the hCMV promoter and SV40 promoter, which are widely used in expressing proteins.

The target gene expression cassette used in the present invention contains TRE which is positioned upstream of the minimal promoter and controls the transcriptional activity of the minimal promoter. TRE is not particularly limited as long as it has one or more TetO sequences. TRE may consist only of a TetO sequence or include a region in addition to a TetO sequence. In a case where TRE has a plurality of TetO sequences, the TetO sequences may be directly linked to each other in tandem or may be linked to each other through an appropriate DNA linker. Furthermore, the plurality of TetO sequences in TRE may all be the same TetO sequence, or may be different types of TetO sequences. For example, TRE used in the target gene expression cassette can be appropriately selected from TREs that can be used in the conventional Tet-OFF/ON system.

The TetO sequence may be a DNA sequence to which a complex consisting of TetR and p65AD formed via a Cry2/CIB1 heterodimer or a BphP1/Q-PAS1 heterodimer can bind in the absence of a Tet-based compound, or a DNA sequence to which a complex consisting of rTetR and p65AD formed via a Cry2/CIB1 heterodimer or a BphP1/Q-PAS1 heterodimer can bind in the presence of a Tet-based compound. In a case where the complex consisting of TetR and p65AD or the complex consisting of rTetR and p65AD binds to TRE through a TetO sequence, the minimal promoter positioned downstream of TRE is activated, and the target gene is expressed. The TetO sequence contained in the target gene expression cassette used in the present invention is not particularly limited. The TetO sequence to be used can be appropriately selected from known TetO sequences. Examples of the TetO sequence include a TetO sequence of Tet-resistant operons in Tet-resistant microorganisms or a variant thereof. It is preferable to use a TetO sequence of *Escherichia coli* or a variant thereof which has been very frequently used in the conventional Tet-OFF/ON system.

The first fusion protein expression cassette used in the present invention is an expression cassette for expressing a first fusion protein containing TetR or rTetR and a first protein. Furthermore, the second fusion protein expression cassette is an expression cassette for expressing a second fusion protein containing p65AD and a second protein.

In a case where the PA-Tet-OFF/ON system according to the present invention uses a Cry2/CIB1-PA binding switch, one of the first protein and the second protein is Cry2 or a variant thereof, and the other is CIB1 or a variant thereof. The first fusion protein expression cassette used in the present invention is an expression cassette for expressing a first fusion protein containing TetR or rTetR and CIB1 or a variant thereof or Cry2 or a variant thereof. The second fusion protein expression cassette is an expression cassette for expressing a second fusion protein containing p65AD and CIB1 or a variant thereof or Cry2 or a variant thereof. In a case where the first fusion protein is a fusion protein containing TetR or rTetR and CIB1 or a variant thereof, the second fusion protein is a fusion protein containing p65AD and Cry2 or a variant thereof. Conversely, in a case where the first fusion protein is a fusion protein containing TetR or rTetR and Cry2 or a variant thereof, the second fusion protein is a fusion protein containing p65AD and CIB1 or a variant thereof.

Examples of CIB1 used in the present invention include wild-type CIB1 (AtCIB1: full length of 335 amino acids) of *Arabidopsis thaliana* or a homologous protein thereof. Examples of the CIB1 variant used in the present invention include a C-terminal deletion variant and a nuclear localization signal (NLS) deletion variant of CIB1 described above. NLS is a region consisting of the 93rd to 107th amino acid residues in AtCIB1. The NLS deletion variant may be a variant prepared by the substitution of one or more amino acids in NLS or a variant prepared by the deletion of NLS. Examples of the C-terminal deletion variant of CIB1 include a C-terminal deletion variant consisting of a partial N-terminal protein corresponding to the region consisting of the 1st to 170th amino acids in AtCIB1 and a C-terminal deletion variant consisting of a partial N-terminal protein corresponding to the region consisting of the 1st to 81st amino acids in AtCIB1. Examples of CIB1 or a variant thereof used in the present invention include a full-length CIB1 protein, an NLS deletion variant of CIB1, a C-terminal deletion variant consisting of a partial N-terminal protein corresponding to a region consisting of the 1st to 170th amino acids in AtCIB1, a C-terminal deletion variant which consists of a partial N-terminal protein corresponding to a region consisting of the 1st to 170th amino acids in AtCIB1 and from which NLS has been deleted, and a C-terminal deletion variant consisting of a partial N-terminal protein corresponding to a region consisting of the 1st to 81st amino acids in AtCIB1. As CIB1 or a variant thereof used in the present invention, a C-terminal deletion variant of CIB1 consisting of a partial N-terminal protein corresponding to a region consisting of the 1st to 170th amino acids in AtCIB1 or a variant obtained by deleting NLS from the above C-terminal deletion variant is preferable, because these further increase the PA-Tet-controlled expression efficiency.

Examples of Cry2 used in the present invention include wild-type Cry2 of *Arabidopsis thaliana* (AtCry2: full length of 612 amino acids) or a homologous protein thereof. Examples of the Cry2 variant used in the present invention include a C-terminal deletion variant having N-terminal PHR of Cry2 and a variant obtained by substituting an amino acid residue which corresponds to the 348th leucine in AtCry2 in the C-terminal deletion variant with phenylalanine. Examples of the C-terminal deletion variant having N-terminal PHR of Cry2 include a C-terminal deletion variant of Cry2 consisting of a partial N-terminal protein corresponding to a region consisting of the 1st to 535th amino acids of AtCry2, a C-terminal deletion variant of Cry2 consisting of a partial N-terminal protein corresponding to a region consisting of the 1st to 496th amino acids of AtCry2, and the like. Cry2 or a variant thereof used in the present invention is preferably a C-terminal deletion variant of Cry2 consisting of a partial N-terminal protein corresponding to a region consisting of the 1st to 535th amino acids of AtCry2, a C-terminal deletion variant of Cry2 consisting of a partial N-terminal protein corresponding to a region consisting of the 1st to 496th amino acids of AtCry2, or a C-terminal deletion variant of Cry2 obtained by introducing a point mutation into a partial N-terminal protein corresponding to a region consisting of the 1st to 535th amino acids of AtCry2 so that an amino acid residue corresponding to the 348th leucine of AtCry2 is substituted with phenylalanine, because these genes further increase the PA-Tet-controlled expression efficiency.

The first fusion protein used in the present invention is a protein in which TetR or rTetR is linked to CIB1 or a variant thereof or to Cry2 or a variant thereof directly or through a peptide linker consisting of one or more amino acids. In the first fusion protein, CIB1 or the like may be linked to the C-terminal side or N-terminal side of TetR or rTetR. The length of the peptide linker is not particularly limited. For example, the peptide linker may consist of 1 to 25 amino acids.

The second fusion protein used in the present invention is a protein in which p65AD is linked to CIB1 or a variant thereof or to Cry2 or a variant thereof directly or through a peptide linker consisting of one or more amino acids. In the second fusion protein, CIB1 or the like may be linked to the C-terminal side or N-terminal side of p65AD.

The first fusion protein used in the present invention is preferably a protein in which CIB1 or a variant thereof is linked to the C-terminal side of TetR or rTetR directly or through a peptide linker consisting of one or more amino acids, more preferably a protein in which a C-terminal deletion variant of CIB1 consisting of a partial N-terminal protein corresponding to a region consisting of the 1st to 170th amino acids of AtCIB1 or a variant obtained by deleting NLS from the above C-terminal deletion variant is linked to the C-terminal side of TetR or rTetR directly or through a peptide linker consisting of one or more amino acids, and even more preferably a protein in which a C-terminal deletion variant of CIB1 consisting of a partial N-terminal protein corresponding to a region consisting of the 1st to 170th amino acids of AtCIB1 or a variant obtained by deleting NLS from the above C-terminal deletion variant is linked to the C-terminal side of TetR or rTetR through a peptide linker consisting of an amino acid sequence represented by SPKKK (SEQ ID NO: 13), because these proteins further increase the PA-Tet-controlled expression efficiency.

The second fusion protein used in the present invention is preferably a protein in which Cry2 or a variant thereof is linked to the N-terminal side or C-terminal side of p65AD directly or through a peptide linker consisting of one or more amino acids, more preferably a protein in which a C-terminal deletion variant having N-terminal PHR of Cry2 or a variant, which is obtained by introducing a point mutation into the above C-terminal deletion variant so that an amino acid residue corresponding to the 348th leucine of AtCry2 is substituted with phenylalanine, is linked to the N-terminal side or C-terminal side of p65AD directly or through a peptide linker consisting of one or more amino acids, even more preferably a protein in which a C-terminal deletion variant of Cry2 consisting of a partial N-terminal protein corresponding to a region consisting of the 1st to 535th amino acids of AtCry2, a C-terminal deletion variant of Cry2 consisting of a partial N-terminal protein corresponding to a region consisting of the 1st to 496th amino acids of AtCry2, or a C-terminal deletion variant of Cry2 which is obtained by introducing a point mutation into a partial N-terminal protein corresponding to a region consisting of the 1st to 535th amino acids of AtCry2 so that an amino acid residue corresponding to the 348th leucine of AtCry2 is substituted with phenylalanine, is linked to the N-terminal side or C-terminal side of p65AD directly or through a peptide linker consisting of one or more amino acids, still more preferably a protein in which a C-terminal deletion variant of Cry2 consisting of a partial N-terminal protein corresponding to a region consisting of the 1st to 535th amino acids of AtCry2 or a C-terminal deletion variant of Cry2 consisting of a partial N-terminal protein corresponding to a region consisting of the 1st to the 496th amino acids of AtCry2 is linked to the C-terminal side of p65AD directly or through a peptide linker consisting of one or more amino acids, or preferably a protein in which a C-terminal deletion variant of Cry2, which is obtained by introducing a point mutation into a partial N-terminal protein corresponding to a region consisting of the 1st to 535th amino acids of AtCry2 so that an amino acid residue corresponding to the 348th leucine of AtCry2 is substituted with phenylalanine, is linked to the N-terminal side of p65AD directly or through a peptide linker consisting of one or more amino acids, because these proteins further increase the PA-Tet-controlled expression efficiency.

In a case where the PA-Tet-OFF/ON system according to the present invention uses the BphP1/Q-PAS1-PA binding switch, one of the first protein and the second protein is BphP1 or a variant thereof, and the other is Q-PAS1 or a variant thereof. The first fusion protein expression cassette used in the present invention is an expression cassette for expressing a first fusion protein containing TetR or rTetR and BphP1 or a variant thereof or Q-PAS1 or a variant thereof. The second fusion protein expression cassette is an expression cassette for expressing a second fusion protein containing p65AD and BphP1 or a variant thereof or Q-PAS1 or a variant thereof. In a case where the first fusion protein is a fusion protein containing TetR or rTetR and BphP1 or a variant thereof, the second fusion protein is a fusion protein containing p65AD and Q-PAS1 or a variant thereof. Conversely, in a case where the first fusion protein is a fusion protein containing TetR or rTetR and Q-PAS1 or a variant thereof, the second fusion protein is a fusion protein containing p65AD and BphP1 or a variant thereof.

Examples of BphP1 used in the present invention include wild-type BphP1 of *Rhodopseudomonas palustris* (RpBphP1: SEQ ID NO: 21, Non-Patent Literature 27) or a homologous protein thereof. Examples of the BphP1 variant used in the present invention include a variant obtained by deleting a region which does not affect the heterodimerization of BphP1 and Q-PAS1 and a variant obtained by introducing a mutation into such a region. Examples of the mutation to be introduced include mutations that induce the substitution, insertion, or deletion of one or more amino acids.

Examples of Q-PAS1 used in the present invention include a region consisting of Q-linker and PAS1 of the wild-type PpsR2 of *Rhodopseudomonas palustris* (RpPpsR2: Non-Patent Literature 26). Specifically, examples thereof include a partial protein RpQ-PAS1 consisting of the 101st to 251st amino acid residues (SEQ ID NO: 22, Non-Patent Literatures 28 and 29) or a partial protein corresponding to a region consisting of Q-linker and PAS1 of a homologous protein of RpPpsR2.

The first fusion protein used in the present invention is a protein in which TetR or rTetR is linked to BphP1 or a variant thereof or to Q-PAS1 or a variant thereof directly or through a peptide linker consisting of one or more amino acids. In the first fusion protein, BphP1 or the like may be linked to the C-terminal side or N-terminal side of TetR or rTetR. The length of the peptide linker is not particularly limited. For example, the peptide linker may consist of 1 to 25 amino acids.

The second fusion protein used in the present invention is a protein in which p65AD is linked to BphP1 or a variant thereof or to Q-PAS1 or a variant thereof directly or through a peptide linker consisting of one or more amino acids. In the second fusion protein, BphP1 or the like may be linked to the C-terminal side or N-terminal side of p65AD.

The first fusion protein used in the present invention is preferably a protein in which BphP1 or a variant thereof is linked to the N-terminal side or C-terminal side of TetR or rTetR directly or through a peptide linker consisting of one or more amino acids, more preferably a protein in which BphP1 is linked to the N-terminal side of TetR or rTetR directly or through a peptide linker consisting of one or more amino acids, and even more preferably a protein in which RpBphP1 is linked to the N-terminal side of TetR or rTetR through a peptide linker consisting of an amino acid sequence represented by SPKKK, HMEF (SEQ ID NO: 23), TSTR (SEQ ID NO: 24), or SPKKKHMEF (SEQ ID NO: 25), because these proteins further increase the PA-Tet-controlled expression efficiency.

The second fusion protein used in the present invention is preferably a protein in which Q-PAS1 or a variant thereof is linked to the N-terminal side or C-terminal side of p65AD directly or through a peptide linker consisting of one or more amino acids, more preferably a protein in which Q-PAS1 is linked to the N-terminal side of p65AD directly or through a peptide linker consisting of one or more amino acids, even more preferably a protein in which RpQ-PAS1 is linked to the N-terminal side of p65AD directly or through a peptide linker consisting of one or more amino acids, and still more preferably a protein in which RpQ-PAS1 is linked to the N-terminal side of p65AD through a peptide linker consisting of an amino acid sequence represented by HMEF or TSTR, because these proteins further increase the PA-Tet-controlled expression efficiency.

Unless the effects of the present invention are impaired, other peptides or proteins may be added to the first fusion protein and the second fusion protein used in the present invention. For example, in a case where the first fusion protein is a protein in which a variant, which is obtained by deleting NLS from a partial N-terminal protein corresponding to a region consisting of the 1st to 170th amino acids of AtCIB1, is linked to the C-terminal side of TetR or rTetR directly or through a peptide linker consisting of one or more amino acids, the second fusion protein is preferably a protein having one or more NLS added to the N-terminal or C-terminal. Furthermore, in a case where the second fusion protein is a protein in which p65AD is linked to Q-PAS1 directly or through a peptide linker consisting of one or more amino acids, the second fusion protein is preferably a protein having one or more NLS added to the N-terminal or C-terminal and more preferably a protein having one or more NLS added to the N-terminal.

The PA-Tet-OFF/ON system according to the present invention may include an expression cassette for a protein in which the first fusion protein and the second fusion protein are linked to each other through a T2A self-cleaving peptide, instead of the first fusion protein expression cassette and the second fusion protein expression cassette. The second fusion protein may be linked to the downstream side of the first fusion protein through the T2A self-cleaving peptide, or the first fusion protein may be linked to the downstream side of the second fusion protein through the T2A self-cleaving peptide. In addition, the proteins described above can be used as both the first fusion protein and the second fusion protein to be linked to each other through the T2A self-cleaving peptide.

The PA-Tet-OFF/ON system according to the present invention may include an expression cassette for bicistronically expressing the first fusion protein and the second fusion protein, instead of the first fusion protein expression cassette and the second fusion protein expression cassette. The expression cassette for bicistronically expressing the first fusion protein and the second fusion protein can be manufactured by conventional methods such as a method of linking a region encoding the first fusion protein to a region encoding the second fusion protein by using a bicistronic expression element such as IRES. The region encoding the second fusion protein may be linked to the downstream side of the region encoding the first fusion protein through a bicistronic expression element, or the region encoding the first fusion protein may be linked to the downstream side of the region encoding the second fusion protein through a bicistronic expression element. The proteins described above can be used as both the first fusion protein and the second fusion protein to be bicistronically expressed.

For the expression system into which the PA-Tet-OFF/ON system according to the present invention is introduced, by adjusting conditions so that the expression system is irradiated or not irradiated with blue light or near-infrared light and treated or not treated with a Tet-based compound, it is possible to control the expression of a target gene in the expression system. For an expression system into which a PA-Tet-OFF system having the TetR-containing first fusion protein is introduced, by irradiating the expression system with blue light or near-infrared light in the absence of a Tet-based compound, it is possible to induce the expression of a target gene. Furthermore, by increasing the irradiance of the blue light or the near-infrared light to be radiated, it is possible to improve the expression efficiency of the target gene. For an expression system into which a PA-Tet-ON system having rTetR-containing first fusion protein is introduced, by adding a Tet-based compound to the expression system and irradiating the expression system with blue light or near-infrared light, it is possible to induce the expression of a target gene. Furthermore, by increasing the irradiance of the blue light or the near-infrared light to be radiated or increasing the concentration of the Tet-based compound, it is possible to improve the expression efficiency of the target gene.

The expression system into which the PA-Tet-OFF/ON system according to the present invention is to be introduced may be a cell or a cell-free system. In a case where a cell is used as the expression system, the cell may be a cultured cell, a cell in the living body of an animal, or a cell in a tissue collected from an animal. The PA-Tet-OFF/ON system according to the present invention is suitable for inducing expression in an animal cell or a cell-free expression system derived from an animal cell, and particularly suitable for inducing expression in a mammalian cell or a cell-free expression system derived from a mammalian cell.

The PA-Tet-OFF/ON system according to the present invention induces the expression of a target gene only in the region irradiated with blue light or near-infrared light. Therefore, for example, by appropriately adjusting the region to be irradiated with blue light or the like or adjusting the irradiation timing, the system can induce the expression of a target gene only in a limited space at the desired timing.

In a case where the PA-Tet-OFF/ON system according to the present invention uses the BphP1/Q-PAS1-PA binding switch, a heterodimer of BphP1 and Q-PAS1 is formed using By. As BV used in this case, it is possible to use endogenous BV of eukaryote. However, it is also preferable to introduce exogenous BV into a cell. In a case where the cell is rich in BV, it is possible to form a heterodimer with higher sensitivity to near-infrared light and to induce the expression of a target gene. The introduction of BV into a cell to be caused to express the target gene may be performed by directly introducing BV into the cell by microinjection or the like or may be performed by introducing a gene encoding a protein having a function of facilitating the biosynthesis of BV into the cell.

The method for introducing the PA-Tet-OFF/ON system according to the present invention into an expression system is not particularly limited. For example, by incorporating appropriate vectors into the respective expression cassettes and introducing these vectors into an expression system by a conventional method, it is possible to introduce the PA-Tet-OFF/ON system according to the present invention into the expression system. For example, an expression vector into which the target gene expression cassette is incorporated, an expression vector containing the first fusion protein expression cassette, and an expression vector containing the second fusion protein expression cassette are introduced into the expression system. In addition, an expression vector into which the target gene expression cassette is incorporated and an expression vector containing an expression cassette for a gene encoding a protein in which the first fusion protein and the second fusion protein are linked to each other through a T2A self-cleaving peptide may be introduced into the expression system. Alternatively, an expression vector into which the target gene expression cassette is incorporated and an expression vector containing an expression cassette for bicistronically expressing the first fusion protein and the second fusion protein may be introduced into the expression system.

In a case where the expression system is a cell-free expression system, the expression cassettes can be added to the expression system as they are. In a case where the expression system is an animal cell, vectors that are appropriately selected according to the type of the animal cell and incorporated with the respective expression cassettes by a gene recombination technique can be introduced into the target cell by a generally used method such as calcium phosphate transfection, lipofection, or electroporation. As the vectors, it is possible to use known vectors such as a plasmid vector, a retroviral vector, and an adeno-associated viral vector.

All or some of the expression cassettes constituting the PA-Tet-OFF/ON system according to the present invention may be incorporated into the chromosome of an animal cell. The incorporation of the expression cassettes into the chromosome can be performed by a conventional knock-in technique such as homologous recombination.

As a kit for constructing a PA-Tet-OFF/ON system for expressing a target gene, a kit is useful which is obtained by combining an expression vector containing a first fusion protein expression cassette and an expression vector containing a second fusion protein expression cassette with a target gene expression vector containing TRE, a minimal promoter which is positioned downstream of the TRE and controlled by the TRE, and a multicloning site which is positioned downstream of the minimal promoter and into which a target gene will be inserted. As the target gene expression vector, the same vector as the TRE-containing vector used in the conventional Tet-OFF/ON system can be used as it is.

In a case where the PA-Tet-OFF/ON system according to the present invention uses the Cry2/CIB1-PA binding switch, the expression vector having the first fusion protein expression cassette contained in the kit for a PA-Tet-OFF/ON system is preferably an expression vector having the first fusion protein expression cassette containing a gene encoding a first fusion protein in which TetR or rTetR is linked to CIB1 or a variant thereof, and the expression vector having the second fusion protein expression cassette is preferably an expression vector having the second fusion protein expression cassette containing a gene encoding the second fusion protein in which p65AD is linked to Cry2 or a variant thereof, because these expression vectors further increase the PA-Tet-controlled expression efficiency. Furthermore, a kit is also preferable which has, instead of the expression vector having the first fusion protein expression cassette and the expression vector having the second fusion protein expression cassette, an expression vector having an expression cassette for a protein in which a fusion protein consisting of TetR or rTetR linked to CIB1 or a variant thereof and a fusion protein consisting of p65AD linked to Cry2 or a variant thereof are linked to each other through a T2A self-cleaving peptide. In addition, a kit is also preferable which has, instead of the expression vector having the first fusion protein expression cassette and the expression vector having the second fusion protein expression cassette, an expression vector having an expression cassette for the bicistronic expression of a fusion protein consisting of TetR or rTetR linked to CIB1 or a variant thereof and a fusion protein consisting of p65AD linked to Cry2 or a variant thereof.

In a case where the PA-Tet-OFF/ON system according to the present invention uses the BphP1/Q-PAS1-PA binding switch, the expression vector having the first fusion protein expression cassette contained in the kit for a PA-Tet-OFF/ON system is preferably an expression vector having the first fusion protein expression cassette containing a gene encoding the first fusion protein consisting of TetR or rTetR linked to Bphp1 or a variant thereof, and the expression vector having the second fusion protein expression cassette is preferably an expression vector having the second fusion protein expression cassette containing a gene encoding a second fusion protein consisting of p65AD linked to Q-PAS1 or a variant thereof, because these expression vectors further increase the PA-Tet-controlled expression efficiency. Furthermore, a kit is also preferable which has, instead of the expression vector having the first fusion protein expression cassette and the expression vector having the second fusion protein expression cassette, an expression vector having an expression cassette for a protein in which a fusion protein consisting of TetR or rTetR linked to BphP1 or a variant thereof and a fusion protein consisting of p65AD linked to Q-PAS1 or a variant thereof are linked to each other through a T2A self-cleaving peptide. Moreover, a kit is also preferable which has, instead of the expression vector having the first fusion protein expression cassette and the expression vector having the second fusion protein expression cassette, an expression vector having an expression cassette for the bicistronic expression of a fusion protein consisting of TetR or rTetR linked to Bphp1 or a variant thereof and a fusion protein consisting of p65AD linked to Q-PAS1 or a variant thereof.

EXAMPLES

Next, the present invention will be more specifically described with reference to examples and the like, but the present invention is not limited to the examples.

<Construct>

The constructs used in the following experiments were prepared as below.

For functional screening of PA-Tet-OFF candidate constructs, a DNA binding domain, a dimerization domain, and a Tet binding domain (residues 1 to 206 of TetR, hereinafter, represented by "TetR (1-206)") of TetR (SEQ ID NO: 1) and p65AD (SEQ ID NO: 2) were amplified using pLVPT-tTR-KRAB (plasmid #11642, manufactured by Addgene) (Non-Patent Literature 12) and pEF-hGAVPO (Non-Patent Literatures 2 and 13), respectively. The nucleic acids having sequences optimized for the mammalian codons encoding Cry2 (SEQ ID NO: 3) variants (Cry2 PHR, Cry2 PHR (L348F), Cry2 535, and Cry2 535 (L348F)), CIB1 (SEQ ID NO: 4), and variants thereof (CIB1 without a nuclear localization sequence [NLS], CIBN, CIBN without NLS, and CIB81) were synthesized by FASMAC (Non-Patent Literatures 10, 11, and 14). In order to validate the sequences of flexible linkers, a sequence derived from tTA-Ad (pTet-OFF Advanced, manufactured by Clontech/Takara Bio Inc.) having an S2A point mutation was used. The amino acid sequence encoded by tTA-Ad (S2A, residues 1 to 206) was identical to the amino acid sequence of TetR (residues 1 to 206). By using these sequences, TetR (residues 1 to 206) or p65AD was fused with a Cry2 variant or a CIB1 variant. Furthermore, the sequences of other point mutations, NLS, T2A, or FLAG® (registered trademark) tags were introduced into or added thereto by a conventional overlap extension polymerase chain reaction (PCR), restriction enzyme digestion, and ligation. These constructs were cloned into an expression vector plasmid (pEF-BOS) containing a human elongation factor 1a promoter sequence and a polyadenylation sequence and a variant thereof (Non-Patent Literature 15). All of the prepared constructs were checked by DNA sequencing.

In order to generate PA-Tet-ON candidate constructs, TetR sequences having the following reverse phenotypic (variant) mutations were synthesized: rtTA (E71K, D95N, L101S, and G102D), S2 (E19G, A56P, D148E, and H179R), M2 (S12G, E19G, A56P, D148E, and H179R), V10 (E19G, A56P, F67S, F86Y, D148E, R171K, and H179R), V16 (V9I, E19G, A56P, F67S, F86Y, D148E, R171K, and H179R) (Non-Patent Literature 1). These sequences were then substituted with TetR sequences of PA-Tet-OFF plasmids. Reporter plasmids for PA-Tet-OFF/ON activity were prepared using Emerald luciferase (Eluc) derived from Pyrearinus termitilluminans (manufactured by TOYOBO CO., LTD.). In order to rapidly degrade Eluc so as to prevent the long-term accumulation of the reporters in cells, one copy of variant ubiquitin (G76V) was fused with the N-terminal of Eluc (Non-Patent Literature 16). The Ub-Eluc encoding sequence was inserted into a TREtight plasmid (manufactured by Clontech/Takara Bio Inc.) (pTREtight-Ub-ELuc reporter).

In constructing plasmids for lentiviral vectors, a PA-Tet construct encoding sequence was inserted into the multicloning site of a CSII-EF-MCS plasmid, a CSII-EF-MCS-IRES2-Bsd plasmid, a CSII-EF-MCS-IRES2-mCherryNLS plasmid, or CSII-CAG-MCS plasmid (Non-Patent Literatures 2 and 17). Bsd represents a blasticidin resistance gene. CSII-EF-MCS was digested with AgeI so that the elongation factor (EF) promoter was removed. Furthermore, in order to avoid the influence of long terminal repeat (LTR)-mediated transcription, a TRE3G sequence (manufactured by Clontech/Takara Bio Inc.) and the 3'-untranslated region (UTR) of the mouse Hes1 gene were cloned in the reverse direction. A sequence encoding Ub-NLS-luc2 (ubiquitinated and destabilized firefly luciferase with NLS) or luc2 was inserted next to the TRE3G sequence. Hereinafter, a vector into which the sequence encoding Ub-NLS-luc2 is inserted will be called TRE3G-Ub-NLS-luc2-Hes1 3'UTR lentiviral vector, and a vector into which the sequence encoding luc2 is inserted will be called TRE3G-luc2-Hes1 3'UTR lentiviral vector.

In a plasmid construct of an adeno-associated viral (AAV) vector, FLAG-TetR (I194T, residues 1 to 206)-CIBN (without NLS)-T2A-mCherryNLS construct or an N-terminal fusion construct of NLS-tagged Cry2 PHR (L348F)-p65 AD was inserted into a multicloning site of pAAV-CAG-ArchT-GFP (plasmid #29777, manufactured by Addgene) by removing the ArchT-GFP sequence by digestion with BamHI and EcoRI. In order to create an expression cassette flanked by inverted terminal repeats (ITR), a GFP reporter plasmid controlled by TRE was constructed by inserting a TRE3Gs sequence, cDNA of a destabilizing signal-containing sfGFP (Non-Patent Literature 19), and a poly(A) signal sequence into a pFBAAV vector (Non-Patent Literature 18) (pFBAAV-TRE3G-GFP-pest-SV40 pA).

Nucleic acids having sequences optimized for mammalian codons encoding RpBphP1 (Non-Patent Literature 27) and Q-PAS1 (Non-Patent Literatures 28 and 29) were synthesized by FASMAC. By using these nucleic acids, constructs fused with TetR (residues 1 to 206) and p65AD or various variants thereof were cloned into pEF-BOS and variants thereof. All of the prepared constructs were checked by DNA sequencing. Other viral vectors were also prepared in the same manner as described above.

<Cell Culture>

In the following experiments, unless otherwise specified, cell culture was carried out as follows.

HEK293T cells and Eph4 cells (ATCC [American Type Culture Collection]) were cultured in a Dulbecco's Modified Eagle's Medium (DMEM) (manufactured by NACALAI TESQUE, INC. or Gibco) supplemented with 10% fetal bovine serum (FBS) (Hyclone, manufactured by Thermo Fisher Scientific Inc.), 100 units/mL penicillin, and 100 mg/mL streptomycin (manufactured by NACALAI TESQUE, INC.) at 37° C. in 5% $CO_2$. The HEK293T cells and the Eph4 cells were subcultured using 0.05% and 0.25% trypsin/EDTA (manufactured by NACALAI TESQUE, INC. or Gibco), respectively.

<Lentivirus Packaging>

In the following experiments, unless otherwise specified, lentivirus packaging was carried out as follows.

By using the methods described in Non-Patent Literature 2, Non-Patent Literature 17, and the like, lentiviral particles were produced from HEK293T cells transfected with packaging plasmids by calcium phosphate co-transfection or lipofection. The supernatant was started to be collected 24 hours after transfection and continuously collected for up to 36 hours. The supernatant was centrifuged at 6,000 g for 16 hours and concentrated. The obtained virus pellets were resuspended in phosphate-buffered saline (PBS) or physiological saline at a volume 1/100 to 1/500 of the initial volume, and the viral aliquots were frozen. The viral titer was about $10^8$ to $10^9$ IU (infectious units)/mL. The cultured cells were infected with the purified lentiviral particles at MOI (multiplicity of infection) of 10 to 20. The transduced cells were selected by Blasticidin S (2 μg/mL, manufactured by Invitrogen) for the lentiviral vector co-expressing Bsd and by fluorescence-activated cell sorting for the lentiviral vector co-expressing mCherry.

<Light Source>

In the following experiments, unless otherwise specified, the following sources were used as light sources.

An LED light source (LEDB-SBOXH, manufactured by OPTOCODE CORPORATION) was used to irradiate the cultured cells with blue light in a $CO_2$ incubator. In blue light illumination under a microscope (excluding the application of patterned light), blue light was produced by a pE-2 LED excitation system (CoolLED) with a 470 nm LAM. In order to irradiate brain nerve cells with blue light (465 nm), blue light was delivered by a penlight (Handy Blue Pro Plus, manufactured by RelyOn Ltd.) or PLEXBRIGHT® (manufactured by Plexon Inc).

<Application of Patterned Light>

A mosaic 3-pattern illuminator (Andor Instruments, manufactured by Belfast) equipped with a blue light-emitting diode (X-CITE® (registered trademark) 120 LED, manufactured by Excelitas Technologies) was attached to a microscope and used to supply light through an objective lens.

<Luciferase Assay>

In the following experiments, unless otherwise specified, the luciferase activity of lysed cells was assayed by using a luciferase assay system (manufactured by Promega Corporation) according to the manufacturer's protocol.

<Luciferase Activity Monitoring in Live Cells>

In the following experiments, unless otherwise specified, luciferase activity in live cells was monitored as follows.

Population-level luminescence signals were recorded by a live cell monitoring system (CL24B-LIC/B, manufactured by Churitsu Electric Corporation) equipped with a high-sensitivity photomultiplier tube (PMT) and an LED blue light source (LEDB-SBOXH, manufactured by OPTOCODE CORPORATION). Cells were seeded in a black 24-well plate containing 1 mM luciferin-containing medium, and photon counting was carried out.

<Estimation of Activation and Inactivation Reaction Rate of PA-Tet-Controlled Gene Expression>

The half-life of the switch-on/off reaction rate of PA-Tet-controlled gene expression in the PA-Tet-OFF system and the PA-Tet-ON system was determined through the following three steps.

First, in order to eliminate the linear trend of activity independent of photo stimulation, each waveform was determined. In the detrending process, linear regression was performed using data points less than the median absolute deviation of the waveform, and the values predicted by the regression were subtracted from all points in the waveform. Second, the event epoch induced by photo stimulation was estimated by comparing each value of the waveform with a stochastic threshold. At the stochastic threshold, random numbers with the same waveform vector length were generated from the Gaussian distribution. The stochastic threshold was generated by the same method in all assays. Each value of the waveform was compared with the threshold at the corresponding time point. This process was repeated 100 times, and the time point at which the probability that the gene expression level will exceed the threshold is higher than 50% was treated as an event (that is, PA-Tet-controlled gene expression). Finally, the period from the start to the peak of an event epoch was estimated as the value of τon, and the period from the peak to the end of the event epoch was estimated as the value of τoff. The half-life of the switch-on/off reaction rate of PA-Tet-controlled gene expression was calculated using the values of τon and τoff.

<Luciferase Imaging>

In the following experiments, unless otherwise specified, luciferase imaging was carried out as follows.

Cells were seeded in a 35-mm glass-based dish at 50% to 60% confluency, and incubated at 37° C. in 5% $CO_2$. Then, 1 mM luciferin was added to the medium. Bioluminescence images were obtained using an upright microscope (IX83, manufactured by Olympus Corporation) equipped with a 20× or 40× immersion objective lens. Digital images were obtained using a cooled CCD camera (iKon-M DU934P-BV, manufactured by Andor). Filters and cameras were automatically controlled using software (METAMORPH® (registered trademark), manufactured by Universal Imaging Corporation). Stray light was removed by turning off the electric system. The imaging system was used in a darkroom.

<Image Analysis and Quantification>

In the following experiments, unless otherwise specified, image analysis and quantification were carried out as follows.

Image analysis was performed using the ImageJ software and custom plug-ins (Non-Patent Literatures 2 and 22). Custom code for the ImageJ plug-in used in this experiment is available on request. In order to analyze bioluminescence imaging sequence files, "spike noise filter" was applied to the stack file so that the noise signals caused by cosmic rays were removed. CCD readout noise was also removed by "temporal background reduction filter". In this normalization procedure, the background intensity measured outside the imaging region of each time frame was subtracted from the signal intensity. Based on "circadian gene expression" (CGE), individual cells were tracked, and the bioluminescence signals were quantified. Nuclear localization mCherry was co-expressed and used to detect and track moving cells.

The average signal intensity in the nucleus was measured and analyzed with PRISM® (registered trademark) 5.0 software (manufactured by GraphPad Software.).

<Immunofluorescence Staining>

In the following experiments, unless otherwise specified, immunofluorescence staining was carried out as follows.

Cells or tissues were washed with PBS and immobilized with 4% paraformaldehyde/PBS for 20 minutes at room temperature. The immobilized cells were washed with PBS, blocked and permeabilized with 5% normal donkey serum (NDS) and 0.1% TRITON-X-100®/PBS for 20 minutes at room temperature, and incubated at 4° C. overnight together with primary antibodies diluted with PBS containing 1% NDS. The cells were then washed with PBS and incubated at room temperature for 1 hour together with conventional secondary antibodies bound to Alexa 405, Alexa 488, or Alexa 594 (manufactured by Invitrogen). The stained cells or tissues were imaged with an LSM510 or LSM780 confocal microscope (manufactured by ZEISS). The following antibodies were used as primary antibodies: mouse monoclonal anti-MAP2 antibody (M4403, manufactured by Sigma-Aldrich Co. LLC.), rabbit polyclonal anti-GFP antibody (A11122, manufactured by Thermo Fisher Scientific Inc.), and mouse monoclonal anti-NeuN antibody (MAB377, manufactured by Millipore Corporation).

<Evaluation of PA-Tet-OFF/ON Characteristics>

In the following experiments, unless otherwise specified, the characteristics of PA-Tet-OFF/ON were evaluated as follows.

(1) Functional Screening of PA-Tet-OFF Candidate Constructs

For functional screening of PA-Tet-OFF candidate constructs, HEK293T cells were seeded in a 24-well plate at 5 to $9\times10^4$ cells/well and cultured at 37° C. in 5% $CO_2$ for 24 hours. The cells were then transfected with LIPOFECTAMINE® (registered trademark) LTX (manufactured by Invitrogen) or polyethyleneimine (manufactured by Polysciences, Inc.) according to the manufacturer's protocol. Three plasmids, pEF-TetR (1-206) fused with the Cry2/CIB variant, pEF-p65AD fused with the Cry2/CIB variant, and the pTREtight-Ub-ELuc reporter, were subjected to co-transfection at 25:25:8 (mass ratio). The total amount of DNA was 0.58 μg/well. Forty-eight hours after transfection, the cells were exposed to blue light (7.2 W/$m^2$; pulsed for 2 seconds every minute) for 3 hours. Then, the cells were lysed, and the luciferase activity thereof was measured with a plate reader (ARVO X3, manufactured by PerkinElmer Inc.). Control cells were transfected with plasmids and then kept in a dark place. In order to analyze the constructs having the T2A sequence, expression vectors, pBS (pBluescript plasmids), and reporters were mixed together at 25:25:8 (mass ratio) and subjected to co-transfection. By using pBS, the total amount of DNA with which the cells will be transfected was adjusted.

Figure 8:
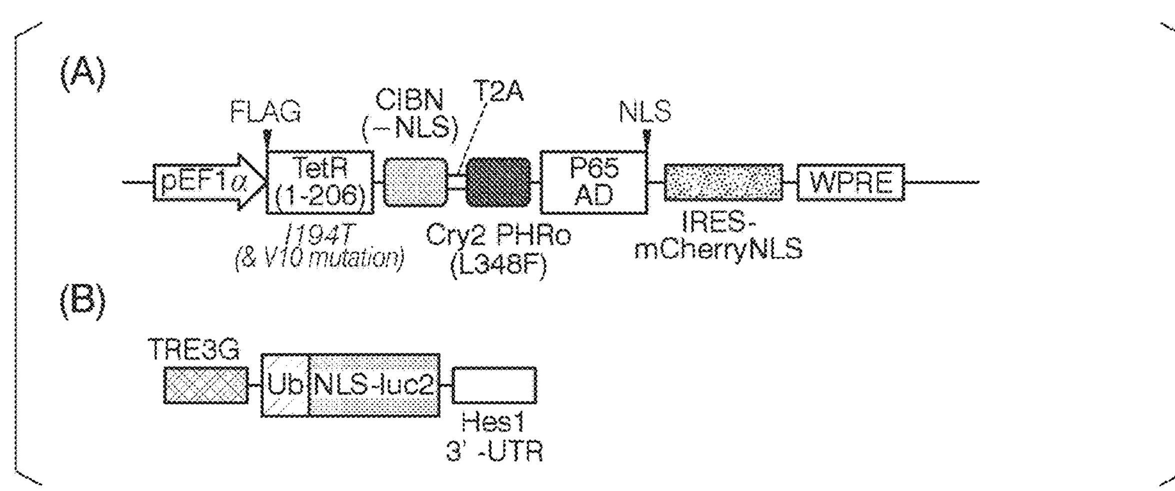
FIG. 8 is a schematic view showing an expression cassette for PA-Tet-OFF construct/PA-Tet-ON construct (A) and a Ub-NLS-luc2 expression cassette in a TRE3G-Ub-NLS-luc2-Hes1 3'UTR lentiviral vector (B) that were used for preparing a PA-Tet-OFF/ON system stable expression strain in Example 4.

(2) Analysis on Relationship Between Irradiance and Induced Gene Expression Level In order to analyze the relationship between irradiance and induced gene expression level, stable Eph4 cell clones transduced with PA-Tet-OFF and a TRE3G-Ub-NLS-luc2-Hes1 3'UTR lentiviral vector (FIG. 8(B)) were seeded in a 24-well plate at 5 to $9\times10^4$ cells/well, cultured for 24 hours, and assayed in the same manner as in the candidate construct screening. The cells were irradiated for 3 hours with blue light (7.2 W/$m^2$; pulsed for 2 seconds every minute) at irradiance of 0, 1.7, 3.5, 5.5, and 7.0 W/$m^2$.

(3) Analysis on Relationship Between Dox Concentration and Induced Gene Expression Level In order to analyze the relationship between the Dox concentration and the induced gene expression level, HEK293T cells were seeded in a 24-well plate at 5 to $9\times10^4$ cells/well, transfected, and assayed in the same manner as in candidate construct screening. Dox was applied to the cells at concentrations of 0, 1, 7.5, 15, 20, 50, and 100 ng/mL for the PA-Tet-OFF constructs and at concentrations of 0, 10, 15, 20, 30, 35, 40, 50, 75, 100, and 250 ng/mL for the PA-Tet-ON constructs. The cells were irradiated with blue light (7.2 W/$m^2$; pulsed for 2 seconds every minute) for 3 hours.

(4) Double-Controlled Analysis Using Light Intensity and Dox Concentration

In order to carry out double-controlled analysis using light intensity and Dox concentration, the stable cell clones transduced with PA-Tet-ON and the TRE3G-Ub-NLS-luc2-Hes1 3'UTR lentiviral vector were seeded in a 24-well plate at $1\times10^5$ cells/well and cultured for 24 hours. Dox was applied to the cells at concentrations of 0, 50, 75, 87.5, 92.5, 100, 250, and 500 ng/mL. The cells were irradiated with blue light (7.2 W/$m^2$; pulsed for 2 seconds every minute) for 3 hours at irradiance of 0, 1.8, 3.6, 5.9, and 7.1 W/$m^2$.

(5) Evaluation of Temporal Characteristics of PA-Tet-OFF/ON

In order to investigate the temporal characteristics of PA-Tet-OFF/ON, transfected HEK293T cells or lentivirus-transduced Eph4 cells were used. The cells were seeded in a black 24-well plate at $1\times10^4$ cells/well and exposed to blue light (7.2 W/$m^2$) for 1 to 2 minutes. Population-level luminescence signals were recorded using a live cell monitoring system (CL24B-LIC/B, manufactured by Churitsu Electric Corporation).

(6) Measurement of Ability of PA-Tet-OFF/ON System to Spatially Control Gene Expression In order to investigate the ability of the PA-Tet-OFF/ON system to spatially control gene expression in target cells, Eph4 cells transduced with lentivirus were seeded in a 35-mm glass-based dish (Cat #3910-035, manufactured by IWAKI & CO., LTD.) at 50% to 60% confluency. Before being irradiated with light, the cells were incubated at 37° C. in 5% $CO_2$ on a chamber stage of a microscope. Patterned light was generated by the MOSAIC 3 device and applied to the cells. The light (10 ms pulse) was applied to the cells 50 times to obtain luminescence signals changing over time. The power of the blue light source was set to 100%, and a 200×200 pixel area was observed through a 40× objective lens (UApo 40×Oil Iris3/340, manufactured by Olympus Corporation) (NA was changed to 0.55). As a result, light energy of 1.3 W/$m^2$ was measured.

<Statistical Analysis>

In the following experiments, unless otherwise specified, statistical analysis was carried out using PRISM® (registered trademark) 5.0 or 6.0 software (manufactured by GraphPad Software.). A P-value less than 0.05 was considered as significant <Primary Neuronal Culture>

In the following experiments, unless otherwise specified, primary neuronal culture was carried out as follows.

Hippocampal neurons were obtained from CA1/CA3/dentate gyrus of the hippocampus of 1-day-old (P1) mouse pups by a process devised by slightly modifying the methods described in Non-Patent Literature 20 and Non-Patent Literature 21. To finish the culture, the dissociated cells were seeded on a coverslip (Assistant, manufactured by Karl Hecht GmbH & Co KG.) coated with MATRIGEL® (manufactured by Invitrogen), and cultured on a minimum essential medium supplemented with 1 mM GLUTAMAX®

(trademark)-I, 25 μg/mL insulin, 2% GS21 neurotrophic supplement (manufactured by GlobalStem, Inc.), and 5% FBS (HYCLONE®, manufactured by Thermo Fisher Scientific Inc.). Twenty-four to forty-eight hours after seeding, 4 μM cytosine arabinoside (manufactured by Sigma-Aldrich Co. LLC.) was added to the medium so that the growth of glial cells was suppressed.

<Production of Recombinant AAV>

In the following experiments, unless otherwise specified, recombinant AAV was produced as follows.

Serotype DJ/8 AAV was produced in HEK293T cells co-transfected with an ITR-containing AAV vector, a packaging vector pAAV-DJ/8, and pHelper (manufactured by Cell Biolabs, Inc.). From the transfected cells, recombinant AAV particles were collected using an extraction kit (AAVpro extraction solution, manufactured by Takara Bio Inc.). The collected AAV particles were further purified using a discontinuous iodixanol gradient with ultracentrifugation (OPTIPREP®, manufactured by Alere Technologies AS) and concentrated in PBS by ultrafiltration. Viral titers of the purified AAV were measured by qPCR and adjusted to 2 to $10\times10^{12}$ genomic copies (gc/mL) per milliliter.

<Mouse Research>

All of the following animal experiments were approved by the Animal Care Committee of Kyoto University and met all relevant regulatory standards.

(1) Verification of PA-Tet-OFF/ON System in Neural Stem/Progenitor Cells of Developing Mouse Brain In order to verify the PA-Tet-OFF/ON system in neural stem/progenitor cells of developing mouse brain, pEF-mCherryNLS, pEF-PA-Tet-OFF, and the CSII-TRE3G-NLS-Ub-luc2-Hes1 3'UTR plasmid were mixed together at a ratio of 1:2:2 (mass ratio), and E14.5 dorsal telencephalic progenitor cells were co-transfected with these plasmids by ex utero electroporation (Non-Patent Literatures 2 and 23). In order to deliver the plasmid DNA (2.5 μg/μL) into the telencephalic ventricle by microinjection and to transfect the neural stem/progenitor cells on the surface of the neocortical ventricle with the plasmids, ex utero electroporation (6 pulses, 50 mV, square wave generator (CUY21, manufactured by BEX CO., LTD.), 5 mm paddle electrode) was performed. The brain was immediately dissected, embedded in 3% low-melting-point agarose by the method described in Non-Patent Literature 2 and Non-Patent Literature 23, cut into 250 μm organotypic slices by using a vibratome (VT1000, manufactured by LEICA), moved to a 12 mm well culture insert (Millicell, PICM01250, manufactured by Merck KGaA), and cultured in a slice culture medium. The slices were incubated at 37° C. and in 5% $CO_2$ while being periodically irradiated with blue light.

(2) Verification of PA-Tet-OFF/ON System in Adult Brain Neurons

In order to verify the PA-Tet-OFF/ON system in adult brain neurons, stereotaxic viral injection was performed on mice by using a sharp glass micropipette as described in Non-Patent Literature 18 and Non-Patent Literature 24. The mice (10 to 14 weeks old) were anesthetized with 440 mg/kg chloral hydrate (manufactured by Tokyo Chemical Industry Co., Ltd.) by intraperitoneal injection. Petrolatum was applied to both eyes to prevent dryness, and the scalp was treated with a depilatory cream. The mice were then immobilized on a small animal stereotaxic instrument (manufactured by David Kopf Instruments). The scalp was cut at the midline, and the periosteum was removed using a surgical knife. The skull was thinned with a drill, and mini-craniotomy was performed using a 27-gauge needle. The virus was injected through a pulled glass micropipette connected to a Hamilton syringe (Hamilton Company) pumped using a syringe pumping device (manufactured by World Precision Instruments). The stereotaxic injection was performed on the following tissue at appropriate coordinates: hippocampal dentate gyrus (A/P: −1.94 mm from bregma, M/L: ±1.3 mm from bregma, D/V: −1.82 mm from surface of pia mater). Two AAV vectors (AAV2-DJ/8 vector containing CAG-FLAG-TetR (I194T, 1-206)-CIBN (-NLS)-T2A-mCherryNLS construct and AAV2-DJ/8 vector containing CAG-NLS-attached Cry2 PHR (L348F)-p65 AD N-terminal fusion construct) were used for co-transfection at a ratio of 1:1 (titer ratio). The viral solution was injected at a volume of 0.5 to 1.5 μL at a rate of 0.1 μL/min. After the injection, the pipette was kept at the injection site for 10 more minutes before being removed. After the removal of the micropipette, the skin incision site was sutured, treated with an antibiotic cream, and a painkiller was injected subcutaneously to relieve postoperative pain. The animals having undergone injection were usually bred for 2 weeks before exposure to blue light. For AAV transduction into cortical neurons, custom headplates were adhered and fixed to the skull. A cranial incision (about 3.5 mm) was made over the visual cortex area. Three AAV vectors (AAV2-DJ/8 vector containing a CAG-FLAG-TetR (I194T, 1-206)-CIBN (-NLS)-T2A-mCherryNLS construct, AAV2-DJ/8 vector containing a CAG-NLS-attached Cry2 PHR (L348F)-p65 AD N-terminal fusion construct, and an AAV2-DJ/8 vector containing a TRE3G-luc2-Hes1 3'UTR construct) were used for co-transfection at a ratio of 1:1:1 (titer ratio).

(3) Photo Stimulation after AAV Transduction

Photo stimulation was started 14 days after the AAV transduction.

For irradiating the cortex with light, custom headplates and chronic cranial windows were implanted, and the mice were immobilized under blue penlights. The dorsal cortex was irradiated with blue light (100 $W/m^2$; pulsed for 3 minutes every 30 minutes) for 6 hours.

For irradiating the adult mouse hippocampus with light, by using a blue LED (PLEXBRIGHT®, manufactured by Plexon Inc) connected to an optical implant through a fiber patch cable and a rotary joint, freely moving awake mice were treated for 12 hours at an intensity of 85.6 $W/m^2$ in a duty cycle of 1.6% (pulsed for 1 second at 0.016 Hz). After being irradiated with blue light, the mice were immediately sacrificed and perfused. The incised brain was subjected to immunohistochemistry.

For irradiating the brains of mouse pups with light, anesthetized mice were stimulated through an optical fiber using a blue LED (PLEXBRIGHT®, manufactured by Plexon Inc). After being irradiated with blue light (40 $W/m^2$; pulsed for 1 second every 15 seconds; continued for 3 hours), the mice were immediately sacrificed, the right brain irradiated with blue light was immediately extracted and lysed, and the luciferase activity thereof was measured.

(4) Dox Treatment

The mice were treated with Dox. For long-term Dox administration, drinking water containing 1 mg/mL Dox in a 5% by mass sucrose solution was given to the mice. For Dox pulse treatment, the mice were given Dox by intraperitoneal injection at a single dose of 0.1 mg/g (body weight).

(5) Analysis in Subcutaneous Tissue

First, stable cell clones of Eph4 cells transduced with PA-Tet-OFF by using a lentiviral vector were transplanted into the subcutaneous tissue of the dorsal skin of adult mice. The stable cell clones were transplanted at 2 to $5\times10^6$ cells into the subcutaneous tissue by injection. Twenty-four hours after the injection of Eph4 cells, luciferin was additionally given to the mice at 200 mg/g (body weight) by intraperitoneal, subcutaneous, and intramuscular injection, and the mice were imaged using a CCD camera (iXon3, manufactured by ANDOR). The mice were anesthetized, then the transplantation area of the dorsal skin of the mouse was irradiated with blue light (200 W/m$^2$; for 1 minute), and the luciferase signals generated due to the change in the luciferin substrate in the mice were measured. For performing a Dox treatment, Dox (0.1 mg/g (body weight)) was given by intraperitoneal injection 1 hour before the irradiation with blue light. To correct the change of the luciferase signals, the Eph4 cells transfected with the pEF-luc2 expression vector were independently transplanted into the mice. These control mice were imaged along with the mice transplanted with Eph4 cells transfected with PA-Tet-OFF. Luminescence data from the control mice was used to correct the light-induced transcription in the transplanted Eph4 cells transfected with PA-Tet-OFF. The average intensity of the luminescence signals measured for 30 to 60 minutes after the blue light irradiation was plotted on a bar graph.

Example 1

As an attempt to construct a PA-Tet-OFF system that induces the expression of target genes by light irradiation and a Tet-based compound, a Cry2/CIB1-PA binding switch was incorporated into the Tet-OFF system. For constructing the system, HEK293T cells as an immortalized human embryonic kidney cell line were used, and a PA-Tet gene expression system optimal for mammalian cells was investigated. Specifically, a reporter plasmid (pTREtight-Ub-ELuc reporter) containing an expression cassette having a Tet operator, a promoter which is positioned downstream of the Tet operator and controlled by the Tet operator, and a Ub-Eluc gene which is positioned downstream of the promoter and of which the expression is controlled by the promoter, a plasmid containing an expression cassette for a fusion protein obtained by fusing TetR with one of Cry2 and CIB1, and a plasmid containing an expression cassette for a fusion protein obtained by fusing a p65AD protein with the remaining other one of Cry2 and CIB1 were introduced into the HEK293T cells, thereby obtaining transformed cells. These cells were irradiated with blue light in the absence of a Tet-based compound, and the relative expression level of Ub-ELuc was investigated.

FIG. 1 is a view schematically showing the used PA-Tet-OFF candidate constructs. In FIG. 1, "PHR" represents a photolyase homology region, and "NLS" represents a nuclear localization signal. As TetR, a point mutant (represented as "TetR (I194T, 1-206)") obtained by substituting the 194th isoleucine residue in TetR (1-206) with a threonine residue was used.

FIG. 1(A) is a view schematically showing amino acid sequences of Cry2 and variants thereof. FIG. 1(B) is a view schematically showing amino acid sequences of CIB1 and variants thereof. In FIG. 1(B), "(without NLS)" means an NLS deletion variant, which is a variant obtained by substituting all of the 93rd lysine, the 94th arginine, the 106th lysine, and the 107th lysine in the NLS sequence of CIB1 (region consisting of the 93rd to 107th amino acids) with alanine. All of the used Cry2, Cry2 variants, CIB1, and CIB1 variants were subjected to codon optimization for efficient expression in mammalian cells.

FIGS. 1(C) to 1(F) are views schematically showing the combination of the TetR-containing fusion protein and the p65AD protein-containing fusion protein used in each test. FIG. 1(C) shows the combination of a TetR (I194T, 1-206)-Cry2 variant fusion construct and a p65AD-CIB1 variant fusion construct. FIG. 1(D) shows the combination of a TetR (I194T, 1-206)-Cry2 variant fusion construct and a CIB1 variant-p65AD N-terminal fusion construct. FIG. 1(E) shows the combination of a TetR (I194T, 1-206)-CIB1 variant fusion construct and a p65AD-Cry2 variant fusion construct. FIG. 1(F) shows the combination of a TetR (I194T, 1-206)-CIB1 variant fusion construct and a Cry2 variant-p65AD N-terminal fusion construct.

The light-dependent transcriptional activity of each of the candidate constructs was assayed. Blue light irradiation was performed by exposing the cells to pulsed blue light (for example, pulsed for 2 seconds every 1 minute) only 3 hours before the cell lysis. All experiments were performed in 3 independent trials (3 batches) to obtain consistent results. The results are shown in Tables 1 to 4. Table 1 shows the results obtained from the candidate construct shown in FIG. 1(C). Table 2 shows the results obtained from the candidate construct shown in FIG. 1(D). Table 3 shows the results obtained from the candidate construct shown in FIG. 1(E). Table 4 shows the results obtained from the candidate construct shown in FIG. 1(F). In Tables 1 to 4, "linker" in the column of "Element #1" represents the amino acid sequence of a linker that links TetR (I194T, 1-206) to the Cry2 variant or CIB1 variant to be fused with the C-terminal side of TetR. In addition, the column of "An initial construct screening result" shows the result of the first one batch. In this column, "Dark" and "Light" each represents a relative value (the luminescence signal intensity of Negative Control under dark conditions is regarded as 1) of luminescence signal intensity (relative expression level of Ub-ELuc) quantified through image analysis by performing luciferase assay under dark conditions or under blue-light irradiation conditions, and "Light/Dark" represents a ratio therebetween. In the column of "Three independent data sets to confirm reproducibility, "Average of the Light/Dark ratio" represents the average of "Light/Dark" ratio of three independent batches, and "S.D. of the Light/Dark ratio" is the standard deviation thereof.

TABLE 1

| Construct ID | Element #1 TetR mutation | Element #1 Linker | Element #1 Light-interacting protein | Element #2 p65 AD and light-interacting protein | An initial construct screening result Dark | An initial construct screening result Light | An initial construct screening result Light/Dark | Three independent data sets to confirm reproducibility Average of the Light/Dark ratio | Three independent data sets to confirm reproducibility S.D. of the Light/Dark ratio |
|---|---|---|---|---|---|---|---|---|---|
| Negative control | I194T | SPKKK | None (TetR only) | None (p65 AD only) | 1.0 | 1.3 | 1.3 | 1.2 | 0.4 |
| T1 | I194T | SPKKK | Cry2 PHR | p65 AD-CIB1 full | 1.1 | 1.8 | 1.6 | 1.4 | 0.2 |
| T2 | I194T | SPKKK | Cry2 PHR | p65 AD-CIB1 full no NLS | 1.1 | 2.0 | 1.8 | 2.1 | 1.0 |

TABLE 1-continued

| Construct ID | TetR mutation | Linker | Light-interacting protein | p65 AD and light-interacting protein | Dark | Light | Light/Dark | Average of the Light/Dark ratio | S.D. of the Light/Dark ratio |
|---|---|---|---|---|---|---|---|---|---|
| | Element #1 | | | Element #2 | An initial construct screening result | | | Three independent data sets to confirm reproducibility | |
| T3 | I194T | SPKKK | Cry2 PHR | p65 AD-CIBN | 1.0 | 1.1 | 1.1 | 1.0 | 0.1 |
| T4 | I194T | SPKKK | Cry2 PHR | p65 AD-CIBN no NLS | 0.9 | 1.1 | 1.2 | 1.0 | 0.1 |
| T5 | I194T | SPKKK | Cry2 PHR | NLSx2-p65 AD-CIBN no NLS | 1.0 | 1.1 | 1.2 | 1.4 | 0.7 |
| T6 | I194T | SPKKK | Cry2 PHR | p65 AD-CIB81 | 1.0 | 1.2 | 1.2 | 1.3 | 0.3 |
| T7 | I194T | SPKKK | Cry2 PHR (L348F) | p55 AD-CIB1 full | 1.0 | 1.5 | 1.5 | 1.4 | 0.3 |
| T8 | I194T | SPKKK | Cry2 PHR (L348F) | p65 AD-CIB1 full no NLS | 1.1 | 1.4 | 1.4 | 1.3 | 0.3 |
| T9 | I194T | SPKKK | Cry2 PHR (L348F) | p65 AD-CIBN | 1.1 | 1.1 | 1.0 | 0.8 | 0.2 |
| T10 | I194T | SPKKK | Cry2 PHR (L348F) | p65 AD-CIBN no NLS | 1.1 | 1.1 | 1.0 | 0.8 | 0.1 |
| T11 | I194T | SPKKK | Cry2 PHR (L348F) | NLSx2-p65 AD-CIBN no NLS | 1.1 | 1.1 | 1.0 | 0.9 | 0.1 |
| T12 | I194T | SPKKK | Cry2 PHR (L348F) | p65 AD-CIB81 | 1.2 | 1.1 | 1.0 | 0.9 | 0.1 |
| T13 | I194T | SPKKK | Cry2 535 | p65 AD-CIB1 full | 1.6 | 1.1 | 0.7 | 0.8 | 0.1 |
| T14 | I194T | SPKKK | Cry2 535 | p65 AD-CIB1 full no NLS | 1.6 | 1.1 | 0.7 | 0.8 | 0.1 |
| T15 | I194T | SPKKK | Cry2 535 | p65 AD-CIBN | 1.4 | 1.1 | 0.8 | 0.8 | 0.0 |
| T16 | I194T | SPKKK | Cry2 535 | p65 AD-CIBN no NLS | 1.4 | 1.1 | 0.8 | 0.8 | 0.1 |
| T17 | I194T | SPKKK | Cry2 535 | NLSx2-p65 AD-CIBN no NLS | 1.4 | 1.1 | 0.8 | 0.8 | 0.0 |
| T18 | I194T | SPKKK | Cry2 535 | p65 AD-CIB81 | 1.3 | 1.2 | 0.9 | 0.8 | 0.1 |
| T19 | I194T | SPKKK | Cry2 535 (L348F) | p65 AD-CIB1 full | 1.4 | 1.3 | 0.9 | 0.9 | 0.0 |
| T20 | I194T | SPKKK | Cry2 535 (L348F) | p55 AD-CIB1 full no NLS | 1.4 | 1.1 | 0.8 | 0.9 | 0.1 |
| T21 | I194T | SPKKK | Cry2 535 (L348F) | p65 AD-CIBN | 1.3 | 1.1 | 0.9 | 0.9 | 0.1 |
| T22 | I194T | SPKKK | Cry2 535 (L348F) | p65 AD-CIBN no NLS | 1.2 | 1.1 | 0.9 | 0.9 | 0.1 |
| T23 | I194T | SPKKK | Cry2 535 (L348F) | NLSx2-p65 AD-CIBN no NLS | 1.2 | 1.1 | 0.9 | 0.9 | 0.1 |
| T24 | I194T | SPKKK | Cry2 535 (L348F) | p65 AD-CIB81 | 1.3 | 1.1 | 0.8 | 0.9 | 0.1 |
| No transfection | — | — | — | — | 1.1 | 1.1 | 1.0 | 1.0 | 0.1 |

TABLE 2

| Construct ID | TetR mutation | Linker | Light-interacting protein | p65 AD and light-interacting protein | Dark | Light | Light/Dark | Average of the Light/Dark ratio | S.D. of the light/Dark ratio |
|---|---|---|---|---|---|---|---|---|---|
| | Element #1 | | | Element #2 | An initial construct screening result | | | Three independent data sets to confirm reproducibility | |
| Negative control | I194T | SPKKK | None (TetR only) | None (p65 AD only) | 1.0 | 1.1 | 1.1 | 1.0 | 0.1 |
| T25 | I194T | SPKKK | Cry2 PHR | CIBN-p65 AD | 2.2 | 3.7 | 1.7 | 1.5 | 0.3 |
| T26 | I194T | SPKKK | Cry2 PHR | CIBN no NLS-p65 AD | 1.1 | 2.2 | 2.0 | 1.5 | 0.5 |
| T27 | I194T | SPKKK | Cry2 PHR | CIBN-p65 AD-NLSx2 | 2.4 | 2.3 | 0.9 | 1.0 | 0.0 |
| T28 | I194T | SPKKK | Cry2 PHR | CIBN no NLS-p65 AD-NLSx2 | 1.0 | 1.3 | 1.3 | 1.0 | 0.2 |
| T29 | I194T | SPKKK | Cry2 PHR (L348F) | CIBN-p65 AD | 1.0 | 1.8 | 1.8 | 1.4 | 0.4 |
| T30 | I194T | SPKKK | Cry2 PHR (L348F) | CIBN no NLS-p65 AD | 0.8 | 1.0 | 1.4 | 1.1 | 0.3 |

TABLE 2-continued

| Construct ID | Element #1 TetR mutation | Element #1 Linker | Element #1 Light-interacting protein | Element #2 p65 AD and light-interacting protein | An initial construct screening result Dark | Light | Light/Dark | Three independent data sets to confirm reproducibility Average of the Light/Dark ratio | S.D. of the light/Dark ratio |
|---|---|---|---|---|---|---|---|---|---|
| T31 | I194T | SPKKK | Cry2 PHR (L348F) | CIBN-p65 AD-NLSx2 | 1.3 | 1.3 | 1.0 | 1.0 | 0.1 |
| T32 | I194T | SPKKK | Cry2 PHR (L348F) | CIBN no NLS-p65 AD-NLSx2 | 0.8 | 0.9 | 1.2 | 1.0 | 0.2 |
| T33 | I194T | SPKKK | Cry2 535 | CIBN-p65 AD | 0.9 | 1.1 | 1.3 | 0.9 | 0.3 |
| T34 | I194T | SPKKK | Cry2 535 | CIBN no NLS-p65 AD | 0.8 | 0.7 | 0.9 | 0.8 | 0.1 |
| T35 | I194T | SPKKK | Cry2 535 | CIBN-p65 AD-NLSx2 | 1.2 | 1.0 | 0.8 | 0.8 | 0.1 |
| T36 | I194T | SPKKK | Cry2 535 | CIBN no NLS-p65 AD-NLSx2 | 0.8 | 0.7 | 0.8 | 0.8 | 0.1 |
| T37 | I194T | SPKKK | Cry2 535 (L348F) | CIBN-p65 AD | 0.8 | 1.0 | 1.4 | 1.0 | 0.3 |
| T38 | I194T | SPKKK | Cry2 535 (L348F) | CIBN no NLS-p65 AD | 0.7 | 0.8 | 1.2 | 1.0 | 0.3 |
| T39 | I194T | SPKKK | Cry2 535 (L348F) | CIBN-p65 AD-NLSx2 | 1.1 | 1.0 | 1.0 | 0.9 | 0.1 |
| T40 | I194T | SPKKK | Cry2 535 (L348F) | CIBN no NLS-p65 AD-NLSx2 | 0.8 | 0.8 | 1.0 | 0.9 | 0.2 |
| No transfection | — | — | — | — | 0.7 | 0.7 | 1.0 | 0.8 | 0.1 |

TABLE 3

| Construct ID | Element #1 TetR mutation | Element #1 Linker | Element #1 Light-interacting protein | Element #2 p65 AD and light-interacting protein | An initial construct screening result Dark | Light | Light/Dark | Three independent data sets to confirm reproducibility Average of the Light/Dark ratio | S.D. of the Light/Dark ratio |
|---|---|---|---|---|---|---|---|---|---|
| Negative control | I194T | SPKKK | None (TetR only) | None (p65 AD only) | 1.0 | 1.1 | 1.2 | 1.0 | 0.2 |
| T41 | I194T | SPKKK | CIB1 full | p65 AD-Cry2 PHR | 13.8 | 20.7 | 1.6 | 1.6 | 0.2 |
| T42 | I194T | SPKKK | CIB1 full | p65 AD-Cry2 PHR (L348F) | 8.3 | 17.2 | 2.2 | 1.7 | 0.5 |
| T43 | I194T | SPKKK | CIB1 full | p65 AD-Cry2 535 | 4.3 | 8.7 | 2.1 | 2.1 | 0.9 |
| T44 | I194T | SPKKK | CIB1 full | p65 AD-Cry2 535 (L348F) | 4.8 | 10.5 | 2.3 | 2.0 | 0.3 |
| T45 | I194T | SPKKK | CIB1 full | NLSx2-p65 AD-Cry2 PHR | 21.9 | 50.9 | 2.4 | 1.9 | 0.8 |
| T46 | I194T | SPKKK | CIB1 full | NLSx2-p65 AD-Cry2 PHR (L348F) | 19.3 | 34.3 | 1.8 | 1.7 | 0.2 |
| T47 | I194T | SPKKK | CIB1 full no NLS | p65 AD-Cry2 PHR | 36.2 | 65.2 | 2.0 | 1.5 | 0.6 |
| T48 | I194T | SPKKK | CIB1 full no NLS | p65 AD-Cry 2PHR (L348F) | 33.0 | 47.9 | 1.6 | 1.4 | 0.2 |
| T49 | I194T | SPKKK | CIB1 full no NLS | p65 AD-Cry2 535 | 10.4 | 31.8 | 3.3 | 2.0 | 1.2 |
| 750 | I194T | SPKKK | CIB1 full no NLS | p65 AD-Cry2 535 (L348F) | 9.3 | 23.9 | 2.7 | 2.0 | 0.6 |
| T51 | I194T | SPKKK | CIB1 full no NLS | NLSx2-p65 AD-Cry2 PHR | 56.0 | 109.4 | 2.2 | 1.6 | 0.6 |
| T52 | I194T | SPKKK | CIB1 full no NLS | NLSx2-p65 AD-Cry2 PHR (L348F) | 50.2 | 86.8 | 1.9 | 1.4 | 0.4 |
| T53 | I194T | SPKKK | CIBN | p65 AD-Cry2 PHR | 0.6 | 34.8 | 64.7 | 42.1 | 19.7 |
| T54 | I194T | SPKKK | CIBN | p65 AD-Cry2 PHR (L348F) | 0.5 | 1.8 | 3.7 | 3.9 | 2.3 |
| T55 | I194T | SPKKK | CIBN | p65 AD-Cry2 535 | 0.3 | 13.0 | 51.2 | 43.1 | 7.5 |
| T56 | I194T | SPKKK | CIBN | p65 AD-Cry2 535 (L348F) | 0.3 | 2.1 | 7.0 | 8.1 | 5.1 |
| T57 | I194T | SPKKK | CIBN | NLSx2-p65 AD-Cry2 PHR | 1.4 | 65.7 | 47.6 | 39.1 | 20.4 |
| T58 | I194T | SPKKK | CIBN | NLSx2-p65 AD-Cry2 PHR (L348F) | 0.5 | 7.2 | 13.5 | 19.3 | 13.1 |
| T59 | I194T | SPKKK | CIBN no NLS | p65 AD-Cry2 PHR | 0.8 | 20.2 | 40.8 | 27.3 | 14.0 |
| T60 | I194T | SPKKK | CIBN no NLS | p65 AD-Cry2 PHR (L348F) | 0.9 | 6.1 | 7.6 | 8.3 | 4.0 |
| T61 | I194T | SPKKK | CIBN no NLS | p65 AD-Cry2 535 | 0.5 | 21.0 | 91.5 | 45.9 | 39.9 |
| T62 | I194T | SPKKK | CIBN no NLS | p65 AD-Cry2 535 (L348F) | 0.5 | 5.7 | 25.0 | 13.3 | 10.7 |
| T63 | I194T | SPKKK | CIBN no NLS | NLSx2-p65 AD-Cry2 PHR | 2.4 | 129.6 | 69.5 | 38.0 | 32.2 |
| T64 | I194T | SPKKK | CIBN no NLS | NLSx2-p65 AD-Cry 2PHR (L348F) | 1.7 | 21.0 | 12.5 | 14.3 | 4.8 |
| T65 | I194T | SPKKK | CIB81 | p65 AD-Cry2 PHR | 77.7 | 211.3 | 2.7 | 2.3 | 0.8 |
| T66 | I194T | SPKKK | CIB81 | p65 AD-Cry2 PHR (L348F) | 61.2 | 355.7 | 6.0 | 4.7 | 1.8 |

TABLE 3-continued

| Construct ID | Element #1 TetR mutation | Element #1 Linker | Element #1 Light-interacting protein | Element #2 p65 AD and light-interacting protein | An initial construct screening result Dark | An initial construct screening result Light | An initial construct screening result Light/Dark | Three independent data sets to confirm reproducibility Average of the Light/Dark ratio | Three independent data sets to confirm reproducibility S.D. of the Light/Dark ratio |
|---|---|---|---|---|---|---|---|---|---|
| T67 | I194T | SPKKK | CIB81 | p65 AD-Cry2 535 | 21.8 | 171.4 | 7.9 | 6.0 | 3.1 |
| T68 | I194T | SPKKK | CIB81 | p65 AD-Cry2 535 (L348F) | 28.7 | 212.5 | 7.4 | 6.1 | 1.6 |
| T69 | I194T | SPKKK | CIB81 | NLSx2-p65 AD-Cry2 PHR | 322.6 | 656.5 | 2.1 | 1.8 | 0.5 |
| T70 | I194T | SPKKK | CIB81 | NLSx2-p65 AD-Cry2 PHR (L348F) | 146.0 | 423.6 | 2.9 | 2.6 | 0.6 |
| No transfection | — | — | — | — | 0.0 | 0.1 | 2.5 | 2.3 | 1.0 |

TABLE 4

| Construct ID | Element #1 TetR mutation | Element #1 Linker | Element #1 Light-interacting protein | Element #2 p65 AD and light-interacting protein | An initial construct screening result Dark | An initial construct screening result Light | An initial construct screening result Light/Dark | Three independent data sets to confirm reproducibility Average of the light/Dark ratio | Three independent data sets to confirm reproducibility S.D. of the Light/Dark ratio |
|---|---|---|---|---|---|---|---|---|---|
| Negative control | I194T | SPKKK | None (TetR only) | None (p65 AD only) | 1.0 | 1.0 | 1.0 | 0.8 | 0.2 |
| T71 | I194T | SPKKK | CIB1 full | Cry2 PHR-p65 AD | 2.4 | 4.1 | 1.7 | 1.5 | 0.2 |
| T72 | I194T | SPKKK | CIB1 full | Cry2 PHR (L348F)-p65 AD | 2.7 | 4.3 | 1.6 | 1.6 | 0.4 |
| T73 | I194T | SPKKK | CIB1 full | Cry2 PHR-p65 AD-NLSx2 | 20.1 | 16.6 | 0.8 | 0.9 | 0.2 |
| T74 | I194T | SPKKK | CIB1 full | Cry2 PHR (L348F)-p65 AD-NLSx2 | 5.1 | 6.8 | 1.4 | 1.0 | 0.4 |
| T75 | I194T | SPKKK | CIB1 full no NLS | Cry2 PHR-p65 AD | 3.0 | 5.4 | 2.0 | 1.4 | 0.5 |
| T76 | I194T | SPKKK | CIB1 full no NLS | Cry2 PHR (L348F)-p65 AD | 4.8 | 7.2 | 1.5 | 1.2 | 0.3 |
| T77 | I194T | SPKKK | CIB1 full no NLS | Cry2 PHR-p65 AD-NLSx2 | 30.1 | 25.2 | 0.9 | 0.9 | 0.1 |
| T78 | I194T | SPKKK | CIB1 full no NLS | Cry2 PHR (L348F)-p65 AD-NLSx2 | 11.3 | 12.4 | 1.2 | 0.9 | 0.3 |
| T79 | I194T | SPKKK | CIBN | Cry2 PHR-p65 AD | 1.2 | 5.0 | 4.3 | 5.6 | 3.5 |
| T80 | I194T | SPKKK | CIBN | Cry2 PHR (L348F)-p65 AD | 0.9 | 11.0 | 12.7 | 53.1 | 35.6 |
| T81 | I194T | SPKKK | CIBN | Cry2 PHR-p65 AD-NLSx2 | 4.3 | 6.9 | 1.7 | 1.5 | 0.2 |
| T82 | I194T | SPKKK | CIBN | Cry2 PHR (L348F)-p65 AD-NLSx2 | 0.9 | 7.0 | 7.4 | 11.4 | 6.7 |
| T83 | I194T | SPKKK | CIBN no NLS | Cry2 PHR-p65 AD | 1.1 | 2.3 | 2.0 | 2.7 | 0.8 |
| T84 | I194T | SPKKK | CIBN no NLS | Cry2 PHR (L348F)-p65 AD | 0.9 | 4.7 | 5.4 | 8.7 | 5.6 |
| T85 | I194T | SPKKK | CIBN no NLS | Cry2 PHR-p65 AD-NLSx2 | 1.5 | 5.2 | 3.7 | 2.9 | 0.7 |
| T86 | I194T | SPKKK | CIBN no NLS | Cry2 PHR (L348F)-p65 AD-NLSx2 | 1.0 | 8.4 | 8.4 | 10.7 | 3.7 |
| T87 | I194T | SPKKK | CIB81 | Cry2 PHR-p65 AD | 4.8 | 10.7 | 2.3 | 1.4 | 0.7 |
| T88 | I194T | SPKKK | CIB81 | Cry2 PHR (L348F)-p65 AD | 6.6 | 17.0 | 2.6 | 2.0 | 0.7 |
| T89 | I194T | SPKKK | CIB81 | Cry2 PHR-p65 AD-NLSx2 | 130.2 | 73.7 | 0.6 | 0.8 | 0.2 |
| T90 | I194T | SPKKK | CIB81 | Cry2 PHR (L348F)-p65 AD-NLSx2 | 37.1 | 34.8 | 1.0 | 1.2 | 0.3 |
| No transfection | — | — | — | — | 0.8 | 0.7 | 0.8 | 1.2 | 0.3 |

As shown in Tables 1 to 4, it was revealed that in a case where a construct (FIGS. 1(E) and 1(F)) constructed by linking TetR (I194T, 1-206) to the N-terminal side of CIB1 or a variant thereof is used, the ratio of Ub-Eluc expression level under the light irradiation conditions to the Ub-Eluc expression level under the dark conditions (value in the column of "Average of the Light/Dark ratio" in the table) is higher, and the expression of Ub-Eluc is more efficiently induced by blue light irradiation, than in a case where a construct (FIGS. 1(C) and 1(D)) constructed by linking TetR (I194T, 1-206) to the N-terminal side of Cry2 or a variant thereof is used. Particularly, the combination of the TetR (I194T, 1-206)-CIB1 variant fusion construct and the p65AD-Cry2 variant fusion construct (FIG. 1(E)) tended to bring about a higher Light/Dark ratio and higher PA-Tet-controlled expression efficiency, compared to the combination of the TetR (I194T, 1-206)-CIB1 variant fusion construct and the Cry2 variant-p65AD N-terminal fusion construct (FIG. 1(F)). Especially, compared to other candidate constructs, the constructs (with construct ID of T53, T55, T57, T59, T61, and T63) using CIBN (partial construct consisting of residues 1 to 170 of CIB1) or CIBN (-NLS) (construct obtained by removing the nuclear localization signal by introducing a mutation into NLS of CIBN) as a CIB1 variant and using Cry2 PHR (partial construct consisting of residues 1 to 496 of Cry2) or Cry2 535 (partial construct consisting of residues 1 to 535 of Cry2) as a Cry2 variant brought about markedly higher PA-Tet-controlled expression efficiency. Furthermore, by the comparison between the T59 construct and the T63 construct and the comparison between the T60 construct and the T64 construct, it was revealed that in a case where CIBN (-NLS) is used as a CIB1 variant, by linking two nuclear localization signals in tandem to the N-terminal side of p65AD ("NLS×2" in the table), the PA-Tet-controlled expression efficiency is further improved.

Example 2

By using the T86 construct (Element #1: SEQ ID NO: 5, Element #2: SEQ ID NO: 6) confirmed to be the PA-Tet-OFF construct in Example 1, the influence of the linker sequence of TetR and a CIB1 derivative on the PA-Tet-controlled expression efficiency and the influence of the I194 amino acid substitution in TetR on the PA-Tet-controlled expression efficiency were investigated. As a control, the construct as "Negative control" shown in Table 4 (Element #1: SEQ ID NO: 7, Element #2: SEQ ID NO: 8) was used. In addition, a construct obtained by replacing TetR (I194T, 1-206) in the T86 construct with wild-type TetR (1-206) was also tested in the same manner, and the influence of the linker sequence was investigated.

FIG. 2(A) is a schematic view of the expression cassette containing the T86 construct used in Example 1. FIG. 2(B) is a schematic view of the Ub-Eluc expression cassette of the pTREtight-Ub-ELuc reporter used in Example 1. FIG. 2(C) is a schematic view of the expression cassette for a protein [TetR (I194T, 1-206)-CIB1 (-NLS)-T2A-Cry2 PHR (L348F)-p65AD-NLS×2 fusion construct] (SEQ ID NO: 9) in which TetR (I194T, 1-206)-CIB1 (-NLS) fusion construct and Cry2 PHR (L348F)-p65AD-NLS×2 fusion construct are linked to each other through a T2A self-cleaving peptide. As in Example 1, in a case where the plasmid containing the expression cassette (SEQ ID NO: 12) for a TetR (I194T, 1-206)-CIB1 (-NLS)-T2A-Cry2 PHR (L348F)-p65ad-NLS×2 fusion construct was expressed in cells, the T86 construct brought about higher PA-Tet-controlled expression efficiency, than in a case where the plasmid containing the expression cassette (SEQ ID NO: 10) for a TetR (I194T, 1-206)-CIB1 (-NLS) fusion construct and the plasmid containing the expression cassette (SEQ ID NO: 11) for a Cry2 PHR (L348F)-p65AD-NLS×2 fusion construct were co-expressed in cells. Therefore, in order to verify the effect of the linker sequence and to verify the effect of the I194 amino acid substitution in TetR, the TetR (I194T, 1-206)-CIB1 (-NLS)-T2A-Cry2 PHR (L348F)-p65AD-NLS×2 fusion construct was appropriately modified and used.

Figure 3:
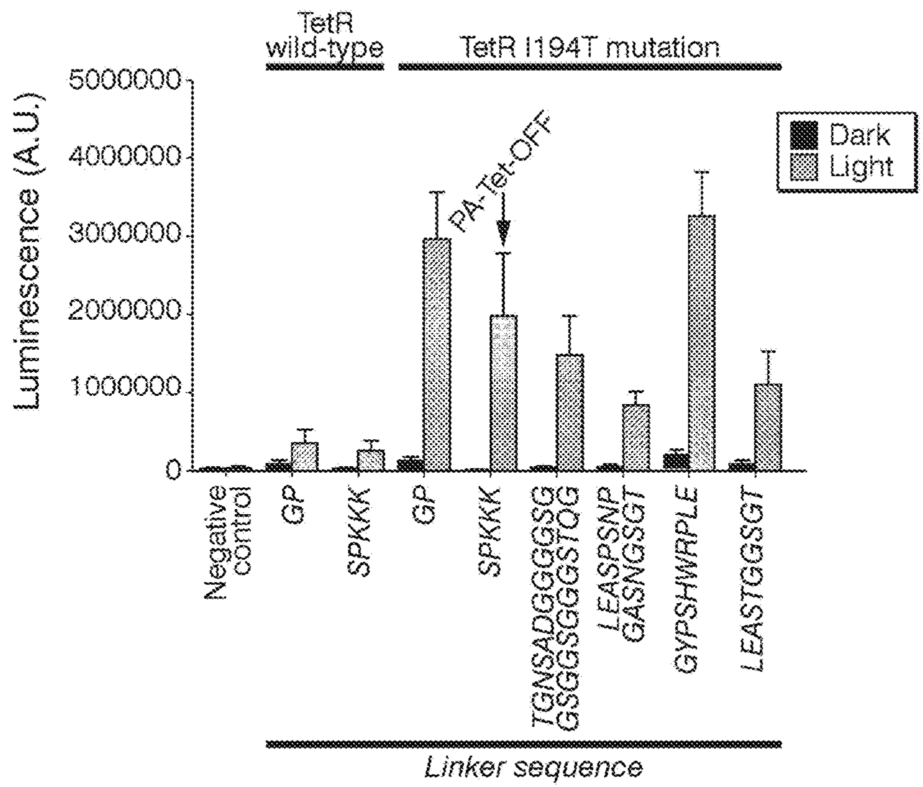
FIG. 3 is a view showing the results of investigating the influence of linker sequences for TetR and a CIB1 derivative on the PA-Tet-controlled expression efficiency in Example 2 by using a T86 construct.

A plasmid containing an expression cassette for a gene encoding the protein or a variant thereof shown in FIG. 3 was introduced into HEK293T cells together with the pTREtight-Ub-ELuc reporter, thereby obtaining transformed cells. These cells were irradiated with blue light in the absence of a Tet-based compound, and the light-dependent transcriptional activity of Ub-ELuc was investigated.

Figure 4:
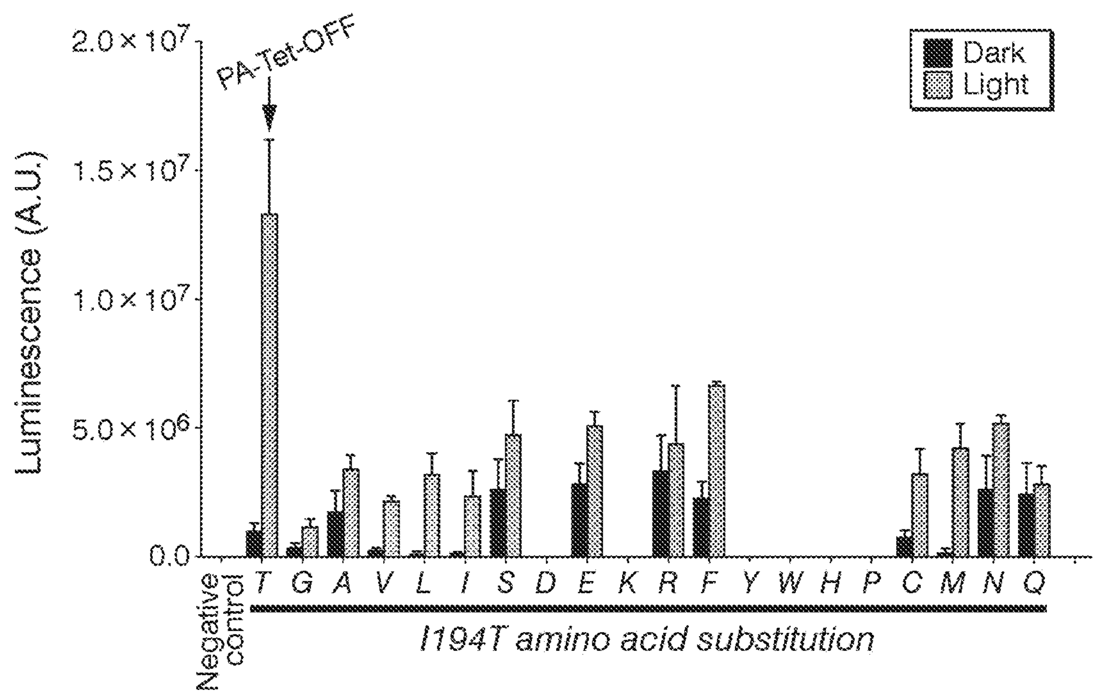
FIG. 4 is a view showing the results of investigating the influence of the I194 amino acid substitution in TetR on the PA-Tet-controlled expression efficiency in Example 2 by using a T86 construct.

For the verification of the effect of the linker sequence of TetR and a CIB1 derivative, as linker sequences, GP consisting of 2 amino acids, SPKKK consisting of 5 amino acids (SEQ ID NO: 13), TGNSADGGGGSGGSGGSGGGSTQG consisting of 24 amino acids (SEQ ID NO: 14), LEASPSNPGASNGSGT (SEQ ID NO: 15) consisting of 16 amino acids, GYPSHWRPLE consisting of 10 amino acids (SEQ ID NO: 16), and LEASTGGSGT consisting of 10 amino acids (SEQ ID NO: 17) were used. For each construct, luciferase assay was performed under dark conditions ("Dark" in FIG. 3) and under blue-light irradiation conditions ("Light" in FIG. 3), and the luminescence signal intensity quantified by image analysis was measured. The measurement results are shown in FIG. 4. The data in FIG. 4 represent mean±standard deviation (n=3). In addition, all the experiments were repeated 3 times to obtain consistent results.

As shown in FIG. 3, it was revealed that compared to the construct using TetR (1-206), the construct using TetR (I194T, 1-206) induces a higher level of Ub-ELuc expression under the blue-light irradiation conditions and brings about higher PA-Tet-controlled expression efficiency. Furthermore, it was revealed that the type of the linker sequence linking TetR (I194T, 1-206) to CIB1 (-NLS) affects the PA-Tet-controlled expression efficiency. Particularly, in a case where SPKKK was used as a linker sequence, Ub-ELuc was sufficiently expressed to a high level under the blue-light irradiation conditions while substantially not being expressed under the dark conditions, and the PA-Tet-controlled expression efficiency was especially excellent.

For the verification of the effect of the I194 amino acid substitution in TetR, variants obtained by substituting I194 in TetR with the amino acids shown in FIG. 4 were used. For each construct, luciferase assay was performed in the same manner, and the luminescence signal intensity quantified by image analysis was measured. The measurement results are shown in FIG. 4. The data in FIG. 4 represent mean±standard deviation (n=3). In addition, all the experiments were repeated 3 times to obtain consistent results. As a result, it was revealed that TetR (I194T, 1-206) in which I194 was substituted with threonine brings about markedly excellent PA-Tet-controlled expression efficiency.

Example 3

By using the T86 construct confirmed to be the PA-Tet-OFF construct in Example 1, an attempt was made to construct a Tet-based compound-independent PA expression control system (PA-Tet-independent system) and a PA-Tet-ON system. Dox was used as a Tet-based compound.

Figure 2:
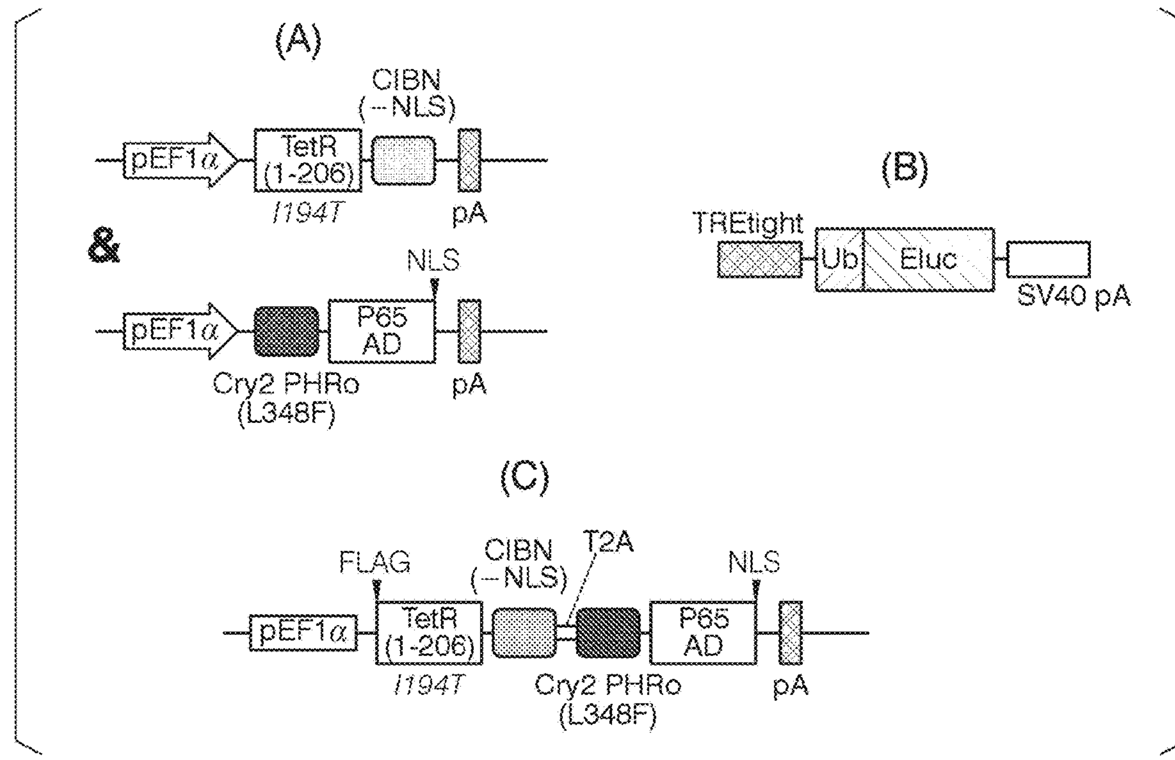
FIG. 2(A) is a schematic view of an expression cassette including a T86 construct confirmed to be a PA-Tet-OFF construct in Example 1.
FIG. 2(B) is a schematic view of a Ub-Eluc expression cassette for a pTREtight-Ub-ELuc reporter used in Example 1.
FIG. 2(C) is a schematic view of an expression cassette for a protein in which a TetR (I194T, 1-206)-CIB1 (-NLS) fusion construct and a Cry2 PHR (L348F)-p65AD-NLS×2 fusion construct are linked to each other through a T2A self-cleaving peptide [TetR (I194T, 1-206)-CIB1 (-NLS)-T2A-Cry2 PHR (L348F)-p65AD-NLS×2 fusion construct].

A construct of the PA-Tet-independent system was constructed by introducing H100Y (point mutation for substituting the 100th histidine residue with tyrosine, the same shall be applied hereinafter) into TetR (I194T, 1-206) in the T86 construct shown in FIG. 2(C). In addition, a construct of the PA-Tet-ON system was constructed by introducing 5 types of reverse phenotypic mutations (Reverse Tet mutations) known for TetR into TetR (I194T, 1-206) in the T86 construct shown in FIG. 2 (C): rtTA (E71K, D95N, L101S, and G102D), S2 (E19G, A56P, D148E, and H179R), M2 (S12G, E19G, A56P, D148E, and H179R), V10 (E19G, A56P, F67S, F86Y, D148E, R171K, and H179R), V16 (V9I, E19G, A56P, F67S, F86Y, D148E, R171K, and H179R). As a comparison target, the T86 construct shown in FIG. 2(A) was also used.

Figure 5:
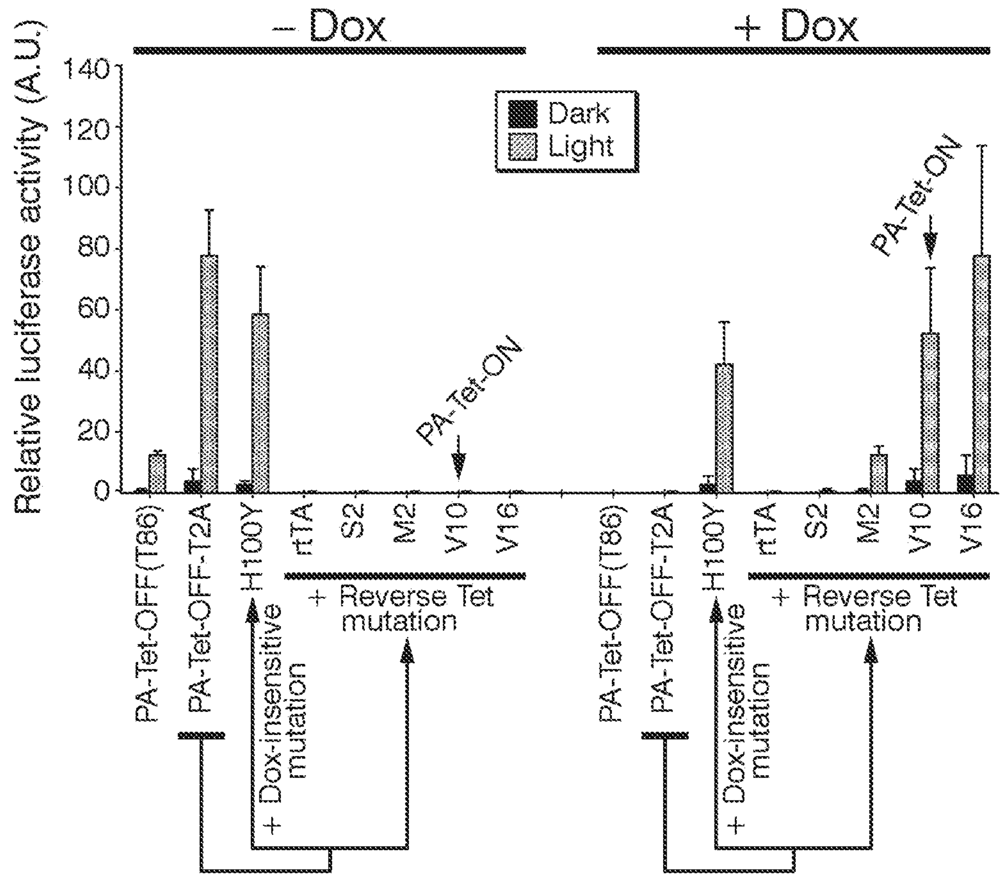
FIG. 5 is a view showing the results of measuring luminescence signal intensity quantified by performing luciferase assay in Example 3 on Tet-independent constructs and PA-Tet-ON constructs obtained by introducing mutations into TetR (I194T, 1-206) in a T86 construct, the results obtained by performing the luciferase assay under dark conditions and blue-light irradiation conditions with or without administering Dox.

For each construct, a plasmid containing the expression cassette was introduced into HEK293T cells together with a pTREtight-Ub-ELuc reporter, thereby obtaining transformed cells. These cells were irradiated with blue light in the absence of Dox or in the presence of Dox, and the light-dependent transcriptional activity of Ub-ELuc was investigated. All experiments were performed in 3 independent trials (3 batches) to obtain consistent results. FIG. 5 shows a measured value (A.U.) of the luminescence signal intensity (relative expression level of Ub-ELuc) quantified by image analysis after performing a luciferase assay under dark conditions and under blue-light irradiation conditions. In Table 5, the column of "An initial construct screening result" shows the result of the first batch. In this column, "Dark" and "Light" each represents a relative value (the luminescence signal intensity of Negative Control of Example 1 under dark conditions is regarded as 1) of luminescence signal intensity (expression level of Ub-ELuc) under dark conditions or under blue-light irradiation conditions, and "Light/Dark" represents a Light/Dark ratio. The column of "Three independent data sets to confirm reproducibility" shows the average of Light/Dark ratios of three independent batches and the standard deviations thereof.

brought about by the blue light irradiation was markedly higher than in a case where the T86 construct ("PA-Tet-OFF (T86)" in FIG. 5) shown in FIG. 2(A) was used. The blue light-dependent transcriptional activity of these constructs disappeared in the presence of Dox. In the construct (PA-Tet-H100Y) using TetR (I194T, H100Y, 1-206), Ub-Eluc was expressed in both the presence of Dox and the absence of Dox, and the expression of Ub-Eluc was induced by only the blue light irradiation, which indicates that the expression of Ub-Eluc is not affected by Dox. On the other hand, in all the variants obtained by introducing the reverse phenotypic mutation into TetR (I194T, 1-206), Ub-Eluc was not expressed in the absence of Dox regardless of whether or not the blue light irradiation was performed. However, in the presence of Dox, the expression of Ub-Eluc was induced by blue light irradiation in the M2 variant, the V10 variant, and the V16 variant. Especially, in the V10 variant, Ub-ELuc was sufficiently expressed to a high level under blue-light irradiation conditions while substantially not being expressed under dark conditions, which indicates that the V10 variant brings about particularly excellent PA-Tet-controlled expression efficiency.

Next, the PA-Tet-OFF/ON system and the conventional Tet-OFF/ON system were compared with each other. As the PA-Tet-OFF/ON system, a PA-Tet-OFF-T2A construct and a PA-Tet-ON-T2A construct were used. As the conventional Tet-OFF/ON system, a commercially available "tTA-Ad" construct and a "Tet-ON 3G" construct (manufactured by Clontech/Takara Bio Inc.) were used. For each construct, a plasmid containing the expression cassette was introduced into HEK293T cells together with a pTREtight-Ub-ELuc reporter, thereby obtaining transformed cells. These cells were irradiated with blue light in the absence of Dox or in the presence of Dox, and the light-dependent transcriptional activity of Ub-ELuc was investigated. Under the blue-light irradiation conditions, cells were exposed to blue light pulses (pulsed for 1 second every 30 seconds) for 36 hours.

TABLE 5

| Construct name and ID | Dox (ng/mL) | An initial construct screening result: Dark | Light | Light/Dark | Three independent data sets to confirm reproducibility: Average of the Light/Dark ratio | S.D. of the Light/Dark ratio |
|---|---|---|---|---|---|---|
| PA-Tet-OFF (T86) | 0 | 0.8 | 12.3 | 33.8 | 16.0 | 15.8 |
| PA-Tet-OFF-T2A | 0 | 4.0 | 76.7 | 36.2 | 19.0 | 15.0 |
| PA-Tet + H100Y mutation | 0 | 2.6 | 58.1 | 30.6 | 19.0 | 11.1 |
| PA-Tet + rtTA mutation | 0 | 0.2 | 0.5 | 3.5 | 3.2 | 0.8 |
| PA-Tet + S2 mutation | 0 | 0.2 | 0.5 | 3.1 | 2.2 | 0.7 |
| PA-Tet + M2 mutation | 0 | 0.3 | 0.3 | 1.1 | 1.4 | 0.6 |
| PA-Tet-ON (V10 mutation) | 0 | 0.2 | 0.2 | 1.1 | 1.3 | 0.6 |
| PA-Tet + V16 mutation | 0 | 0.2 | 0.3 | 1.6 | 1.5 | 0.7 |
| PA-Tet-OFF (T86) | 75 | 0.1 | 0.1 | 1.2 | 1.7 | 0.4 |
| PA-Tet-OFF-T2A | 75 | 0.1 | 0.1 | 0.9 | 1.1 | 0.2 |
| PA-Tet + H100Y mutation | 75 | 3.1 | 41.4 | 22.7 | 19.4 | 6.3 |
| PA-Tet + rtTA mutation | 75 | 0.1 | 0.4 | 3.4 | 22.5 | 17.3 |
| PA-Tet + S2 mutation | 75 | 0.2 | 0.7 | 3.1 | 17.0 | 12.8 |
| PA-Tet + M2 mutation | 75 | 0.3 | 12.7 | 38.4 | 31.6 | 8.1 |
| PA-Tet-ON (V10 mutation) | 75 | 1.2 | 51.7 | 42.7 | 32.8 | 11.5 |
| PA-Tet + V16 mutation | 75 | 5.9 | 76.7 | 26.4 | 15.8 | 10.5 |

Figure 6:
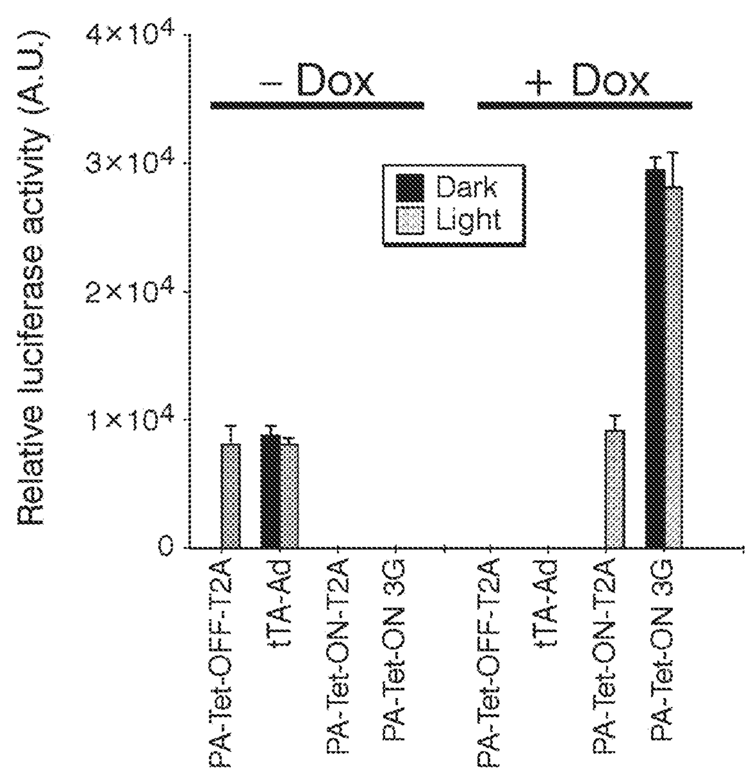
FIG. 6 is a view showing the results of measuring luminescence signal intensity quantified by performing luciferase assay in Example 3 on a PA-Tet-OFF-T2A construct and a PA-Tet-ON-T2A construct obtained by introducing mutations into a T86 construct and on constructs of the conventional Tet-OFF/ON system (a tTA-Ad construct and a Tet-ON 3G construct), the results obtained by performing the luciferase assay under dark conditions and blue-light irradiation conditions with or without administering Dox.

As in Example 2, in the absence of Dox, in a case where the T86 construct ("PA-Tet-OFF-T2A" in FIG. 5) shown in FIG. 2(C) was used, the expression induction efficiency All experiments were performed in 3 independent trials (3 batches) to obtain consistent results. FIG. 6 shows a measured value (A.U.) of the luminescence signal intensity (relative expression level of Ub-ELuc) quantified by image analysis after performing a luciferase assay under dark conditions and under blue-light irradiation conditions. In Table 6, the column of "An initial construct screening result" and the column of "Three independent data sets to confirm reproducibility" are the same as those in Table 5. As a result, the longer the cells were irradiated with blue light, the more the luciferase reporter activity induced by the PA-Tet-OFF/ON system was dramatically increased to an extent equivalent to the luciferase reporter activity induced by a conventional system controlled by only Tet.

TABLE 6

| Construct name and ID | Dox (ng/mL) | An initial construct screening result | | | Three independent data sets to confirm reproducibility | |
|---|---|---|---|---|---|---|
| | | Dark | Light | Light/Dark | Average of the Light/Dark ratio | S.D. of the Light/Dark ratio |
| PA-Tet-OFF-T2A | 0 | 15.4 | 8090.9 | 525.3 | 2782.8 | 2091.4 |
| tTA-Ad (Clontech/TAKARA) | 0 | 8877.6 | 8116.2 | 0.9 | 1.1 | 0.2 |
| PA-Tet-ON-T2A | 0 | 3.6 | 25.3 | 9.2 | 9.6 | 1.0 |
| Tet-ON 3G (Clontech/TAKARA) | 0 | 29.6 | 37.7 | 1.3 | 1.5 | 0.2 |
| PA-Tet-OFF-T2A | 500 | 9.9 | 1.8 | 0.2 | 0.2 | 0.0 |
| tTA-Ad (Clontech/TAKARA) | 500 | 19.6 | 30.6 | 1.7 | 2.2 | 0.5 |
| PA-Tet-ON-T2A | 500 | 22.8 | 9140.6 | 412.5 | 959.1 | 514.4 |
| Tet-ON 3G (Clontech/TAKARA) | 500 | 29839.8 | 28378.1 | 1.0 | 1.0 | 0.1 |

Figure 7:
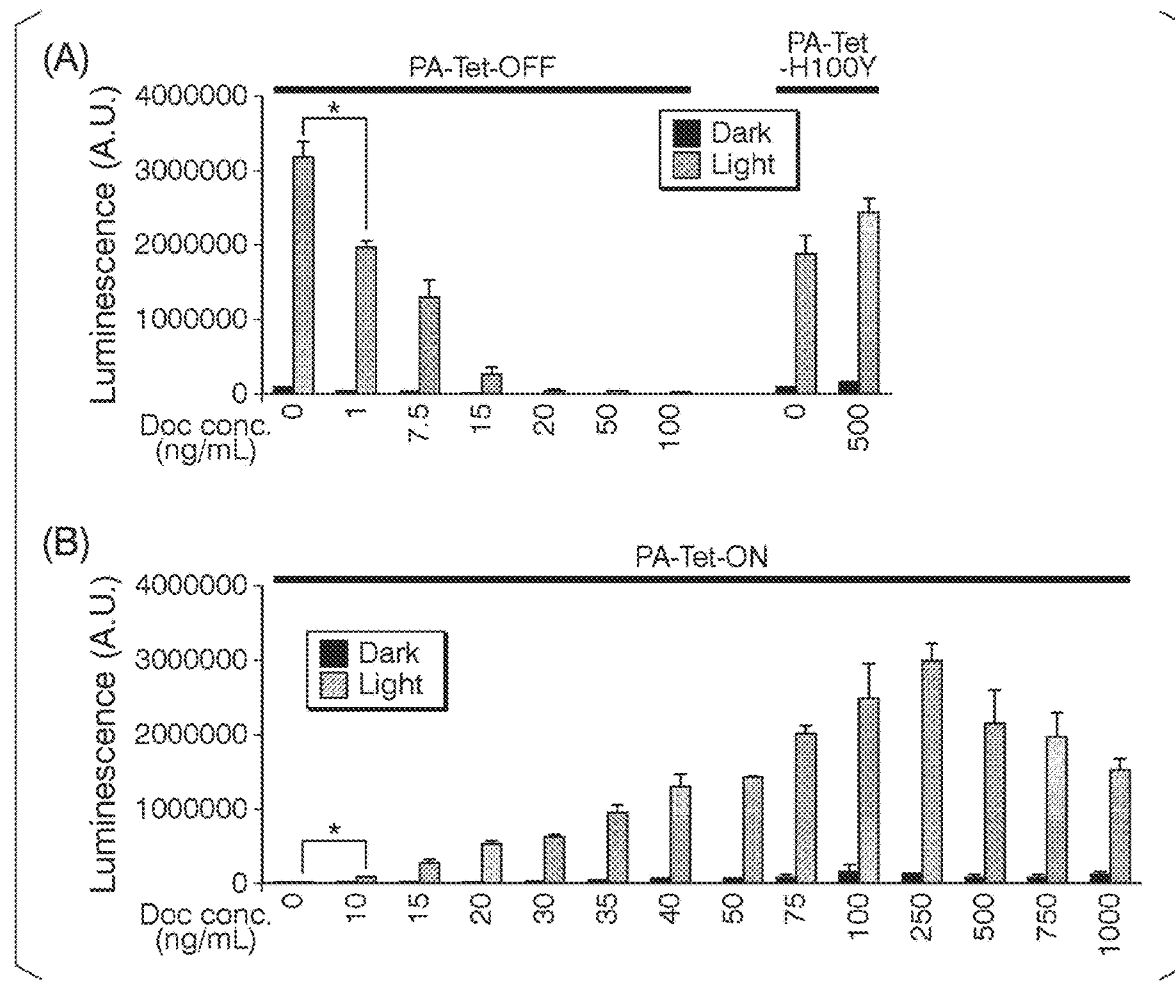
FIG. 7 is a view showing the results of investigating Dox concentration-dependent transcriptional activity of a PA-Tet-OFF system (A) and a PA-Tet-ON system (B) in HEK293T cells transiently transfected in Example 3.

In addition, for the PA-Tet-OFF system using the PA-Tet-OFF-T2A construct and the PA-Tet-independent system using the PA-Tet-H100Y construct, the influence of DOx concentration on the PA-Tet-controlled expression efficiency was investigated. The results are shown in FIG. 7(A). Furthermore, for the PA-Tet-ON system using a construct obtained by introducing a V10 mutation into the PA-Tet-OFF-T2A construct (PA-Tet-ON-T2A construct), the influence of Dox concentration on the PA-Tet-controlled expression efficiency was investigated. The results are shown in FIG. 7(B). The data represent mean±standard deviation (n=3) obtained from one experiment. In FIGS. 7(A) and 7(B), "*" means $p<0.05$ (paired student's t-test).

In the PA-Tet-OFF system, Dox attenuated the PA-Tet-controlled gene expression in a concentration-dependent manner (FIG. 7(A)). Conversely, at a Dox concentration of 0 to 250 ng/mL, the PA-Tet-controlled gene expression increased in correlation with the Dox concentration in the PA-Tet-ON system (FIG. 7(B)). Particularly, even under the conditions where the Dox concentration was extremely low (1 ng/mL for the PA-Tet-OFF system and 10 ng/mL for the PA-Tet-ON system), the effect brought about by Dox was observed in both systems. On the other hand, in the PA-Tet-independent system, the Dox concentration dependence was not confirmed. In the PA-Tet-ON system, the induced luciferase activity was slightly reduced at a Dox concentration higher than 250 ng/mL, which indicates that there is an optimal Dox concentration for gene expression. The Dox concentration at which the gene expression is maximized depends on the cell type and the gene delivery method.

Example 4

The PA-Tet-OFF system and the PA-Tet-ON system were introduced into Eph4 cells by using a lentiviral vector, thereby preparing stable expression strains of these systems. The Dox concentration dependence and the blue light intensity dependence of these strains were investigated.

FIG. 8(A) is a schematic view of an expression cassette for a PA-Tet-OFF construct/PA-Tet-ON construct used for preparing the PA-Tet-OFF/ON system stable expression strains. FIG. 8(B) is a schematic view of a Ub-NLS-luc2 expression cassette in a TRE3G-Ub-NLS-luc2-Hes1 3'UTR lentiviral vector. Eph4 cells were transduced with these genes, thereby preparing a PA-Tet-OFF system stable strain and a PA-Tet-ON system stable strain.

Figure 9:
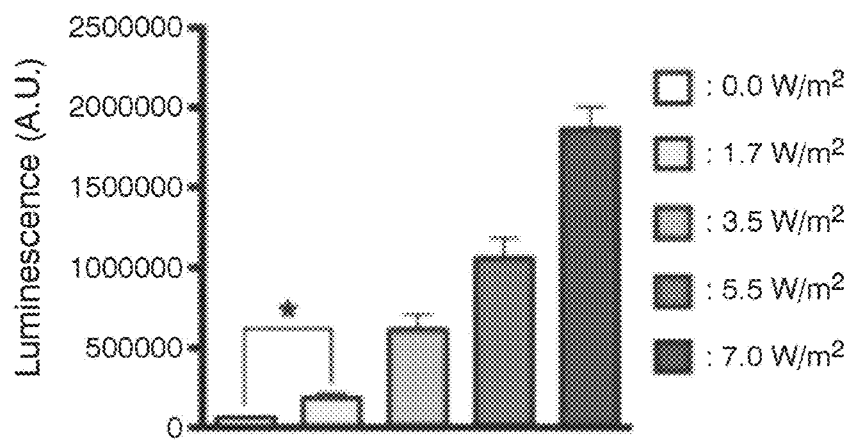
FIG. 9 is a view showing the results of investigating blue light intensity-dependent transcriptional activity of the PA-Tet-OFF system in Eph4 cells stably transduced with a lentiviral vector in Example 4.
Figure 10:
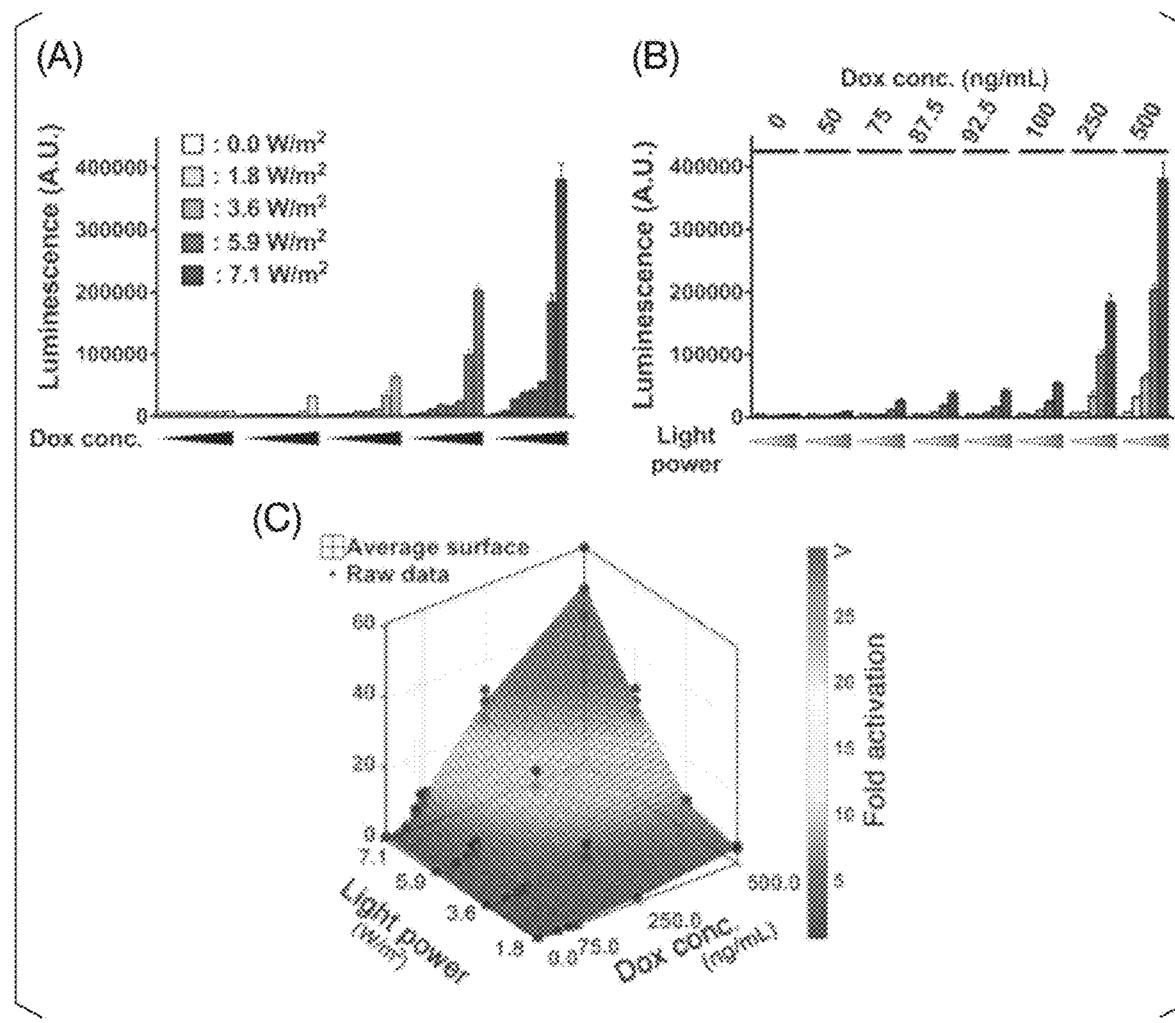
FIG. 10 is a view showing the results of investigating blue light intensity dependence and the Dox concentration dependence of the PA-Tet-ON system in Eph4 cells stably transduced with a lentiviral vector in Example 4.

FIG. 9 shows the results of investigating the blue light intensity dependence of the transcriptional activity of the PA-Tet-OFF system stable strain. FIG. 10 shows the results of investigating the blue light intensity dependence and the Dox concentration dependence of the transcriptional activity of the PA-Tet-ON system stable strain. The radiant energy was varied in a range of 0 to 7.1 W/m$^2$. The Dox concentration was varied in a range of 0 to 500 ng/mL. The data in both drawings represent the mean±standard deviation (n=3) obtained from one experiment. It was confirmed that the transcriptional activity increases in a light intensity-dependent manner in all the stable strains, and the expression is induced in a light intensity-dependent manner. In addition, it was confirmed that in the PA-Tet-ON system stable strain, the expression was induced in a Dox concentration-dependent manner. As is evident from the results in FIG. 10, particularly, as is evident from FIG. 10(C), in a case where the PA-Tet-ON system is used, by appropriately adjusting the blue light intensity and the concentration of a Tet-based compound, it is possible to adjust the transcriptional activity of a target gene to a desired level. That is, in the PA-Tet-OFF/ON system, gene expression can be controlled by both the light intensity and the concentration of a Tet-based compound, which indicates that the PA-Tet-OFF/ON system is useful especially for various biological experiments in which a gene expression level needs to be strictly controlled.

Next, the PA-Tet-ON system stable strain was irradiated with blue light (pulsed light) once a day for 6 days, and Dox (1,000 ng/mL) was added to the medium only on the 1st, 3rd, and 5th days. The timing of exposure to blue light (arrowhead) and the timing of adding Dox to the medium are shown in the upper part of FIG. 11, and the transcriptional activity (luminescence signal intensity) of the PA-Tet-ON system stable strain is shown in the lower part of FIG. 11.

Figure 11:
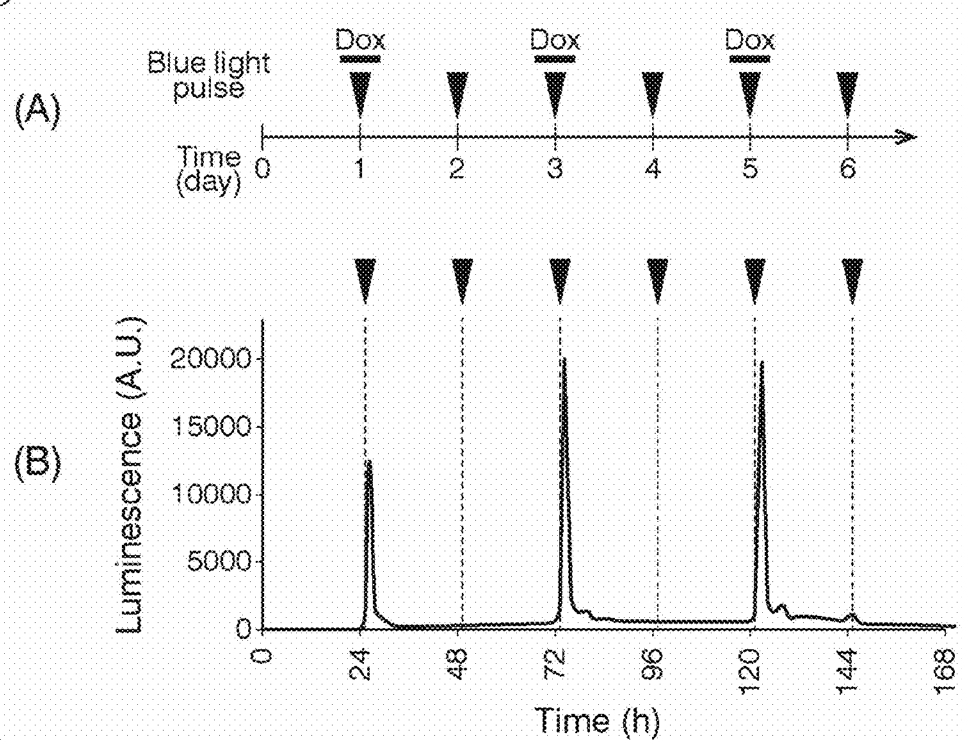
FIG. 11 is a view showing the experiment results obtained by irradiating the PA-Tet-ON system stable strain with blue light once a day for 6 days and adding Dox (1,000 ng/mL) to the medium only on the 1st, 3rd, and 5th days in Example 4, in which the timing of exposure to blue light is indicated by arrowheads, the timing of adding Dox to the medium is shown in the upper part, and the measured transcriptional activity (luminescence signal intensity) of the PA-Tet-ON system stable strain is shown in the lower part.

Most of PA-Tet-controlled gene expression systems are activated by a small amount of light, and the transcriptional activity is sufficiently activated by short exposure to indoor lighting (Non-Patent Literatures 2, 13, and 25). Therefore, the cells containing the PA-Tet-controlled gene expression system should be kept in absolute darkness or under a special red or far-red lighting device. In addition, before being subjected to a light irradiation experiment, the cells should be prepared under dark conditions for hours or days in some cases. In contrast, the light-dependent activity of the PA-Tet-OFF/ON system can be conditionally induced by exposure to a Tet-based compound or washing the Tet-based compound off. For example, in PA-Tet-ON system stable strain, light-dependent gene expression did not persist in the absence of Dox (FIG. 11). In contrast, by the introduction of Dox immediately before the blue light irradiation, light-dependent gene expression could be induced during one week of experiment (FIG. 11). In this way, the control by a Tet-based compound in the PA-Tet-OFF/ON system makes it possible to prevent unwanted gene induction especially in long-term experiments.

Example 5

Cry2 is rapidly activated by light irradiation and spontaneously dissociates from CIB1 with a half-life of about 5.5 minutes (Non-Patent Literature 9 and Non-Patent Literature 11). The dynamics of rapid activation and inactivation of the Cry2/CIB1 system can result in dynamic change of target gene expression positioned downstream of the PA-Tet-OFF/ON system, such as periodic oscillation or stepwise increase of gene expression patterns. Therefore, by irradiating the PA-Tet-OFF/ON system stable strain with short pulsed light (1 or 2 minutes) and monitoring the luciferase expression level under the control of the TRE sequence in real time, the temporal characteristics of the PA-Tet-OFF/ON system were verified.

As the PA-Tet-OFF system stable strain, 2 strains, the PA-Tet-OFF system stable strain prepared in Example 4 (using a TRE3G-Ub-NLS-luc2-Hes1 3'UTR lentiviral vector as a reporter construct, hereinafter, called "PA-Tet-OFF stable strain (Ub-NLS-luc2 reporter)" in some cases)) and a PA-Tet-OFF system stable strain (hereinafter, called "PA-Tet-OFF stable strain (luc2 reporter)" in some cases)) obtained by transducing Eph4 cells with the PA-Tet-OFF construct described in FIG. 8(A) and TRE3G-luc2-Hes1 3'UTR lentiviral vector, were used. Similarly, as the PA-Tet-ON system stable strain, 2 strains, the PA-Tet-ON system stable strain prepared in Example 4 (using a TRE3G-Ub-NLS-luc2-Hes1 3'UTR lentiviral vector as a reporter construct, hereinafter, called "PA-Tet-ON stable strain (Ub-NLS-luc2 reporter)" in some cases)) and a PA-Tet-ON system stable strain (hereinafter, called "PA-Tet-ON stable strain (luc2 reporter)" in some cases)) obtained by transducing Eph4 cells with the PA-Tet-ON construct described in FIG. 8(A) and the TRE3G-luc2-Hes1 3'UTR lentiviral vector, were used.

Figure 12:
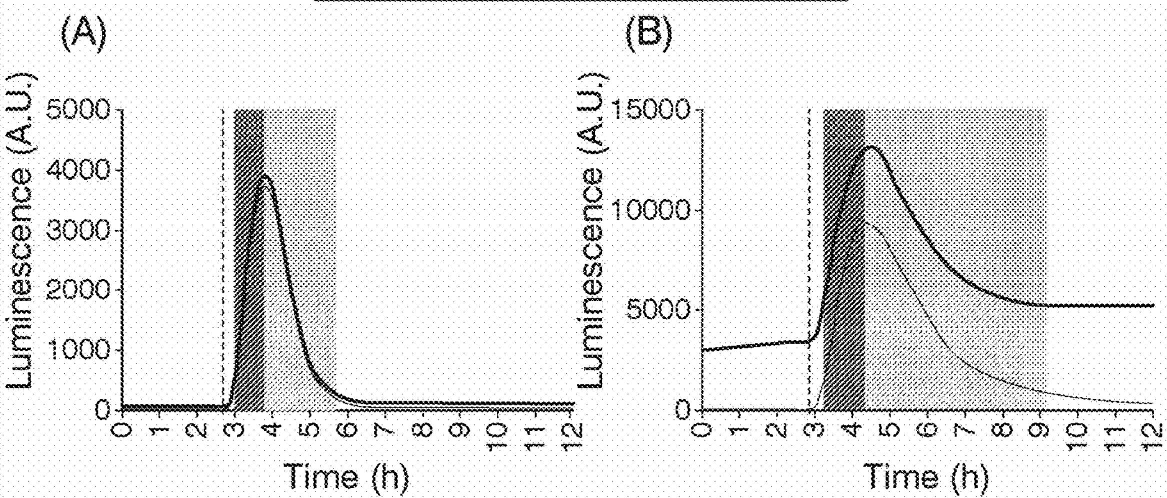
FIG. 12 is a view showing the results obtained in Example 5 by irradiating a PA-Tet-OFF stable strain (Ub-NLS-luc2 reporter) (A) and a PA-Tet-OFF stable strain (luc2 reporter) (B) with blue light pulses and monitoring the luminescence signal intensity in real time.

Each of the PA-Tet-OFF/ON system stable strains was irradiated with short blue light pulses (for 1 or 2 minutes), and the luminescence signal intensity was monitored in real time. FIG. 12(A) shows the results obtained from the PA-Tet-OFF stable strain (Ub-NLS-luc2 reporter), and FIG. 12(B) shows the results obtained from the PA-Tet-OFF stable strain (luc2 reporter). In FIGS. 12(A) and 12(B), the vertical dotted line represents a point in time when the cells were irradiated with the pulsed light. The period from when the blue light irradiation was started to when the luminescence signal intensity reached a peak was adopted as on-phase, and the period from when the luminescence signal intensity reached a peak to when the luminescence signal intensity returned to the level exhibited before the blue light irradiation was adopted as off-phase. As shown in FIG. 12(A), in the PA-Tet-OFF stable strain (Ub-NLS-luc2 reporter), the blue light pulse-induced luciferase activity was observed about 1.1 hours after the irradiation with blue light pulses and then returned to the background level within 3 hours. In addition, before the blue light irradiation, substantially no luminescence signal was observed. On the other hand, in the PA-Tet-OFF stable strain (luc2 reporter), luminescence signals were observed before the blue light irradiation, and both the on-phase and the off-phase were longer than in the PA-Tet-OFF stable strain (Ub-NLS-luc2 reporter) (FIG. 12(B)).

For each of the PA-Tet-OFF/ON system stable strains, the half-life of the switch-on/off reaction rates of PA-Tet-controlled gene expression in the PA-Tet-OFF/ON system was determined by kymograph analysis based on the luminescence signal intensity monitoring results. FIG. 13(A) shows the results of the half-life of the switch-on reaction rate, and FIG. 13(B) shows the results of the half-life of the switch-off reaction rate. The data represent mean±standard deviation (n=3). In FIGS. 13(A) and 13(B), "*" means $p<0.05$ (paired student's t-test).

Figure 13:
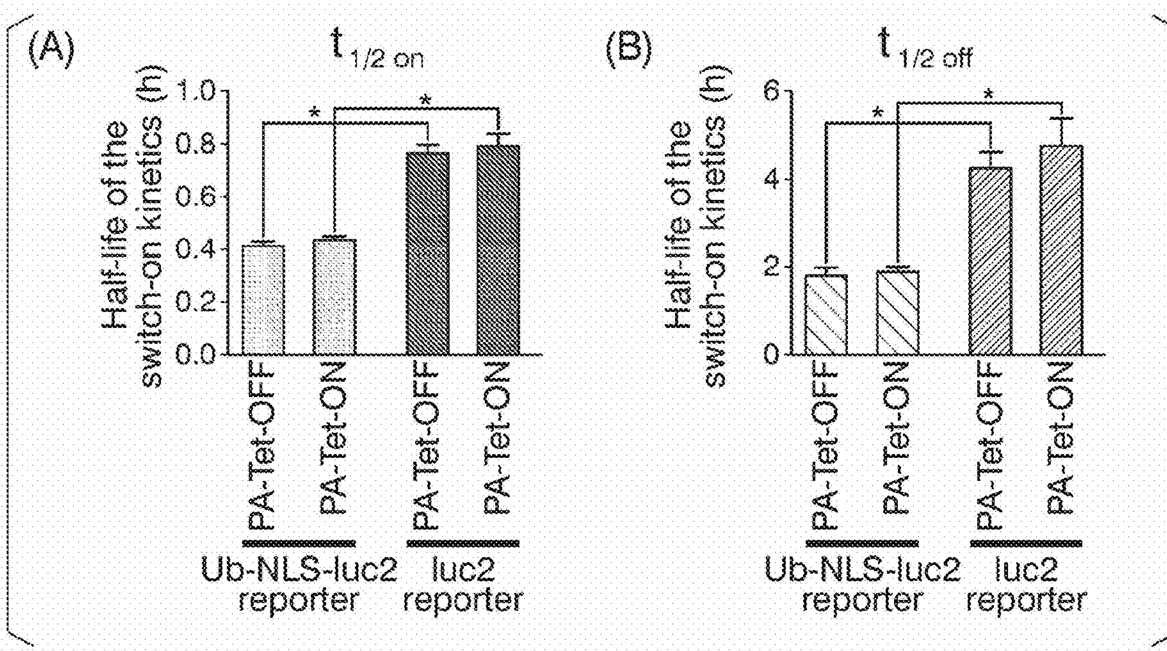
FIG. 13 is a view showing the results obtained in Example 5 by measuring the half-life of a switch-on reaction rate (A) and the half-life of a switch-off reaction rate (B) of PA-Tet-controlled gene expression in a PA-Tet-OFF/ON system in PA-Tet-OFF/ON system stable strains.
Figure 14:
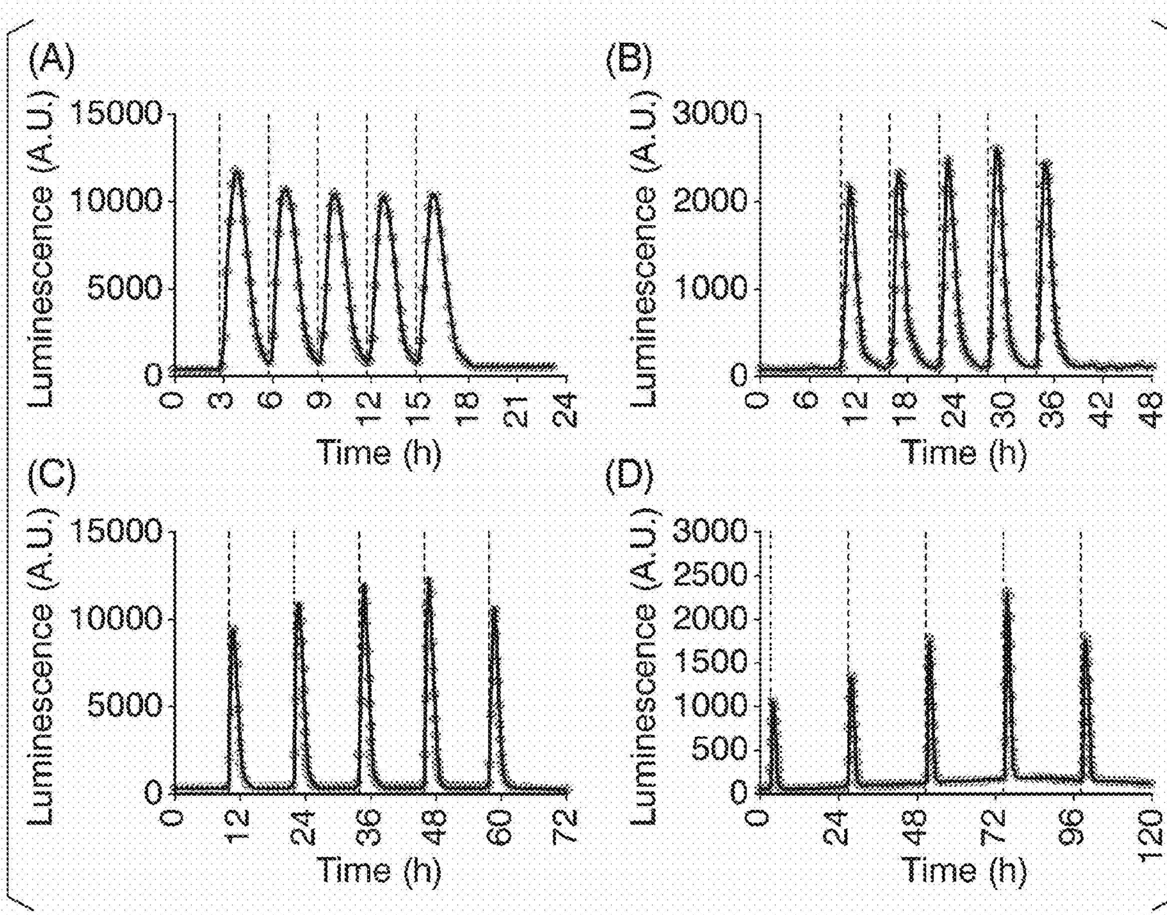
FIG. 14 is a view showing the results obtained in Example 5 by repeatedly exposing the PA-Tet-OFF stable strain (Ub-NLS-luc2 reporter) to blue light pulses at intervals of 3 hours (A), 6 hours (B), 12 hours (C), and 24 hours (D) and monitoring the luminescence signal intensity in real time.

The PA-Tet-OFF stable strain (Ub-NLS-luc2 reporter) was repeatedly exposed to blue light pulses at intervals of 3 hours (FIG. 14(A)), 6 hours (FIG. 14(B)), 12 hours (FIG. 14(C)), and 24 hours (FIG. 14(D)), and the luminescence signal intensity was monitored in real time. In FIGS. 14(A) to 14(D), the point in time when the cells were irradiated with blue light pulses is represented by a vertical dotted line. The experiment was repeated at least 3 times to obtain consistent results. As a result, the periodic exposure to the blue light pulses induced strong oscillatory expression at the same period as that of the blue light pulses. Even though the cells were periodically irradiated with blue light pulses at extremely short intervals, such as 3 hours, the accumulation of the Ub-NLS-luc2 reporter was not observed, because the destabilized luciferase reporter having the 3'UTR sequence has a short half-life. This result indicates that a reporter having a short half-life is essential for generating this short ultradian rhythm. In contrast, a normal and stable luciferase reporter is likely to be suitable for longer-term periodic gene expression experiments that mimic the expression of typical clock genes over circadian rhythms. In reality, as shown in FIG. 13, in a PA-Tet-OFF/ON stable strain (luc2 reporter) using a reporter construct exploiting normal and stable luciferase, the half-life of the switch-on/off reaction rate of PA-Tet-controlled gene expression was extended.

Example 6

Another great advantage of photocontrolled systems is the ability to spatially limit the gene expression in target cells. Therefore, the PA-Tet-OFF stable strain (Ub-NLS-luc2 reporter) was used to investigate the ability to spatially limit the gene expression. In order to investigate the spatially limited gene expression in target cells, a bioluminescence imaging microscope equipped with a digital mirror device (DMD) for generating spatial patterns of light was used.

Figure 15:
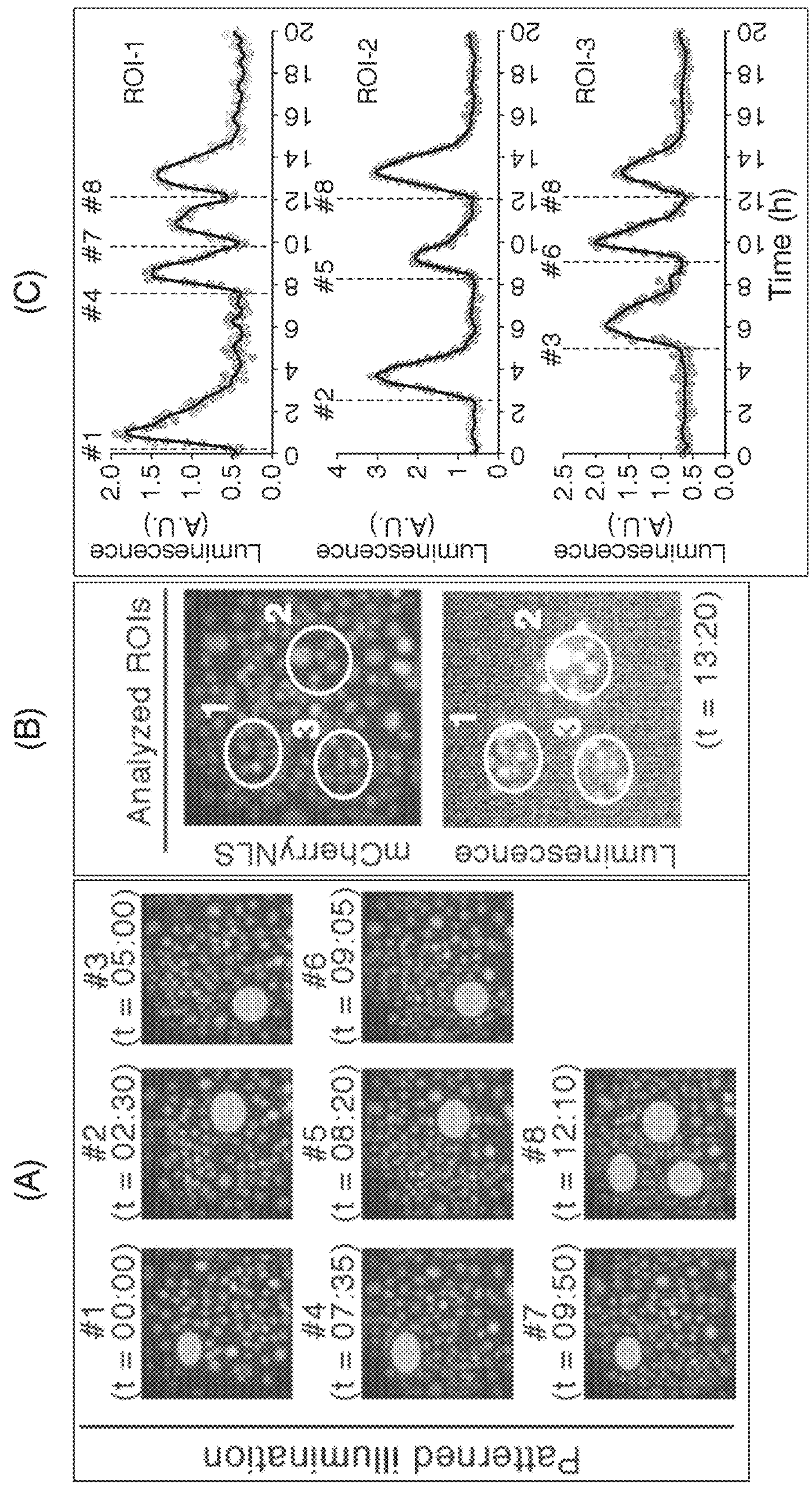
FIG. 15 is a view showing irradiation regions and irradiation timing of patterned blue light radiated to the PA-Tet-OFF stable strain (Ub-NLS-luc2 reporter) in Example 6.

A population of PA-Tet-OFF stable strain (Ub-NLS-luc2 reporter) was installed in a bioluminescent imaging microscope with DMD and irradiated with patterned light generated by DMD. Specifically, different round cell populations were sequentially activated at different timing. FIG. 15(A)

shows the region of the PA-Tet-OFF stable strain (Ub-NLS-luc2 reporter) irradiated with the patterned blue light and the irradiation timing. In FIG. 15(A), "t" in each cell image represents the elapsed time (hour and minute) from the start of the experiment, and the region in a white circle represents the region irradiated with blue light at the time point. The patterned light was radiated to three regions of interest (ROI-1 to ROI-3) at different timing. That is, ROI-1 was irradiated with light 0 minutes (#1), 7 hours and 35 minutes (#4), 9 hours and 50 minutes (#7), and 12 hours and 10 minutes (#8) after the start of the experiment. ROI-2 was irradiated with light 2 hours and 30 minutes (#2), 8 hours and 20 minutes (#5), and 12 hours and 10 minutes (#8) after the start of the irradiation. ROI-3 was irradiated with light 5 hours (#3), 9 hours and 5 minutes (#6), and 12 hours and 10 minutes (#8) after the start of the irradiation.

FIG. 15(B) shows images of mCherry fluorescence signals (upper image) and luminescence signals (lower image) occurring in each region of interest 13 hours and 20 minutes after the start of irradiation. In addition, FIG. 15(C) shows the results of monitoring the luminescence signal intensity in each region of interest. The point in time when the cells were irradiated with blue light pulses is represented by the vertical dotted line. As shown in FIG. 15(B), PA-Tet-controlled luciferase expression was observed only in cells included in ROI-1 to ROI-3 irradiated with the blue light pulses. Furthermore, as shown in FIG. 15(C), PA-Tet-controlled luciferase expression was observed at the timing at which the cells were irradiated with blue light pulses.

Figure 16:
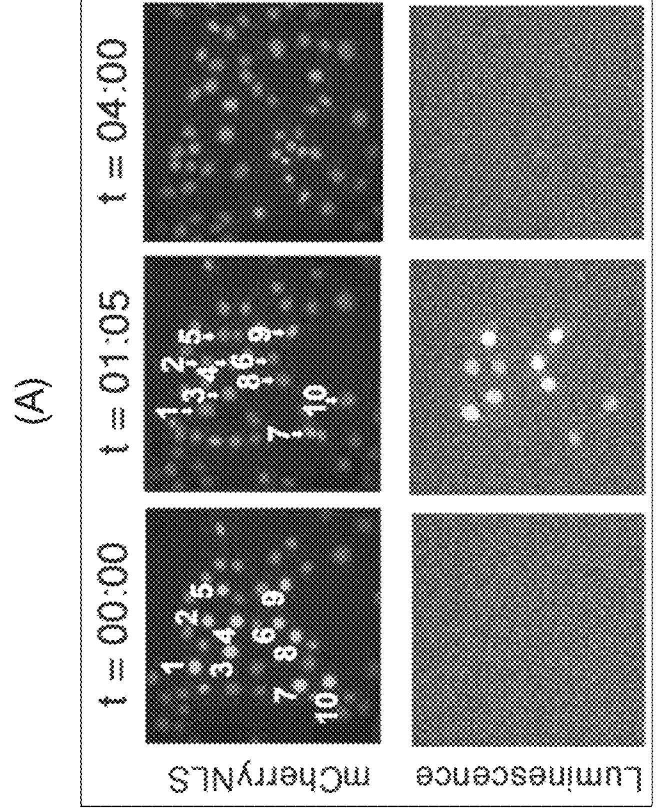
FIG. 16(A) shows mCherry fluorescence images and bioluminescence images of 10 target cells irradiated with blue light pulses in Example 6.
FIG. 16(B) is a view showing the result of monitoring luminescence signal intensity of the target cells and unirradiated cells in Example 6.

Next, only 10 target cells (cells represented by "1" to "10" in FIG. 16(A)) were simultaneously irradiated with blue light pulses, and the light-induced reporter expression in these cells was monitored. In FIG. 16(A), "t" represents the elapsed time (hours and minutes) from the pulse irradiation, the left images show the signals observed 0 minutes after the pulse irradiation, the middle images show signals observed 1 hour and 5 minutes after the pulse irradiation, and the right images show signals observed 4 hours after the pulse irradiation. One hour and five minutes after the blue light pulse irradiation, PA-Tet-controlled luciferase expression was observed only in the 10 target cells irradiated with blue light, and the expression of luciferase was not induced in the adjacent unirradiated cells. In addition, after 4 hours, the PA-Tet-controlled luciferase expression was terminated in all target cells.

For 9 cells among the irradiated target cells except for the target cell 9, the luminescence signal intensity was quantified and averaged. In the target cell 9, cell division occurred during the time-lapse imaging experiment. Therefore, this cell was excluded in averaging the luminescence signal intensity. Similarly, from the unirradiated cells adjacent to the target cells, 9 cells were randomly selected, and the luminescence signal intensity thereof was quantified and averaged. The results are shown in FIG. 16(B). The data represent mean±standard deviation obtained from one experiment. In FIG. 16(B), the solid line represents the average, and the region surrounded by the dotted line is a range of mean±standard deviation. The experiment was repeated at least 3 times to obtain consistent results. From these results, it was confirmed that with the PA-Tet-OFF/ON system, by strictly controlling the region to be irradiated with light, it is possible to induce the expression of a target gene only in cells within a limited space.

Example 7

The PA-Tet-OFF/ON system was verified in a developing mouse brain and an adult mouse brain.

Figure 17:
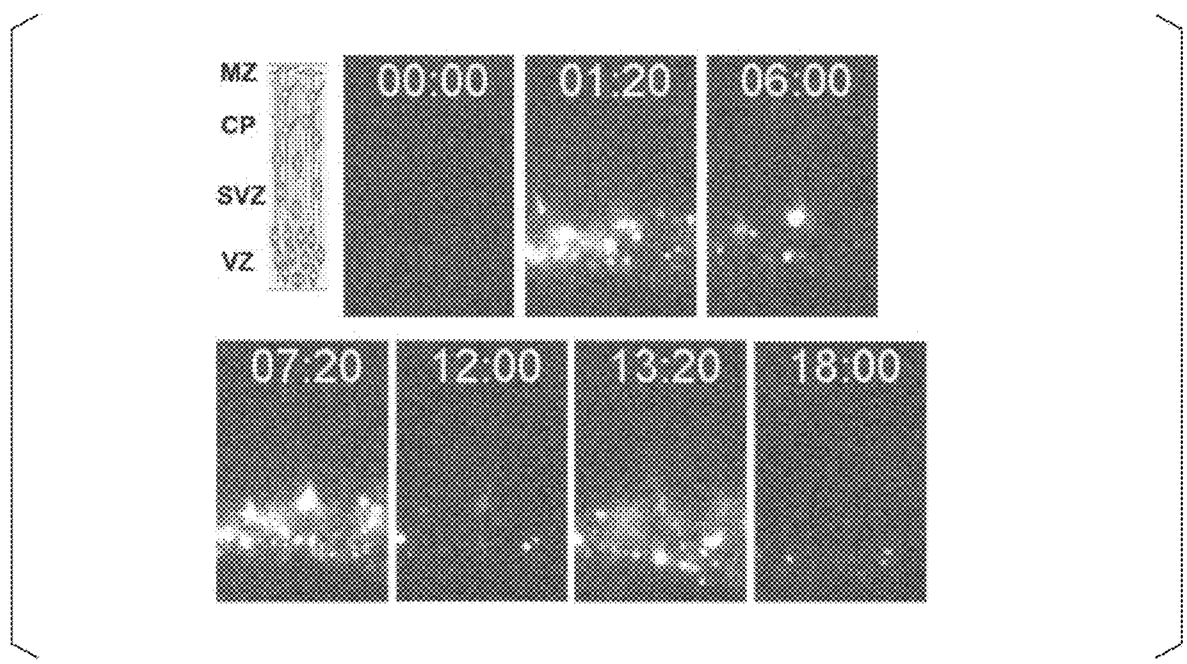
FIG. 17 shows luminescence signal images of slices of a developing mouse brain that underwent the introduction of a PA-Tet-OFF system and was periodically irradiated with blue light at intervals of 6 hours in Example 7.
Figure 18:
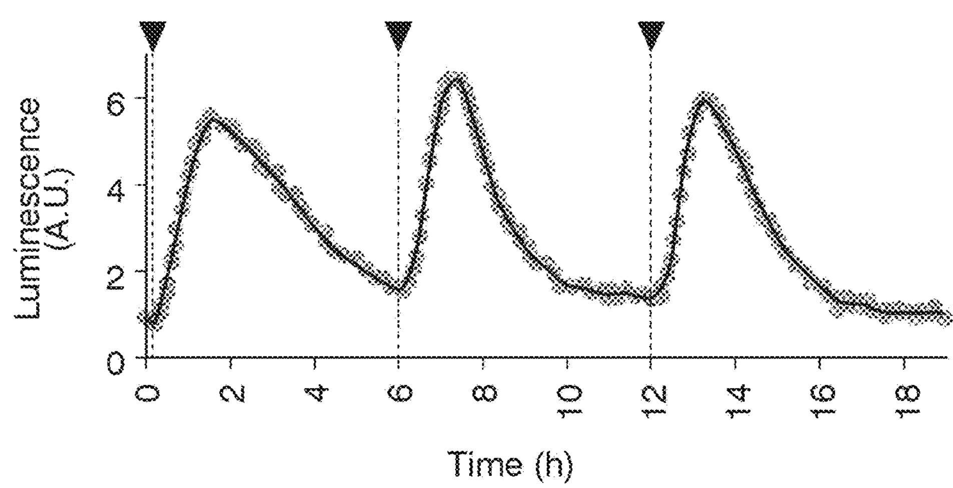
FIG. 18 is a view showing the results of real-time monitoring of the luminescence signal intensity of slices of a developing mouse brain that underwent the introduction of a PA-Tet-OFF system and was periodically irradiated with blue light at intervals of 6 hours in Example 7.

(1) Verification of PA-Tet-OFF System in Neural Stem/Progenitor Cells of Developing Mouse Brain By ex utero electroporation, the PA-Tet-OFF system was introduced into neural stem/progenitor cells of a developing mouse brain. The electroporated brain was immediately extracted from the embryo, cut into slices, and placed on a thin film for tissue culture. The slices were periodically irradiated with blue light at intervals of 6 hours, and the reporter activity was monitored. FIG. 17 shows images of luminescence signals generated by the luciferase expression in the slices (MZ: marginal zone, CP: cortical plate, VZ: ventricle, SVZ: subventricular zone). FIG. 18 shows the results of real-time monitoring of the luminescence signal intensity of the slices. In FIG. 18, the point in time when the cells were irradiated with blue light pulses is represented by a vertical dotted line. One hour and twenty minutes after the blue light irradiation, that is, 1 hour and 20 minutes, 7 hours and 20 minutes, and 13 hours and 20 minutes after the start of the blue light irradiation, PA-Tet-controlled luciferase expression that appeared blue was observed in the neural stem/progenitor cells in VZ and SVZ (FIG. 17). VZ and SVZ are regions where neural stem/progenitor cells are divided to produce neurons. All experiments were performed in two independent trials to obtain consistent results.

(2) Verification of PA-Tet-OFF System in Primary Cultured Neurons Derived from Hippocampus of Mouse Pups By using the AAV vector, the PA-Tet-OFF system was introduced into differentiated neurons.

Figure 19:
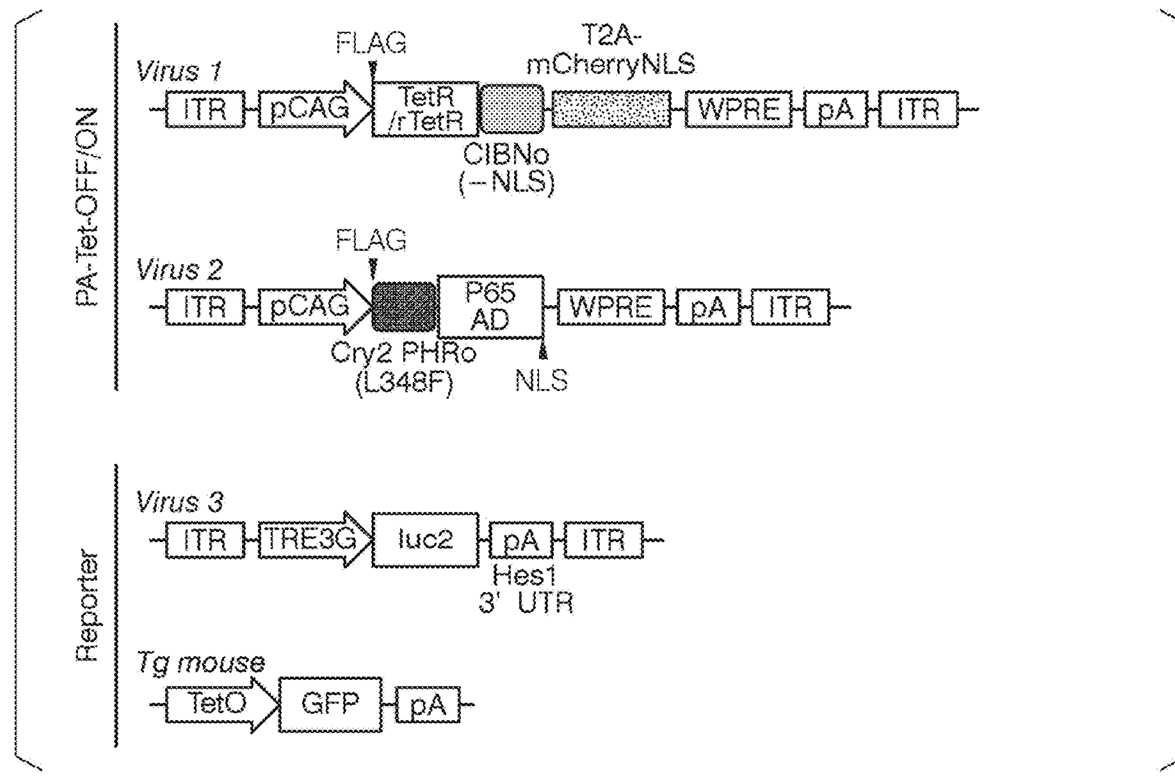
FIG. 19 is view schematically showing two constructs used in Example 7 for the introduction of the PA-Tet-OFF/ON system, a CAG-FLAG-TetR (or rTetR)-CIBN (-NLS)-T2A-mCherryNLS construct ("Virus 1" in FIG. 19) and a CAG-NLS-attached Cry2 PHR (L348F)-p65 ADN-terminal fusion construct ("Virus 2" in FIG. 19), and two reporters, a TRE3G-Ub-NLS-luc2-Hes1 3'UTR reporter ("Virus 3" in FIG. 19) and a reporter expressed in the TetO-GFP transgenic reporter mouse strain ("Tg mouse" in FIG. 19)).

FIG. 19 is a view schematically showing 2 constructs used for introduction of the PA-Tet-OFF/ON system, which are a CAG-FLAG-TetR (or rTetR)-CIBN (-NLS)-T2A-mCherryNLS construct ("Virus 1" in FIG. 19) (SEQ ID NO: 18) and a CAG-NLS-attached Cry2 PHR (L348F)-p65AD N-terminal fusion construct ("Virus 2" in FIG. 19) (SEQ ID NO: 19). FIG. 19 also schematically shows a TRE3G-Ub-NLS-luc2-Hes1 3'UTR reporter ("Virus 3" in FIG. 19) (SEQ ID NO: 20) and a TetO-GFP reporter ("Tg mouse" in FIG. 19) (Non-Patent Literature 26) expressed in a TetO-GFP transgenic reporter mouse strain. As "TetR (or rTetR)" in "Virus 1" construct in FIG. 19, TetR (I194T, 1-206) was used in the PA-Tet-OFF system, and rTetR (I194T, 1-206) was used in the PA-Tet-ON system.

First, mouse hippocampus-derived neurons that had been primary cultured for 3 days were transduced with an AAV vector expressing the Virus 1 construct and an AAV vector expressing the Virus 2 construct, and the obtained AAV-transformed neurons were subjected to immunofluorescence staining by using anti-Microtubule Associated Protein 2 (MAP2) antibodies. In most MAP2-positive neurons, fluorescence of the transduction marker mCherry was observed. Therefore, the neurons were confirmed to be transduced with the introduced AAV vectors.

Next, the mouse hippocampus-derived neurons that had been primary cultured for 3 days were transduced with an AAV vector expressing the Virus 1 construct and an AAV vector expressing the Virus 2 construct. Furthermore, on the 7th day of the primary culture, the neurons were transduced with the Virus 3 reporter lentivirus. Then, on the 20th day of the primary culture, the neurons were periodically irradiated with blue light pulses every 3 hours, and the fluorescence signals generated by the luciferase expression were investigated to monitor the reporter activity. Dox (500 ng/mL) was added to the transformed neurons transfected with the PA-Tet-ON system construct, and then the neurons were periodically irradiated with blue light pulses every 3 hours.

Figure 20:
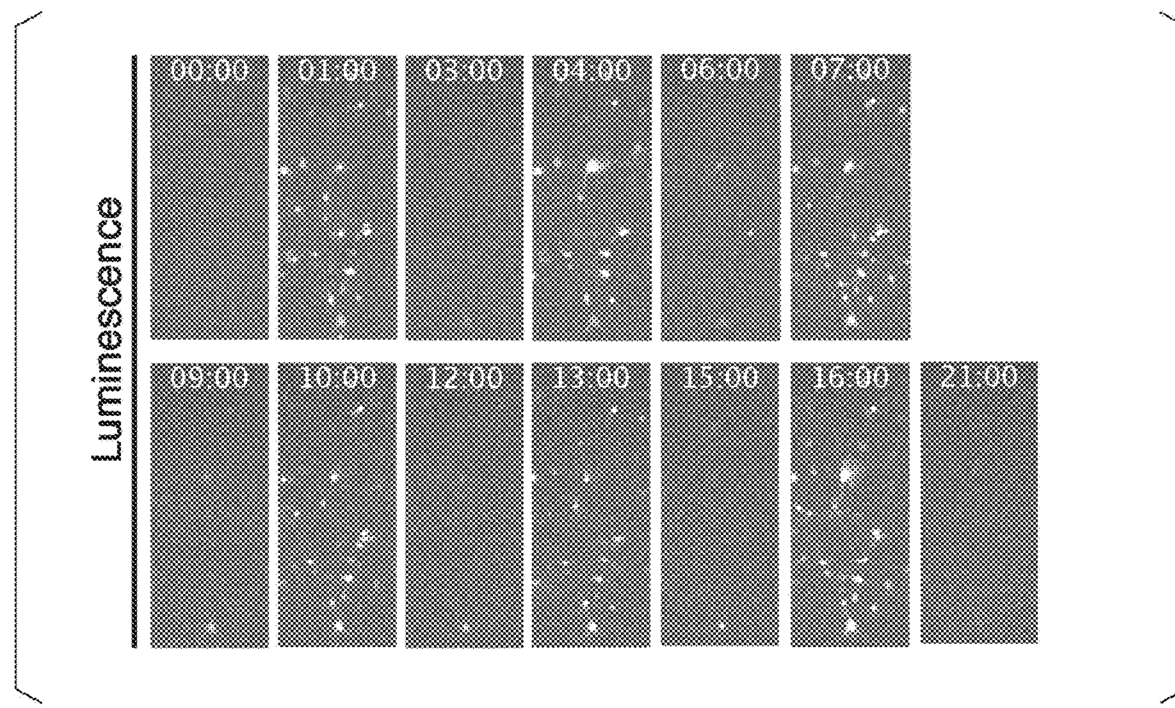
FIG. 20 shows images of luminescence signals generated due to the luciferase expression in transformed neurons transfected with the construct of the PA-Tet-OFF system in Example 7, in which the images show luminescence signals observed for 21 hours from the start of blue light pulse irradiation (0 hours).
Figure 21:
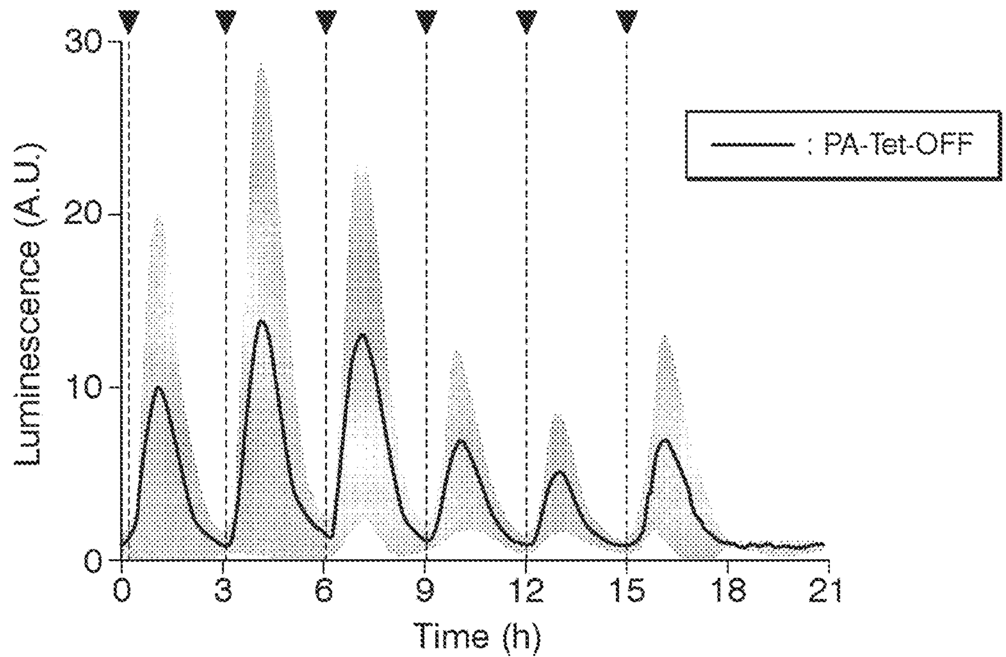
FIG. 21 is a view showing the results of measuring the luminescence signal intensity over time that was induced by luciferase expression in transformed neurons transfected with the construct of a PA-Tet-OFF system was in Example 7.
Figure 22:
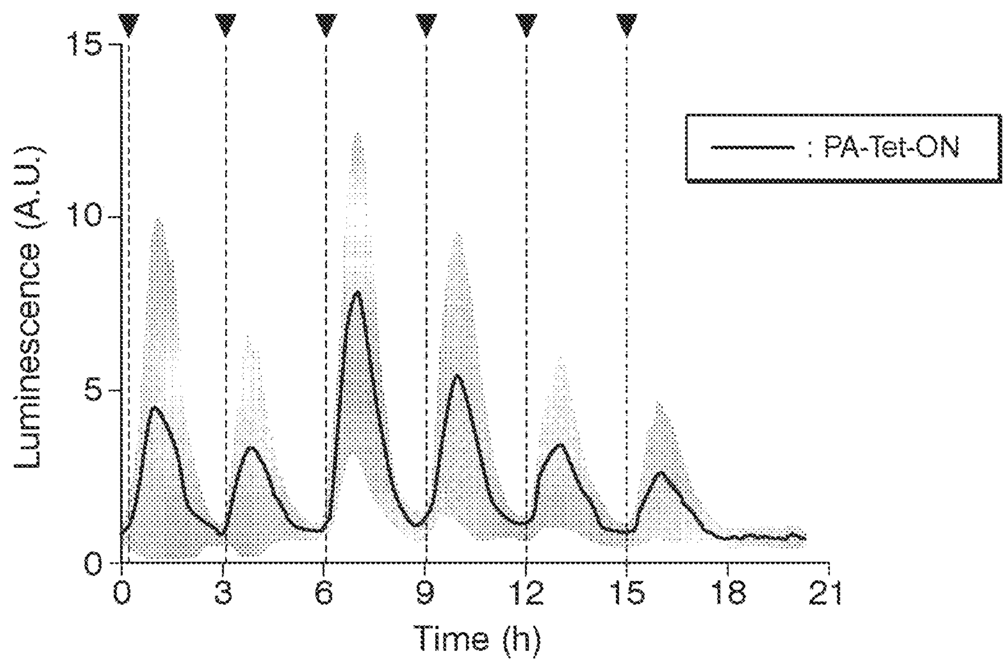
FIG. 22 is a view showing the results of measuring the luminescence signal intensity over time that was induced by luciferase expression in transformed neurons transfected with the construct of a PA-Tet-ON system in Example 7.

FIG. 20 shows images of luminescence signals generated by the luciferase expression in the transformed neurons transfected with the construct of the PA-Tet-OFF system. The images show luminescence signals observed for 21 hours from the start of the blue light pulse irradiation (0 hours). In addition, FIG. 21 shows the results of measuring the luminescence signal intensity over time that was induced by luciferase expression in transformed neurons transfected with the construct of the PA-Tet-OFF system. FIG. 22 shows the results of measuring the luminescence signal intensity over time that was induced in the presence of Dox by luciferase expression in transformed neurons transfected with the construct of the PA-Tet-ON system. In FIGS. 21 and 22, the timing of blue light pulse irradiation is indicated by arrowheads. All experiments were performed in two independent trials to obtain consistent results. As a result, it was confirmed that even in primary cultured cells, it is possible to control the expression of exogenous genes by light irradiation and Dox by means of transducing the cells with the PA-Tet-OFF/ON system.

(3) Verification of PA-Tet-OFF System in Adult Brain Neurons

By using the AAV vector, the PA-Tet-OFF system was introduced into differentiated neurons.

Figure 23:
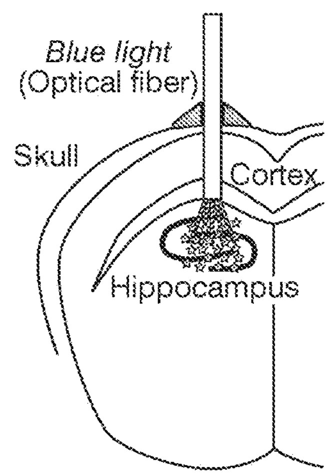
FIG. 23 is a view schematically showing the way the blue light is radiated to hippocampal neurons of an adult TRE-GFP transgenic mouse brain transfected with a PA-Tet-OFF system in Example 7.
Figure 24:
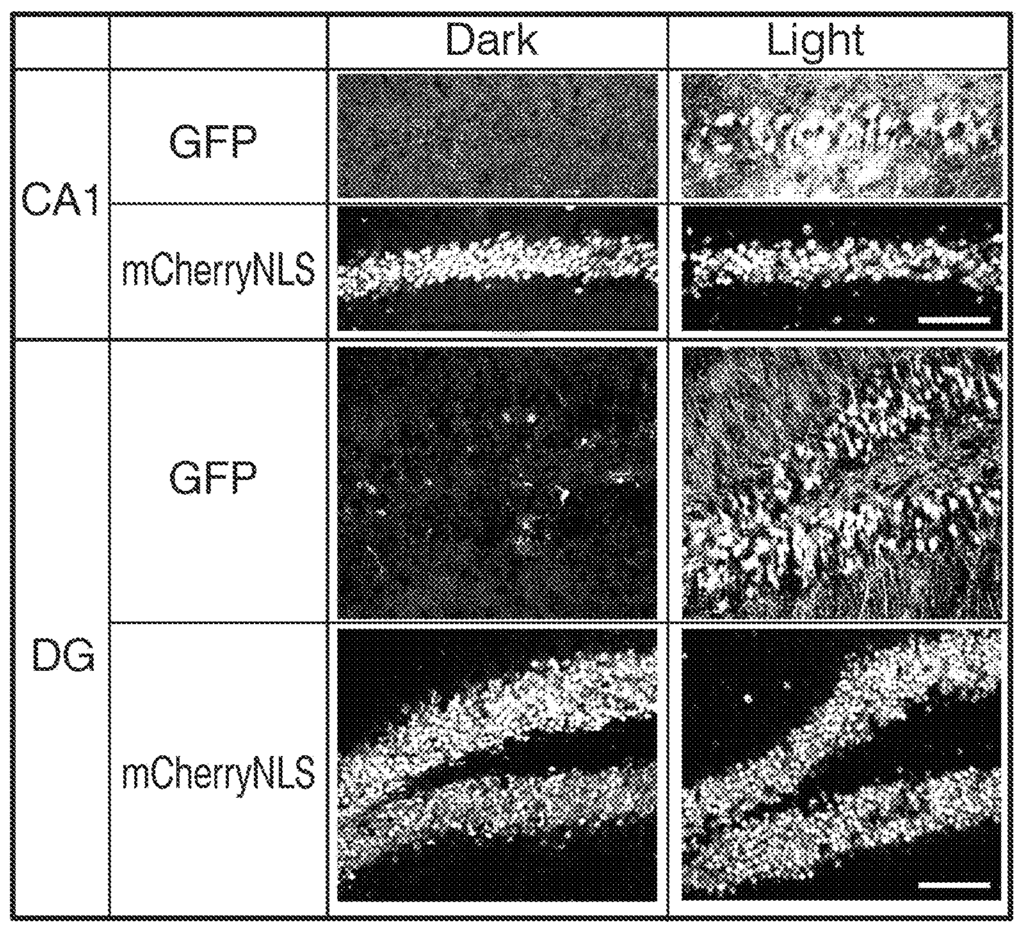
FIG. 24 shows fluorescence images obtained by irradiating the mouse brain with blue light in Example 7 by the method illustrated in FIG. 23 and then imaging the brain 12 hours after the start of exposure to the blue light, in which the images in the left column ("Dark") show the region not being irradiated with the blue light, and the images in the right column ("Light") show the region irradiated with the blue light.

FIGS. 23 and 24 show the results of transducing the hippocampus of a TRE-GFP transgenic mouse (Non-Patent Literature 26) with an AAV vector expressing the Virus 1 construct and an AAV vector expressing the Virus 2 construct. FIG. 23 is a view schematically showing the way the blue light is radiated to hippocampal neurons after the AAV transduction. FIG. 24 shows fluorescence images captured 12 hours after the start of exposure to blue light. In FIG. 24, the images in the left column ("Dark") show the region of brain not being irradiated with the blue light, and the images in the right column ("Light") show the region of brain irradiated with the blue light (scale bar: 100 μm). In neurons of the hippocampus (CA1) and dentate gyrus (DG) regions, GFP reporter expression increased in a blue light-dependent manner. In the hippocampus irradiated with blue light, 42.8±2.3% of hippocampal neurons and 36.7±6.0% of dentate gyrus granule cells expressed GFP. In contrast, under dark conditions, only 4.7±1.4% of hippocampal neurons and 4.4±1.6% of dentate gyrus neurons expressed GFP.

Figure 25:
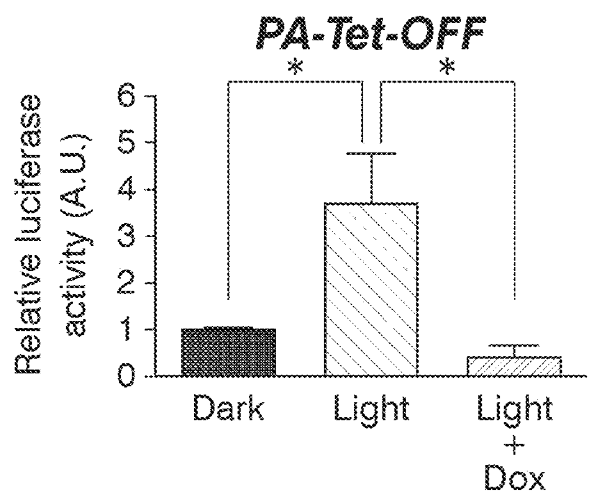
FIG. 25 is a view showing the results of measuring the luminescence signal intensity induced by luciferase expression in brain neurons of mouse pups transfected with the PA-Tet-OFF system in Example 7 and then subjected to a blue light pulse irradiation treatment.

Next, Dox-dependent inhibition of transcriptional activity of the PA-Tet-OFF system in brain neurons was analyzed. Mice that had been subjected to AAV transduction within 1 day after birth were subjected to a blue light pulse irradiation treatment on the 12th to 15th day after birth. In the light irradiation treatment, the mCherry expression region in the brain of each mouse placed on and fixed to a custom-made stage was irradiated with blue light pulses for 3 hours at an irradiance of 40 $W/m^2$ and a duty cycle of 7.1% (pulsed for 1 second at 0.071 Hz). The luminescence signal intensity induced by the luciferase expression in the brain cells after the light irradiation treatment was measured. Furthermore, for mice treated with Dox (0.1 mg/g (body weight)) 1 hour before the light irradiation treatment, the luminescence signal intensity was also measured in the same manner. The measurement results are shown in FIG. 25. In the mouse brain neurons (represented by "Light" in FIG. 25) subjected to the light irradiation treatment, luciferase expression was activated, and the luminescence signal intensity increased. In contrast, in the brain neurons treated with Dox 1 hour before the light irradiation (represented by "Light+Dox" in FIG. 25), the luminescence signal intensity was substantially the same as the luminescence signal intensity in the brain neurons not being irradiated with light (represented by "Dark" in FIG. 25), that is, significantly attenuated to the background level.

Figure 26:
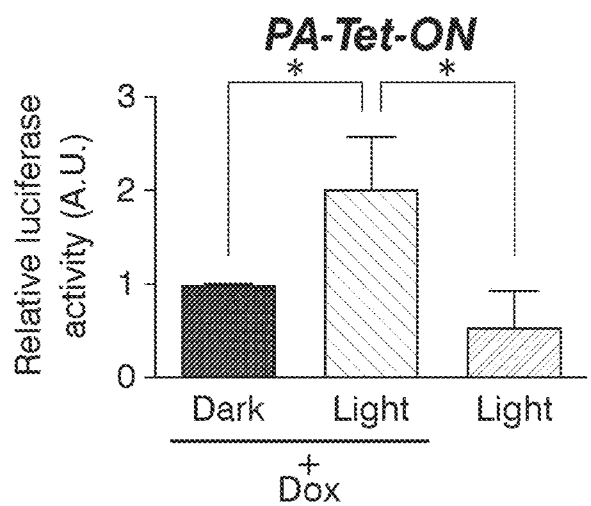
FIG. 26 is a view showing the results of measuring the luminescence signal intensity induced by luciferase expression in brain neurons of mouse pups transfected with the PA-Tet-ON system in Example 7 and then subjected to a blue light pulse irradiation treatment.

By using the construct of the PA-Tet-ON system, Dox-dependent inhibition of the transcriptional activity of the PA-Tet-ON system in brain neurons was analyzed in the same manner. The measurement results are shown in FIG. 26. In mouse brain neurons ("Light+Dox" in FIG. 26) subjected to the light irradiation treatment 1 hour after the Dox treatment (0.1 mg/g (body weight)), luciferase expression was activated, and the luminescence signal intensity increased. On the other hand, in the brain neurons that were subjected to the light irradiation treatment without the Dox treatment ("Light" in FIG. 26), the activation of luciferase expression was not observed as in the mouse brain neurons that were not subjected to the light irradiation treatment 1 hour after the Dox treatment ("Dark+Dox" in FIG. 26). That is, blue light-dependent transcription was observed only in the presence of Dox.

Figure 27:
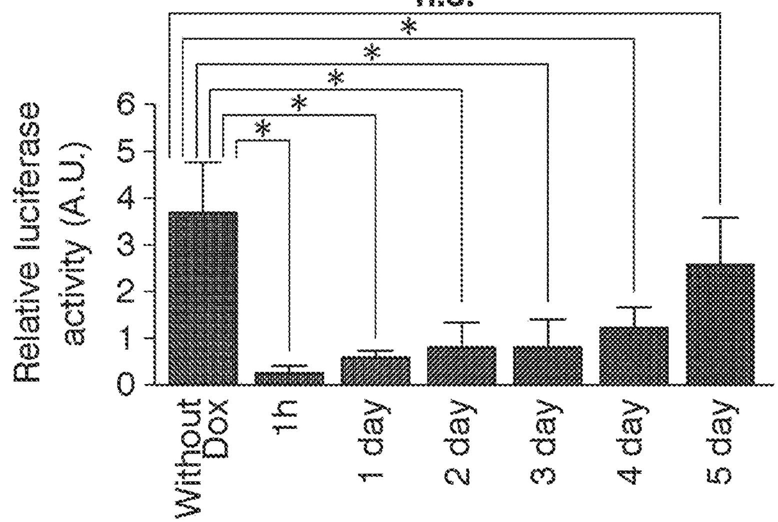
FIG. 27 is a view showing the results of measuring the luminescence signal intensity induced by luciferase expression in PA-Tet-OFF system-transfected brain neurons subjected to a blue light pulse irradiation treatment 1 hour, 1 day, 2 days, 3 days, 4 days, and 5 days after a Dox treatment in Example 7.

Furthermore, the restoration of light-inducible transcriptional activity after removal of Dox was analyzed in cells transfected with the PA-Tet-OFF system. Specifically, mice that had been subjected to AAV transduction within 1 day after birth were subjected to the Dox treatment (0.1 mg/g (body weight)) on the 12th to 15th day after birth. Then, the mice were subjected to a blue light pulse irradiation treatment 1 hour, 1 day, 2 days, 3 days, 4 days, and 5 days after the Dox treatment. The luminescence signal intensity induced by the luciferase expression in the brain cells after the light irradiation treatment was measured. The Dox treatment, the blue light pulse irradiation treatment, and the measurement of luminescence signal intensity induced by luciferase expression were carried out in the same manner as described above. The measurement results are shown in FIG. 27. The inhibition of light-induced luciferase expression persisted for 4 days after the single dosing of Dox, and on the 5th day, the luciferase reporter activity was restored substantially to the same level as the luciferase reporter activity in Dox-untreated cells. These results indicate that the PA-Tet-OFF/ON system is capable of controlling gene expression by both light and Tet even in vivo.

Example 8

The PA-Tet-OFF/ON system in the mouse subcutaneous tissue was verified.

First, the PA-Tet-OFF stable strain (Ub-NLS-luc2 reporter) (Eph4 cells stably transduced with the PA-Tet-OFF system by using a lentiviral vector) obtained in Example 4 was transplanted into the subcutaneous tissue of the dorsal skin of adult mice. A Dox treatment was performed 24 hours after cell transplantation, and 1 hour after the Dox treatment, a blue light irradiation treatment (200 $W/m^2$; 1 minute) was performed on the transplantation region of the dorsal skin of the anesthetized mice. After the blue light irradiation treatment, the mice were imaged with a CCD camera so that the dynamic change of luciferase signals was visualized.

Figure 28:
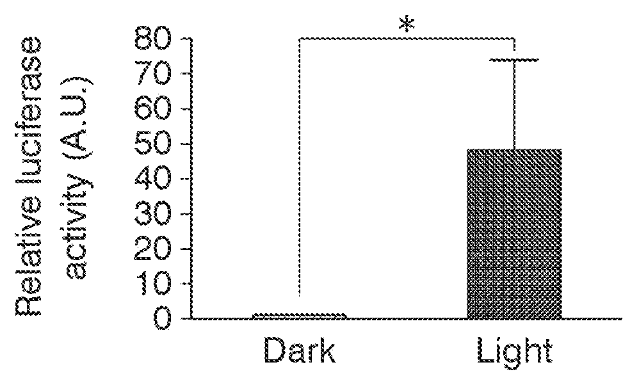
FIG. 28 is a view showing the results of measuring the luminescence signal intensity induced by luciferase expression in the subcutaneous tissue of the dorsal skin of an adult mouse transplanted with a PA-Tet-OFF stable strain (Ub-NLS-luc2 reporter) in Example 8, in which "Dark" represents the luminescence signal intensity obtained under dark conditions, and "Light" represent the luminescence signal intensity obtained after blue light irradiation.
Figure 29:
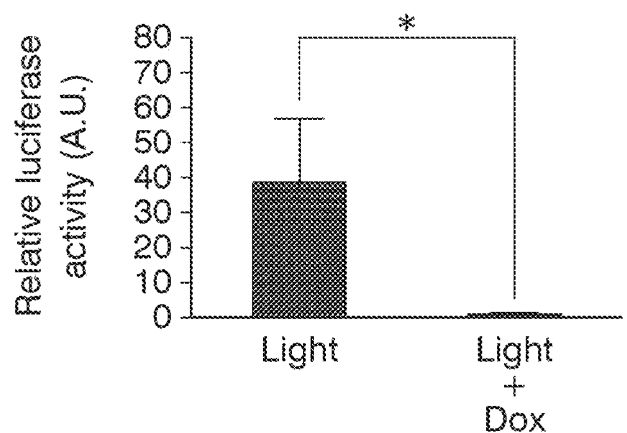
FIG. 29 is a view showing the results of measuring the luminescence signal intensity induced by luciferase expression in the subcutaneous tissue of the dorsal skin of an adult mouse transplanted with a PA-Tet-OFF stable strain (Ub-NLS-luc2 reporter) in Example 8, in which "Light" represents the luminescence signal intensity obtained after the blue light irradiation in the absence of Dox, and "Light+Dox" represents the luminescence signal intensity obtained after the blue light irradiation in the presence of Dox.

FIG. 28 shows the average of the luminescence signal intensity in the Dox-untreated subcutaneous tissue under dark conditions ("Dark" in FIG. 28) and the average of the luminescence signal intensity in the same tissue measured for 30 to 60 minutes after the blue light irradiation ("Light" in FIG. 28). Furthermore, FIG. 29 shows the average of the luminescence signal intensity measured in the Dox-untreated subcutaneous tissue ("Light" in FIG. 29) after the blue light irradiation and the average of the luminescence signal intensity measured in the Dox-treated subcutaneous tissue ("Light+Dox" in FIG. 29) after the blue light irradiation. As a result, it was confirmed that in the absence of Dox, the luciferase signals do not increase in the subcutaneous tissue under dark conditions but increase in the subcutaneous tissue irradiated with blue light (FIG. 28). In addition, the luciferase signals activated by blue light irradiation completely disappeared by the Dox treatment (FIG. 29). From these results, it was confirmed that the PA-Tet-OFF/ON system also functions in tissues including subcutaneous tissue other than the brain.

Example 9

As an attempt to construct a PA-Tet-OFF system that induces the expression of target genes by light irradiation and a Tet-based compound, a Bphp1/Q-PAS1-PA binding switch was incorporated into the Tet-OFF system. For constructing the system, HEK293T cells were used, and the PA-Tet gene expression system optimal for mammalian cells was investigated.

Specifically, a reporter plasmid (pTREtight-Ub-ELuc reporter), a plasmid containing an expression cassette for a fusion protein in which TetR is fused with one of Bphp1 and Q-PAS1, and a plasmid containing an expression cassette for a fusion protein in which p65AD protein is fused with the remaining other one of Bphp1 and Q-PAS1 were introduced into HEK293T cells seeded in a 24-well plate coated with poly L-lysine, thereby obtaining transformed cells. These cells were irradiated with near-infrared light in the absence of a Tet-based compound, and a relative expression level of Ub-ELuc was investigated. After the plasmid transfection, luciferase assay was performed in the same manner as in "Functional screening of PA-Tet-OFF candidate constructs" described above, except that the medium was replaced with a 25 μM BV-containing medium 6 hours after the transfection, the cells were irradiated with near-infrared light (750 nm, 4.0 mW/cm$^2$) for 42 hours by being exposed to light for 30 seconds every 180 seconds, and a 750 nm LED (SMBB750D-1100, manufactured by Ushio Inc.) was used as a light source. All experiments were performed in 3 independent trials (3 batches) to obtain consistent results.

TABLE 7

| Construct ID | Element #1 N-terminus | Element #1 Linker | Element #1 C-terminus | Element #2 N-terminus | Element #2 Linker | Element #2 C-terminus | An initial construct screening result Dark | An initial construct screening result Light | An initial construct screening result Light/Dark | Three independent data sets to confirm reproducibility: Average of the Light/Dark ratio | Three independent data sets to confirm reproducibility: S.D. of the Light/Dark ratio |
|---|---|---|---|---|---|---|---|---|---|---|---|
| Negative control | I194T | SPKKK-HMEF | None | p65AD | HMEF | None | 1.0 | 0.9 | 1.0 | 1.2 | 0.2 |
| QT1 | I194T | SPKKK-HMEF | RpBph P1 | Q-PAS1 | TSTR | p55AD | 52.8 | 58.8 | 1.1 | 0.9 | 0.2 |
| QT2 | I194T | SPKKK-HMEF | RpBph P1 | Q-PAS1 | TSTR HMEF | p65AD-2xNLS | 22.6 | 33.4 | 1.6 | 1.5 | 0.3 |
| QT3 | I194T | SPKKK-HMEF | RpBph P1 | p65AD | | Q-PAS1 | 0.7 | 1.7 | 2.4 | 2.7 | 0.9 |
| QT4 | I194T | SPKKK-HMEF | RpBph P1 | 2xNLS-p65AD | HMEF | Q-PAS1 | 0.8 | 16.4 | 19.9 | 18.4 | 2.0 |
| QT5 | RpBph P1 | TSTR | I194T | Q-PAS1 | TSTR | p65AD | 287.7 | 478.7 | 1.9 | 1.4 | 0.5 |
| QT6 | RpBph P1 | TSTR | I194T | Q-PAS1 | TSTR | p65AD-2xNLS | 73.4 | 145.1 | 2.1 | 2.3 | 0.6 |
| QT7 | RpBph P1 | TSTR | I194T | p65AD | HMEF | Q-PAS1 | 1.0 | 9.6 | 9.9 | 10.2 | 0.3 |
| QT8 | RpBph P1 | TSTR | I194T | 2xNLS-p65AD | HMEF | Q-PAS1 | 6.4 | 106.3 | 16.7 | 20.2 | 4.7 |
| QT9 | I194T | SPKKK-HMEF | RpBph P1 | RpBph P1 | TSTR | p65AD | 2017.1 | 3297.3 | 1.8 | 1.8 | 0.1 |
| QT10 | I194T | SPKKK-HMEF | RpBph P1 | RpBph P1 | TSTR | p65AD-2xNLS | 638.9 | 905.1 | 1.6 | 1.6 | 0.1 |
| QT11 | I194T | SPKKK-HMEF | RpBph P1 | p65AD | HMEF | RpBph P1 | 1297.1 | 2819.0 | 2.2 | 2.4 | 0.3 |
| QT12 | I194T | SPKKK-HMEF | RpBph P1 | 2xNLS-p65AD | HMEF | RpBph P1 | 2625.3 | 5480.7 | 2.1 | 2.2 | 0.1 |
| QT13 | RpBph P1 | TSTR | I194T | RpBph P1 | TSTR | p65AD | 235.9 | 422.5 | 1.8 | 1.9 | 0.3 |
| QT14 | RpBph P1 | TSTR | I194T | RpBph P1 | TSTR | p65AD-2xNLS | 533.4 | 1143.9 | 2.2 | 1.6 | 0.6 |
| QT15 | RpBph P1 | TSTR | I194T | p65AD | HMEF | RpBph P1 | 137.8 | 209.9 | 1.6 | 1.5 | 0.2 |
| QT16 | RpBph P1 | TSTR | I194T | 2xNLS-p65AD | HMEF | RpBph P1 | 1449.2 | 1377.9 | 1.0 | 0.8 | 0.1 |
| No transfection | — | — | — | — | — | — | 0.6 | 0.8 | 1.3 | 1.6 | 0.8 |

The results are shown in Table 7. In Table 7, "I194T" in the column of "Element #1" represents TetR (I194T, 1-206). Furthermore, "Dark", "Light", and "Light/Dark" in the column of "An initial construct screening result" and "Average of the Light/Dark ratio", "Light/Dark", and "S.D. of the Light/Dark ratio" in the column of "Three independent data sets to confirm reproducibility" have the same definitions as those in Table 1 or the like. As shown in Table 7, the constructs with ID QT4, QT7, and QT8 had a Light/Dark ratio of 10 or higher and brought about PA-Tet-controlled expression efficiency markedly higher than PA-Tet-controlled expression efficiency in other candidate constructs. As a result, it was revealed that the combination of the fusion protein in which BphP1 is linked to the N-terminal side or C-terminal side of TetR and the fusion protein in which Q-PAS1 is linked to the C-terminal side of p65AD brings about excellent PA-Tet-controlled expression efficiency, and that the PA-Tet-controlled expression efficiency is further improved particularly in a case where 2 nuclear localization signals are linked in tandem to the N-terminal side of p65AD.

The same constructs were created by changing the transactivation domain of p65 to the transactivation domain of VP16 or VP64 widely used in the Tet system, and the Light/Dark ratio was investigated. As a result, all of these constructs brought about PA-Tet-controlled expression efficiency lower than the PA-Tet-controlled expression efficiency of the construct using p65. It was revealed that in the PA-Tet system, the combination of TetR or rTetR and the transactivation domain of p65 brings about the highest PA-Tet-controlled expression efficiency.

For the constructs with ID QT4 (Element #1: SEQ ID NO: 26, Element #2: SEQ ID NO: 27), QT7 (Element #1: SEQ ID NO: 28, Element #2: SEQ ID NO: 29), and QT8 (Element #1: SEQ ID NO: 28, Element #2: SEQ ID NO: 27), the PA-Tet-controlled expression efficiency was investigated by replacing the medium with a 25 μM BV-containing medium or a BV-free medium 6 hours after transfection. The results are shown in Table 8. In the table, "HEK293T(−)BV" represents the result obtained from the cells for which the medium was replaced with the BV-free medium, and "HEK293T(+)BV" represents the result obtained from the cells for which the medium was replaced with the B V-containing medium. It was revealed that the PA-Tet-controlled expression efficiency is improved in the cells that are cultured in the BV-containing medium and transfected with exogenous BV.

Next, for QT4, QT7 and QT8 constructs, the relationship between Dox concentration and gene expression induction was investigated. Specifically, the relationship was investigated in the same manner as in "Functional screening of PA-Tet-OFF candidate constructs" described above, except that HEK293T cells were seeded in a 24-well plate at $6\times10^4$ cells/well, the medium was replaced with a medium containing 25 μM BV and having Dox concentration described in Table 9 6 hours after transfection, the cells were irradiated with near-infrared light (750 nm, 4.0 mW/cm$^2$) for 42 hours by being exposed to light for 30 seconds every 180 seconds, and a 750 nm LED (SMBB750D-1100, manufactured by Ushio Inc.) was used as a light source. All experiments were performed in 3 independent trials (3 batches) to obtain consistent results.

TABLE 9

| Construct ID | Dox (ng/mL) | An initial construct screening result: Dark | Light | Light/Dark |
|---|---|---|---|---|
| QT4 | 0.000 | 0.8 | 17.7 | 23.8 |
| | 0.025 | 0.8 | 20.6 | 24.9 |
| | 0.050 | 0.7 | 10.7 | 16.0 |
| | 0.100 | 0.5 | 10.1 | 18.6 |
| | 0.200 | 0.3 | 2.9 | 10.3 |
| | 0.500 | 0.2 | 0.9 | 4.6 |
| | 1.000 | 0.2 | 0.2 | 1.2 |
| Negative control | 0.000 | 1.0 | 1.2 | 1.2 |
| QT7 | 0.0 | 2.8 | 53.7 | 20.2 |
| | 1.0 | 2.9 | 29.9 | 10.5 |
| | 2.0 | 2.7 | 34.7 | 13.1 |
| | 3.0 | 1.9 | 25.0 | 13.6 |
| | 4.0 | 1.3 | 17.6 | 13.9 |
| | 5.0 | 1.6 | 16.4 | 10.9 |
| | 10.0 | 0.3 | 3.7 | 11.2 |
| Negative control | 0.0 | 1.0 | 2.3 | 2.4 |
| QT8 | 0.0 | 13.2 | 152.0 | 11.6 |
| | 1.0 | 14.5 | 143.1 | 10.1 |
| | 2.0 | 17.1 | 112.2 | 6.8 |
| | 3.0 | 16.0 | 108.7 | 6.9 |
| | 4.0 | 15.1 | 86.8 | 6.0 |
| | 5.0 | 15.2 | 63.9 | 4.4 |
| | 10.0 | 3.1 | 7.2 | 2.4 |
| Negative control | 0.0 | 1.0 | 0.7 | 0.7 |

The results are shown in Table 9. In all three constructs, the Light/Dark ratio decreased in a Dox concentration-dependent manner even after the near-infrared light irradiation. From these results, it was revealed that these three constructs are useful as a PA-Tet-OFF system in which gene expression is induced by near-infrared light irradiation in the absence of Dox.

TABLE 8

| Construct ID | An initial construct screening result: HEK293T(−)BV Dark | Light | Light/Dark | HEK293T(+)BV Dark | Light | Light/Dark | Three independent data sets to confirm reproducibility: HEK293T(−)BV Average of the Light/Dark ratio | S.D. of the Light/Dark ratio | HEK293T(+)BV Average of the Light/Dark ratio | S.D. of the Light/Dark ratio |
|---|---|---|---|---|---|---|---|---|---|---|
| Negative control | 1.0 | 1.4 | 1.5 | 1.0 | 0.7 | 0.7 | 1.2 | 0.3 | 1.2 | 0.4 |
| QT4 | 5.6 | 33.8 | 6.0 | 1.3 | 36.6 | 28.7 | 4.9 | 0.9 | 28.1 | 5.9 |
| QT7 | 9.3 | 30.6 | 3.3 | 2.2 | 29.8 | 13.9 | 2.8 | 0.5 | 17.7 | 4.5 |
| QT8 | 71.9 | 196.4 | 2.8 | 14.4 | 162.0 | 11.2 | 2.0 | 0.6 | 13.2 | 2.5 |

What is claimed is:

1. A photoactivatable tetracycline gene expression control system, comprising:

a target gene expression cassette including a tetracycline response element having a TetO sequence, a promoter which is positioned downstream of the tetracycline response element and controlled by the tetracycline response element, and a target gene which is positioned downstream of the promoter and of which expression is controlled by the promoter;

a first fusion protein expression cassette including a gene which encodes a first fusion protein containing a Tet repressor protein or a reverse Tet repressor protein and a first protein; and a second fusion protein expression cassette including a gene which encodes a second fusion protein containing a transactivation domain of a transactivation element p65 and a second protein, wherein the first protein and the second protein bind to each other and form a heterodimer only in a state of being irradiated with light at a specific wavelength, and wherein the first protein is CIB1 or a variant thereof and the second protein is Cry2 or a variant thereof, or wherein the first protein is Cry2 or a variant thereof and the second protein is CIB1 or a variant thereof, and wherein the Tet repressor protein or the reverse Tet repressor protein has a threonine residue as an amino acid residue corresponding to the 194th isoleucine of a wild-type Tet repressor protein of *Escherichia coli.*

2. The photoactivatable tetracycline gene expression control system according to claim 1, wherein in the first fusion protein, the Tet repressor protein or the reverse Tet repressor protein is linked to the first protein through a peptide linker consisting of an amino acid sequence represented by SPKKK.

3. The photoactivatable tetracycline gene expression control system according to claim 1, wherein the first protein is CIB1 or a variant thereof, and the second protein is Cry2 or a variant thereof.

4. The photoactivatable tetracycline gene expression control system according to claim 3, wherein Cry2 or a variant thereof contained in the second fusion protein is a C-terminal deletion variant having an N-terminal photolyase homology region or a variant obtained by substituting an amino acid residue in the C-terminal deletion variant with phenylalanine, and the amino acid residue corresponds to the 348th leucine of wild-type Cry2 of *Arabidopsis thaliana.*

5. The photoactivatable tetracycline gene expression control system according to claim 1, wherein in the first fusion protein, CIB1 or a variant thereof is linked to a C-terminal side of the Tet repressor protein or the reverse Tet repressor protein.

6. The photoactivatable tetracycline gene expression control system according to claim 1, wherein the CIB1 or a variant thereof contained in the first fusion protein is a C-terminal deletion variant of CIB1 that consists of a partial protein corresponding to a region consisting of the 1st to 170th amino acids of wild-type CIB1 of *Arabidopsis thaliana* or a variant that is obtained by deleting a nuclear localization signal from the C-terminal deletion variant of CIB1.

7. The photoactivatable tetracycline gene expression control system according to claim 6, wherein CIB1 or a variant thereof contained in the first fusion protein is a variant obtained by deleting a nuclear localization signal from a C-terminal deletion variant of CIB1 consisting of a partial protein corresponding to a region consisting of the 1st to 170th amino acids of wild-type CIB1 of *Arabidopsis thaliana*, and the second fusion protein contains a nuclear localization signal on the N-terminal or the C-terminal.

8. The photoactivatable tetracycline gene expression control system according to claim 1, further comprising, in addition to the target gene expression cassette:

an expression cassette for a protein in which the first fusion protein and the second fusion protein are linked to each other through a T2A self-cleaving peptide; or an expression cassette for bicistronically expressing the first fusion protein and the second fusion protein.

9. The photoactivatable tetracycline gene expression control system according to claim 1, wherein the target gene is a gene that encodes a protein modified with ubiquitin.

10. A method for controlling target gene expression, comprising:

controlling expression of the target gene in a cell comprising the photoactivatable tetracycline gene expression control system according to claim 1 by adjusting conditions so that the cell is irradiated or not irradiated with blue light or near-infrared light and treated or not treated with a tetracycline-based compound.

11. A kit for a photoactivatable tetracycline gene expression control system, comprising:

a target gene expression vector including a tetracycline response element having a TetO sequence, a promoter which is positioned downstream of the tetracycline response element and controlled by the tetracycline response element, and a multicloning site which is positioned downstream of the promoter and into which a target gene will be inserted, and an expression vector including an expression cassette for a protein in which the first fusion protein and the second fusion protein are linked to each other through a T2A self-cleaving peptide, or an expression cassette for bicistronically expressing the first fusion protein and the second fusion protein, wherein the first fusion protein in which a Tet repressor protein or a reverse Tet repressor protein is linked to CIB1 or a variant thereof, and wherein the second fusion protein in which a transactivation domain of a transactivation element p65 is linked to Cry2 or a variant thereof, and wherein the Tet repressor protein or the reverse Tet repressor protein has a threonine residue as an amino acid residue corresponding to the 194th isoleucine of a wild-type Tet repressor protein of *Escherichia coli.*

12. A kit for a photoactivatable tetracycline gene expression control system, comprising:

a target gene expression vector including a tetracycline response element having a TetO sequence, a promoter which is positioned downstream of the tetracycline response element and controlled by the tetracycline response element, and a multicloning site which is positioned downstream of the promoter and into which a target gene will be inserted;

a first expression vector including a first fusion protein expression cassette containing a gene that encodes a first fusion protein in which a Tet repressor protein or a reverse Tet repressor protein is linked to CIB1 or a variant thereof, and a second expression vector including a second fusion protein expression cassette containing a gene that encodes a second fusion protein in which a transactivation domain of a transactivation element p65 is linked to Cry2 or a variant thereof, wherein the Tet repressor protein or the reverse Tet repressor protein has a threonine residue as an amino acid residue corresponding to the 194th isoleucine of a wild-type Tet repressor protein of *Escherichia coli.*

* * * * *

SEQUENCE LISTING

<160> NUMBER OF SEQ ID NOS: 29

<210> SEQ ID NO 1
<211> LENGTH: 206
<212> TYPE: PRT
<213> ORGANISM: Artificial Sequence
<220> FEATURE:
<223> OTHER INFORMATION: TetR

<400> SEQUENCE: 1

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly
        195                 200                 205
```

<210> SEQ ID NO 2
<211> LENGTH: 267
<212> TYPE: PRT
<213> ORGANISM: Artificial Sequence
<220> FEATURE:
<223> OTHER INFORMATION: p65AD

<400> SEQUENCE: 2

```
Glu Phe Gln Tyr Leu Pro Asp Thr Asp Asp Arg His Arg Ile Glu Glu
1               5                   10                  15

Lys Arg Lys Arg Thr Tyr Glu Thr Phe Lys Ser Ile Met Lys Lys Ser
            20                  25                  30

Pro Phe Ser Gly Pro Thr Asp Pro Arg Pro Pro Pro Arg Arg Ile Ala
        35                  40                  45

Val Pro Ser Arg Ser Ser Ala Ser Val Pro Lys Pro Ala Pro Gln Pro
    50                  55                  60

Tyr Pro Phe Thr Ser Ser Leu Ser Thr Ile Asn Tyr Asp Glu Phe Pro
65                  70                  75                  80

Thr Met Val Phe Pro Ser Gly Gln Ile Ser Gln Ala Ser Ala Leu Ala
                85                  90                  95
```

```
Pro Ala Pro Pro Gln Val Leu Pro Gln Ala Pro Ala Pro Ala Pro Ala
            100                 105                 110

Pro Ala Met Val Ser Ala Leu Ala Gln Ala Pro Ala Pro Val Pro Val
        115                 120                 125

Leu Ala Pro Gly Pro Pro Gln Ala Val Ala Pro Pro Ala Pro Lys Pro
    130                 135                 140

Thr Gln Ala Gly Glu Gly Thr Leu Ser Glu Ala Leu Leu Gln Leu Gln
145                 150                 155                 160

Phe Asp Asp Glu Asp Leu Gly Ala Leu Leu Gly Asn Ser Thr Asp Pro
                165                 170                 175

Ala Val Phe Thr Asp Leu Ala Ser Val Asp Asn Ser Glu Phe Gln Gln
            180                 185                 190

Leu Leu Asn Gln Gly Ile Pro Val Ala Pro His Thr Thr Glu Pro Met
        195                 200                 205

Leu Met Glu Tyr Pro Glu Ala Ile Thr Arg Leu Val Thr Gly Ala Gln
    210                 215                 220

Arg Pro Pro Asp Pro Ala Pro Ala Pro Leu Gly Ala Pro Gly Leu Pro
225                 230                 235                 240

Asn Gly Leu Leu Ser Gly Asp Glu Asp Phe Ser Ser Ile Ala Asp Met
                245                 250                 255

Asp Phe Ser Ala Leu Leu Ser Gln Ile Ser Ser
            260                 265


<210> SEQ ID NO 3
<211> LENGTH: 612
<212> TYPE: PRT
<213> ORGANISM: Artificial Sequence
<220> FEATURE:
<223> OTHER INFORMATION: Cry2

<400> SEQUENCE: 3

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190
```

-continued

```
Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Pro Asp Glu Ile Val Ala Asp Ser Phe Glu Ala Leu Gly Ala
            500                 505                 510

Asn Thr Ile Lys Glu Pro Gly Leu Cys Pro Ser Val Ser Ser Asn Asp
        515                 520                 525

Gln Gln Val Pro Ser Ala Val Arg Tyr Asn Gly Ser Lys Arg Val Lys
    530                 535                 540

Pro Glu Glu Glu Glu Glu Arg Asp Met Lys Lys Ser Arg Gly Phe Asp
545                 550                 555                 560

Glu Arg Glu Leu Phe Ser Thr Ala Glu Ser Ser Ser Ser Ser Ser Val
                565                 570                 575

Phe Phe Val Ser Gln Ser Cys Ser Leu Ala Ser Glu Gly Lys Asn Leu
            580                 585                 590

Glu Gly Ile Gln Asp Ser Ser Asp Gln Ile Thr Thr Ser Leu Gly Lys
        595                 600                 605

Asn Gly Cys Lys
```

610

<210> SEQ ID NO 4
<211> LENGTH: 335
<212> TYPE: PRT
<213> ORGANISM: Artificial Sequence
<220> FEATURE:
<223> OTHER INFORMATION: CIB1

<400> SEQUENCE: 4

```
Met Asn Gly Ala Ile Gly Gly Asp Leu Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Ala Ala Lys Phe
                85                  90                  95

Asp Thr Glu Thr Lys Asp Cys Asn Glu Ala Ala Lys Lys Met Thr Met
            100                 105                 110

Asn Arg Asp Asp Leu Val Glu Glu Gly Glu Glu Glu Lys Ser Lys Ile
        115                 120                 125

Thr Glu Gln Asn Asn Gly Ser Thr Lys Ser Ile Lys Lys Met Lys His
    130                 135                 140

Lys Ala Lys Lys Glu Glu Asn Asn Phe Ser Asn Asp Ser Ser Lys Val
145                 150                 155                 160

Thr Lys Glu Leu Glu Lys Thr Asp Tyr Ile His Val Arg Ala Arg Arg
                165                 170                 175

Gly Gln Ala Thr Asp Ser His Ser Ile Ala Glu Arg Val Arg Arg Glu
            180                 185                 190

Lys Ile Ser Glu Arg Met Lys Phe Leu Gln Asp Leu Val Pro Gly Cys
        195                 200                 205

Asp Lys Ile Thr Gly Lys Ala Gly Met Leu Asp Glu Ile Ile Asn Tyr
    210                 215                 220

Val Gln Ser Leu Gln Arg Gln Ile Glu Phe Leu Ser Met Lys Leu Ala
225                 230                 235                 240

Ile Val Asn Pro Arg Pro Asp Phe Asp Met Asp Asp Ile Phe Ala Lys
                245                 250                 255

Glu Val Ala Ser Thr Pro Met Thr Val Val Pro Ser Pro Glu Met Val
            260                 265                 270

Leu Ser Gly Tyr Ser His Glu Met Val His Ser Gly Tyr Ser Ser Glu
        275                 280                 285

Met Val Asn Ser Gly Tyr Leu His Val Asn Pro Met Gln Gln Val Asn
    290                 295                 300

Thr Ser Ser Asp Pro Leu Ser Cys Phe Asn Asn Gly Glu Ala Pro Ser
305                 310                 315                 320

Met Trp Asp Ser His Val Gln Asn Leu Tyr Gly Asn Leu Gly Val
                325                 330                 335
```

<210> SEQ ID NO 5
<211> LENGTH: 384
<212> TYPE: PRT

```
<213> ORGANISM: Artificial Sequence
<220> FEATURE:
<223> OTHER INFORMATION: Element #1 of T86 costruct

<400> SEQUENCE: 5

Met Ala Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Thr Cys Gly Leu Glu Lys Gln Leu Lys Cys Glu Ser Gly Ser Pro
        195                 200                 205

Lys Lys Lys His Met Glu Phe Asn Gly Ala Ile Gly Gly Asp Leu Leu
    210                 215                 220

Leu Asn Phe Pro Asp Met Ser Val Leu Glu Arg Gln Arg Ala His Leu
225                 230                 235                 240

Lys Tyr Leu Asn Pro Thr Phe Asp Ser Pro Leu Ala Gly Phe Phe Ala
                245                 250                 255

Asp Ser Ser Met Ile Thr Gly Gly Glu Met Asp Ser Tyr Leu Ser Thr
            260                 265                 270

Ala Gly Leu Asn Leu Pro Met Met Tyr Gly Glu Thr Thr Val Glu Gly
        275                 280                 285

Asp Ser Arg Leu Ser Ile Ser Pro Glu Thr Thr Leu Gly Thr Gly Asn
    290                 295                 300

Phe Lys Ala Ala Lys Phe Asp Thr Glu Thr Lys Asp Cys Asn Glu Ala
305                 310                 315                 320

Ala Lys Lys Met Thr Met Asn Arg Asp Asp Leu Val Glu Glu Gly Glu
                325                 330                 335

Glu Glu Lys Ser Lys Ile Thr Glu Gln Asn Asn Gly Ser Thr Lys Ser
            340                 345                 350

Ile Lys Lys Met Lys His Lys Ala Lys Lys Glu Glu Asn Asn Phe Ser
        355                 360                 365

Asn Asp Ser Ser Lys Val Thr Lys Glu Leu Glu Lys Thr Asp Tyr Ile
    370                 375                 380
```

<210> SEQ ID NO 6
<211> LENGTH: 784
<212> TYPE: PRT
<213> ORGANISM: Artificial Sequence
<220> FEATURE:
<223> OTHER INFORMATION: Element #2 of T86 costruct

<400> SEQUENCE: 6

```
Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Phe Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
```

```
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Thr Ser Thr Arg Glu Phe Gln Tyr Leu Pro Asp Thr Asp Asp Arg His
            500                 505                 510

Arg Ile Glu Glu Lys Arg Lys Arg Thr Tyr Glu Thr Phe Lys Ser Ile
        515                 520                 525

Met Lys Lys Ser Pro Phe Ser Gly Pro Thr Asp Pro Arg Pro Pro Pro
    530                 535                 540

Arg Arg Ile Ala Val Pro Ser Arg Ser Ser Ala Ser Val Pro Lys Pro
545                 550                 555                 560

Ala Pro Gln Pro Tyr Pro Phe Thr Ser Ser Leu Ser Thr Ile Asn Tyr
                565                 570                 575

Asp Glu Phe Pro Thr Met Val Phe Pro Ser Gly Gln Ile Ser Gln Ala
            580                 585                 590

Ser Ala Leu Ala Pro Ala Pro Pro Gln Val Leu Pro Gln Ala Pro Ala
        595                 600                 605

Pro Ala Pro Ala Pro Ala Met Val Ser Ala Leu Ala Gln Ala Pro Ala
    610                 615                 620

Pro Val Pro Val Leu Ala Pro Gly Pro Pro Gln Ala Val Ala Pro Pro
625                 630                 635                 640

Ala Pro Lys Pro Thr Gln Ala Gly Glu Gly Thr Leu Ser Glu Ala Leu
                645                 650                 655

Leu Gln Leu Gln Phe Asp Asp Glu Asp Leu Gly Ala Leu Leu Gly Asn
            660                 665                 670

Ser Thr Asp Pro Ala Val Phe Thr Asp Leu Ala Ser Val Asp Asn Ser
        675                 680                 685

Glu Phe Gln Gln Leu Leu Asn Gln Gly Ile Pro Val Ala Pro His Thr
    690                 695                 700

Thr Glu Pro Met Leu Met Glu Tyr Pro Glu Ala Ile Thr Arg Leu Val
705                 710                 715                 720

Thr Gly Ala Gln Arg Pro Pro Asp Pro Ala Pro Ala Pro Leu Gly Ala
                725                 730                 735

Pro Gly Leu Pro Asn Gly Leu Leu Ser Gly Asp Glu Asp Phe Ser Ser
            740                 745                 750

Ile Ala Asp Met Asp Phe Ser Ala Leu Leu Ser Gln Ile Ser Ser Pro
        755                 760                 765

Pro Lys Lys Lys Arg Lys Val Val Pro Pro Lys Lys Lys Arg Lys Val
    770                 775                 780
```

<210> SEQ ID NO 7

```
<211> LENGTH: 215
<212> TYPE: PRT
<213> ORGANISM: Artificial Sequence
<220> FEATURE:
<223> OTHER INFORMATION: Element #1 of Negative control costruct

<400> SEQUENCE: 7

Met Ala Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Thr Cys Gly Leu Glu Lys Gln Leu Lys Cys Glu Ser Gly Ser Pro
        195                 200                 205

Lys Lys Lys His Met Glu Phe
    210                 215


<210> SEQ ID NO 8
<211> LENGTH: 272
<212> TYPE: PRT
<213> ORGANISM: Artificial Sequence
<220> FEATURE:
<223> OTHER INFORMATION: Element #2 of Negative control costruct

<400> SEQUENCE: 8

Met Glu Phe Gln Tyr Leu Pro Asp Thr Asp Asp Arg His Arg Ile Glu
1               5                   10                  15

Glu Lys Arg Lys Arg Thr Tyr Glu Thr Phe Lys Ser Ile Met Lys Lys
            20                  25                  30

Ser Pro Phe Ser Gly Pro Thr Asp Pro Arg Pro Pro Pro Arg Arg Ile
        35                  40                  45

Ala Val Pro Ser Arg Ser Ser Ala Ser Val Pro Lys Pro Ala Pro Gln
    50                  55                  60

Pro Tyr Pro Phe Thr Ser Ser Leu Ser Thr Ile Asn Tyr Asp Glu Phe
65                  70                  75                  80

Pro Thr Met Val Phe Pro Ser Gly Gln Ile Ser Gln Ala Ser Ala Leu
                85                  90                  95

Ala Pro Ala Pro Pro Gln Val Leu Pro Gln Ala Pro Ala Pro Ala Pro
```

```
            100                 105                 110

Ala Pro Ala Met Val Ser Ala Leu Ala Gln Ala Pro Ala Pro Val Pro
        115                 120                 125

Val Leu Ala Pro Gly Pro Pro Gln Ala Val Ala Pro Pro Ala Pro Lys
    130                 135                 140

Pro Thr Gln Ala Gly Glu Gly Thr Leu Ser Glu Ala Leu Leu Gln Leu
145                 150                 155                 160

Gln Phe Asp Asp Glu Asp Leu Gly Ala Leu Leu Gly Asn Ser Thr Asp
                165                 170                 175

Pro Ala Val Phe Thr Asp Leu Ala Ser Val Asp Asn Ser Glu Phe Gln
            180                 185                 190

Gln Leu Leu Asn Gln Gly Ile Pro Val Ala Pro His Thr Thr Glu Pro
        195                 200                 205

Met Leu Met Glu Tyr Pro Glu Ala Ile Thr Arg Leu Val Thr Gly Ala
    210                 215                 220

Gln Arg Pro Pro Asp Pro Ala Pro Ala Pro Leu Gly Ala Pro Gly Leu
225                 230                 235                 240

Pro Asn Gly Leu Leu Ser Gly Asp Glu Asp Phe Ser Ser Ile Ala Asp
                245                 250                 255

Met Asp Phe Ser Ala Leu Leu Ser Gln Ile Ser Ser His Met Glu Phe
            260                 265                 270


<210> SEQ ID NO 9
<211> LENGTH: 1203
<212> TYPE: PRT
<213> ORGANISM: Artificial Sequence
<220> FEATURE:
<223> OTHER INFORMATION: TetR(I194T,1-206)-CIB1(-NLS)-T2A-Cry2
      PHR(L348F)-p65AD-NLS~2 fusion construct

<400> SEQUENCE: 9

Met Asp Tyr Lys Asp Asp Asp Asp Lys Ala Arg Leu Asp Lys Ser Lys
1               5                   10                  15

Val Ile Asn Ser Ala Leu Glu Leu Leu Asn Glu Val Gly Ile Glu Gly
            20                  25                  30

Leu Thr Thr Arg Lys Leu Ala Gln Lys Leu Gly Val Glu Gln Pro Thr
        35                  40                  45

Leu Tyr Trp His Val Lys Asn Lys Arg Ala Leu Leu Asp Ala Leu Ala
    50                  55                  60

Ile Glu Met Leu Asp Arg His His Thr His Phe Cys Pro Leu Glu Gly
65                  70                  75                  80

Glu Ser Trp Gln Asp Phe Leu Arg Asn Asn Ala Lys Ser Phe Arg Cys
                85                  90                  95

Ala Leu Leu Ser His Arg Asp Gly Ala Lys Val His Leu Gly Thr Arg
            100                 105                 110

Pro Thr Glu Lys Gln Tyr Glu Thr Leu Glu Asn Gln Leu Ala Phe Leu
        115                 120                 125

Cys Gln Gln Gly Phe Ser Leu Glu Asn Ala Leu Tyr Ala Leu Ser Ala
    130                 135                 140

Val Gly His Phe Thr Leu Gly Cys Val Leu Glu Asp Gln Glu His Gln
145                 150                 155                 160

Val Ala Lys Glu Glu Arg Glu Thr Pro Thr Thr Asp Ser Met Pro Pro
                165                 170                 175

Leu Leu Arg Gln Ala Ile Glu Leu Phe Asp His Gln Gly Ala Glu Pro
            180                 185                 190
```

```
Ala Phe Leu Phe Gly Leu Glu Leu Ile Thr Cys Gly Leu Glu Lys Gln
        195                 200                 205

Leu Lys Cys Glu Ser Gly Ser Pro Lys Lys Lys His Met Glu Phe Asn
    210                 215                 220

Gly Ala Ile Gly Gly Asp Leu Leu Leu Asn Phe Pro Asp Met Ser Val
225                 230                 235                 240

Leu Glu Arg Gln Arg Ala His Leu Lys Tyr Leu Asn Pro Thr Phe Asp
                245                 250                 255

Ser Pro Leu Ala Gly Phe Phe Ala Asp Ser Ser Met Ile Thr Gly Gly
            260                 265                 270

Glu Met Asp Ser Tyr Leu Ser Thr Ala Gly Leu Asn Leu Pro Met Met
        275                 280                 285

Tyr Gly Glu Thr Thr Val Glu Gly Asp Ser Arg Leu Ser Ile Ser Pro
    290                 295                 300

Glu Thr Thr Leu Gly Thr Gly Asn Phe Lys Ala Ala Lys Phe Asp Thr
305                 310                 315                 320

Glu Thr Lys Asp Cys Asn Glu Ala Ala Lys Lys Met Thr Met Asn Arg
                325                 330                 335

Asp Asp Leu Val Glu Glu Gly Glu Glu Glu Lys Ser Lys Ile Thr Glu
            340                 345                 350

Gln Asn Asn Gly Ser Thr Lys Ser Ile Lys Lys Met Lys His Lys Ala
        355                 360                 365

Lys Lys Glu Glu Asn Asn Phe Ser Asn Asp Ser Ser Lys Val Thr Lys
    370                 375                 380

Glu Leu Glu Lys Thr Asp Tyr Ile Thr Arg Glu Gly Arg Gly Ser Leu
385                 390                 395                 400

Leu Thr Cys Gly Asp Val Glu Glu Asn Pro Gly Pro Ala Thr Thr Thr
                405                 410                 415

Ser Ser Arg Met Lys Met Asp Lys Lys Thr Ile Val Trp Phe Arg Arg
            420                 425                 430

Asp Leu Arg Ile Glu Asp Asn Pro Ala Leu Ala Ala Ala Ala His Glu
        435                 440                 445

Gly Ser Val Phe Pro Val Phe Ile Trp Cys Pro Glu Glu Glu Gly Gln
    450                 455                 460

Phe Tyr Pro Gly Arg Ala Ser Arg Trp Trp Met Lys Gln Ser Leu Ala
465                 470                 475                 480

His Leu Ser Gln Ser Leu Lys Ala Leu Gly Ser Asp Leu Thr Leu Ile
                485                 490                 495

Lys Thr His Asn Thr Ile Ser Ala Ile Leu Asp Cys Ile Arg Val Thr
            500                 505                 510

Gly Ala Thr Lys Val Val Phe Asn His Leu Tyr Asp Pro Val Ser Leu
        515                 520                 525

Val Arg Asp His Thr Val Lys Glu Lys Leu Val Glu Arg Gly Ile Ser
    530                 535                 540

Val Gln Ser Tyr Asn Gly Asp Leu Leu Tyr Glu Pro Trp Glu Ile Tyr
545                 550                 555                 560

Cys Glu Lys Gly Lys Pro Phe Thr Ser Phe Asn Ser Tyr Trp Lys Lys
                565                 570                 575

Cys Leu Asp Met Ser Ile Glu Ser Val Met Leu Pro Pro Pro Trp Arg
            580                 585                 590

Leu Met Pro Ile Thr Ala Ala Ala Glu Ala Ile Trp Ala Cys Ser Ile
        595                 600                 605

Glu Glu Leu Gly Leu Glu Asn Glu Ala Glu Lys Pro Ser Asn Ala Leu
```

```
    610                 615                 620

Leu Thr Arg Ala Trp Ser Pro Gly Trp Ser Asn Ala Asp Lys Leu Leu
625                 630                 635                 640

Asn Glu Phe Ile Glu Lys Gln Leu Ile Asp Tyr Ala Lys Asn Ser Lys
                645                 650                 655

Lys Val Val Gly Asn Ser Thr Ser Leu Leu Ser Pro Tyr Leu His Phe
            660                 665                 670

Gly Glu Ile Ser Val Arg His Val Phe Gln Cys Ala Arg Met Lys Gln
        675                 680                 685

Ile Ile Trp Ala Arg Asp Lys Asn Ser Glu Gly Glu Glu Ser Ala Asp
    690                 695                 700

Leu Phe Leu Arg Gly Ile Gly Leu Arg Glu Tyr Ser Arg Tyr Ile Cys
705                 710                 715                 720

Phe Asn Phe Pro Phe Thr His Glu Gln Ser Leu Leu Ser His Leu Arg
                725                 730                 735

Phe Phe Pro Trp Asp Ala Asp Val Asp Lys Phe Lys Ala Trp Arg Gln
            740                 745                 750

Gly Arg Thr Gly Tyr Pro Leu Val Asp Ala Gly Met Arg Glu Phe Trp
        755                 760                 765

Ala Thr Gly Trp Met His Asn Arg Ile Arg Val Ile Val Ser Ser Phe
    770                 775                 780

Ala Val Lys Phe Leu Leu Leu Pro Trp Lys Trp Gly Met Lys Tyr Phe
785                 790                 795                 800

Trp Asp Thr Leu Leu Asp Ala Asp Leu Glu Cys Asp Ile Leu Gly Trp
                805                 810                 815

Gln Tyr Ile Ser Gly Ser Ile Pro Asp Gly His Glu Leu Asp Arg Leu
            820                 825                 830

Asp Asn Pro Ala Leu Gln Gly Ala Lys Tyr Asp Pro Glu Gly Glu Tyr
        835                 840                 845

Ile Arg Gln Trp Leu Pro Glu Leu Ala Arg Leu Pro Thr Glu Trp Ile
    850                 855                 860

His His Pro Trp Asp Ala Pro Leu Thr Val Leu Lys Ala Ser Gly Val
865                 870                 875                 880

Glu Leu Gly Thr Asn Tyr Ala Lys Pro Ile Val Asp Ile Asp Thr Ala
                885                 890                 895

Arg Glu Leu Leu Ala Lys Ala Ile Ser Arg Thr Arg Glu Ala Gln Ile
            900                 905                 910

Met Ile Gly Thr Ser Thr Arg Glu Phe Gln Tyr Leu Pro Asp Thr Asp
        915                 920                 925

Asp Arg His Arg Ile Glu Glu Lys Arg Lys Arg Thr Tyr Glu Thr Phe
    930                 935                 940

Lys Ser Ile Met Lys Lys Ser Pro Phe Ser Gly Pro Thr Asp Pro Arg
945                 950                 955                 960

Pro Pro Pro Arg Arg Ile Ala Val Pro Ser Arg Ser Ser Ala Ser Val
                965                 970                 975

Pro Lys Pro Ala Pro Gln Pro Tyr Pro Phe Thr Ser Ser Leu Ser Thr
            980                 985                 990

Ile Asn Tyr Asp Glu Phe Pro Thr Met Val Phe Pro Ser Gly Gln Ile
        995                 1000                1005

Ser Gln Ala Ser Ala Leu Ala Pro Ala Pro Pro Gln Val Leu Pro Gln
    1010                1015                1020

Ala Pro Ala Pro Ala Pro Ala Pro Ala Met Val Ser Ala Leu Ala Gln
1025                1030                1035                1040
```

```
Ala Pro Ala Pro Val Pro Val Leu Ala Pro Gly Pro Pro Gln Ala Val
                1045                1050                1055

Ala Pro Pro Ala Pro Lys Pro Thr Gln Ala Gly Glu Gly Thr Leu Ser
            1060                1065                1070

Glu Ala Leu Leu Gln Leu Gln Phe Asp Asp Glu Asp Leu Gly Ala Leu
        1075                1080                1085

Leu Gly Asn Ser Thr Asp Pro Ala Val Phe Thr Asp Leu Ala Ser Val
    1090                1095                1100

Asp Asn Ser Glu Phe Gln Gln Leu Leu Asn Gln Gly Ile Pro Val Ala
1105                1110                1115                1120

Pro His Thr Thr Glu Pro Met Leu Met Glu Tyr Pro Glu Ala Ile Thr
                1125                1130                1135

Arg Leu Val Thr Gly Ala Gln Arg Pro Pro Asp Pro Ala Pro Ala Pro
            1140                1145                1150

Leu Gly Ala Pro Gly Leu Pro Asn Gly Leu Leu Ser Gly Asp Glu Asp
        1155                1160                1165

Phe Ser Ser Ile Ala Asp Met Asp Phe Ser Ala Leu Leu Ser Gln Ile
    1170                1175                1180

Ser Ser Pro Pro Lys Lys Lys Arg Lys Val Val Pro Pro Lys Lys Lys
1185                1190                1195                1200

Arg Lys Val
```

<210> SEQ ID NO 10
<211> LENGTH: 2632
<212> TYPE: DNA
<213> ORGANISM: Artificial Sequence
<220> FEATURE:
<223> OTHER INFORMATION: TetR(I194T,1-206)-CIB1(-NLS) fusion construct
<220> FEATURE:
<221> NAME/KEY: promoter
<222> LOCATION: (1)..(1207)
<223> OTHER INFORMATION: hEF1a promoter
<220> FEATURE:
<221> NAME/KEY: mat_peptide
<222> LOCATION: (1236)..(1868)
<223> OTHER INFORMATION: TetR
<220> FEATURE:
<221> NAME/KEY: CDS
<222> LOCATION: (1881)..(2387)
<223> OTHER INFORMATION: Human optimized CIBN -ATG-stop NO NLS
<220> FEATURE:
<221> NAME/KEY: polyA_site
<222> LOCATION: (2408)..(2632)
<223> OTHER INFORMATION: pA

<400> SEQUENCE: 10

```
tctaggtctt gaaaggagtg ggaattggct ccggtgcccg tcagtgggca gagcgcacat     60

cgcccacagt ccccgagaag ttggggggag gggtcggcaa ttgaaccggt gcctagagaa    120

ggtggcgcgg ggtaaactgg gaaagtgatg tcgtgtactg gctccgcctt tttcccgagg    180

gtgggggaga accgtatata agtgcagtag tcgccgtgaa cgttcttttt cgcaacgggt    240

ttgccgccag aacacaggta agtgccgtgt gtggttcccg cgggcctggc ctctttacgg    300

gttatggccc ttgcgtgcct tgaattactt ccacctggct gcagtacgtg attcttgatc    360

ccgagcttcg ggttggaagt gggtgggaga gttcgaggcc ttgcgcttaa ggagcccctt    420

cgcctcgtgc ttgagttgag gcctggcctg ggcgctgggg ccgccgcgtg cgaatctggt    480

ggcaccttcg cgcctgtctc gctgctttcg ataagtctct agccatttaa aatttttgat    540

gacctgctgc gacgcttttt ttctggcaag atagtcttgt aaatgcgggc caagatctgc    600
```

acactggtat ttcggttttt ggggccgcgg gcggcgacgg ggcccgtgcg tcccagcgca 660
catgttcggc gaggcggggc ctgcgagcgc ggccaccgag aatcggacgg gggtagtctc 720
aagctggccg gcctgctctg gtgcctggcc tcgcgccgcc gtgtatcgcc ccgccctggg 780
cggcaaggct ggcccggtcg gcaccagttg cgtgagcgga aagatggccg cttcccggcc 840
ctgctgcagg gagctcaaaa tggaggacgc ggcgctcggg agagcgggcg ggtgagtcac 900
ccacacaaag gaaaagggcc tttccgtcct cagccgtcgc ttcatgtgac tccacggagt 960
accgggcgcc gtccaggcac ctcgattagt tctcgagctt ttggagtacg tcgtctttag 1020
gttgggggga ggggttttat gcgatggagt ttccccacac tgagtgggtg gagactgaag 1080
ttaggccagc ttggcacttg atgtaattct ccttggaatt tgcccttttt gagtttggat 1140
cttggttcat tctcaagcct cagacagtgg ttcaaagttt ttttcttcca tttcaggtgt 1200
cgtgagttaa ttaattatcg atacgtcgac ccaccatggc tagattagat aaaagtaaag 1260
tgattaacag cgcattagag ctgcttaatg aggtcggaat cgaaggttta acaacccgta 1320
aactcgccca gaagctaggt gtagagcagc ctacattgta ttggcatgta aaaaataagc 1380
gggctttgct cgacgcctta gccattgaga tgttagatag gcaccatact cacttttgcc 1440
ctttagaagg ggaaagctgg caagattttt tacgtaataa cgctaaaagt tttagatgtg 1500
ctttactaag tcatcgcgat ggagcaaaag tacatttagg tacacggcct acagaaaaac 1560
agtatgaaac tctcgaaaat caattagcct ttttatgcca acaaggtttt tcactagaga 1620
atgcattata tgcactcagc gctgtggggc attttacttt aggttgcgta ttggaagatc 1680
aagagcatca agtcgctaaa gaagaaaggg aaacacctac tactgatagt atgccgccat 1740
tattacgaca agctatcgaa ttatttgatc accaaggtgc agagccagcc ttcttattcg 1800
gccttgaatt gatcacatgc ggattagaaa aacaacttaa atgtgaaagt gggtcgccaa 1860
aaaagaagca tatggaattc aatggggcaa taggaggtga tctgttgctc aactttcccg 1920
acatgagcgt gctcgaaagg caacgcgcac atctgaagta cctgaatccc acctttgaca 1980
gtccattggc aggcttcttc gccgacagca gcatgatcac aggaggcgag atggacagtt 2040
atctgagcac tgctgggctc aacttgccca tgatgtacgg tgaaacaact gtcgagggtg 2100
attccaggct ttccatctca ccggaaacga cccttggaac tggcaatttt aaggctgcga 2160
agtttgacac cgagactaaa gattgcaacg aggcagccaa gaagatgacc atgaatcggg 2220
acgatctggt ggaagaaggg gaagaggaga aatccaagat taccgaacag aacaatggca 2280
gtaccaagtc aatcaagaag atgaagcaca aagccaagaa ggaagaaaac aacttcagca 2340
atgactctag caaagtgaca aaagagctgg agaaaacgga ctacatctaa ggatccatcg 2400
cggccgccca gacatgataa gatacattga tgagtttgga caaaccacaa ctagaatgca 2460
gtgaaaaaaa tgctttattt gtgaaatttg tgatgctatt gctttatttg taaccattat 2520
aagctgcaat aaacaagtta acaacaacaa ttgcattcat tttatgtttc aggttcaggg 2580
ggaggtgtgg gaggtttttt aaagcaagta aaacctctac aaatgtggta tg 2632

<210> SEQ ID NO 11
<211> LENGTH: 3829
<212> TYPE: DNA
<213> ORGANISM: Artificial Sequence
<220> FEATURE:
<223> OTHER INFORMATION: Cry2 PHR(L348F)-p65AD-NLS?~2 fusion construct
<220> FEATURE:
<221> NAME/KEY: promoter
<222> LOCATION: (1)..(1207)
<223> OTHER INFORMATION: hEF1a promoter
<220> FEATURE:
<221> NAME/KEY: CDS
<222> LOCATION: (1239)..(2723)
<223> OTHER INFORMATION: Human optimized Cry2 PHR L348F -ATG-stop
<220> FEATURE:
<221> NAME/KEY: mat_peptide
<222> LOCATION: (2736)..(3536)
<223> OTHER INFORMATION: Human p65 AD
<220> FEATURE:
<221> NAME/KEY: sig_peptide
<222> LOCATION: (3537)..(3560)
<223> OTHER INFORMATION: NLS
<220> FEATURE:
<221> NAME/KEY: sig_peptide
<222> LOCATION: (3564)..(3587)
<223> OTHER INFORMATION: NLS
<220> FEATURE:
<221> NAME/KEY: polyA_site
<222> LOCATION: (3605)..(3829)
<223> OTHER INFORMATION: pA

<400> SEQUENCE: 11

```
tctaggtctt gaaaggagtg ggaattggct ccggtgcccg tcagtgggca gagcgcacat     60

cgcccacagt ccccgagaag ttggggggag gggtcggcaa ttgaaccggt gcctagagaa    120

ggtggcgcgg ggtaaactgg gaaagtgatg tcgtgtactg gctccgcctt tttcccgagg    180

gtgggggaga accgtatata agtgcagtag tcgccgtgaa cgttcttttt cgcaacgggt    240

ttgccgccag aacacaggta agtgccgtgt gtggttcccg cgggcctggc ctctttacgg    300

gttatggccc ttgcgtgcct tgaattactt ccacctggct gcagtacgtg attcttgatc    360

ccgagcttcg ggttggaagt gggtgggaga gttcgaggcc ttgcgcttaa ggagcccctt    420

cgcctcgtgc ttgagttgag gcctggcctg ggcgctgggg ccgccgcgtg cgaatctggt    480

ggcaccttcg cgcctgtctc gctgctttcg ataagtctct agccatttaa aatttttgat    540

gacctgctgc gacgcttttt ttctggcaag atagtcttgt aaatgcgggc caagatctgc    600

acactggtat ttcggttttt ggggccgcgg gcggcgacgg ggcccgtgcg tcccagcgca    660

catgttcggc gaggcggggc ctgcgagcgc ggccaccgag aatcggacgg gggtagtctc    720

aagctggccg gcctgctctg gtgcctggcc tcgcgccgcc gtgtatcgcc ccgccctggg    780

cggcaaggct ggcccggtcg gcaccagttg cgtgagcgga aagatggccg cttcccggcc    840

ctgctgcagg gagctcaaaa tggaggacgc ggcgctcggg agagcgggcg ggtgagtcac    900

ccacacaaag gaaaagggcc tttccgtcct cagccgtcgc ttcatgtgac tccacggagt    960

accgggcgcc gtccaggcac ctcgattagt tctcgagctt ttggagtacg tcgtctttag   1020

gttgggggga ggggttttat gcgatggagt ttccccacac tgagtgggtg gagactgaag   1080

ttaggccagc ttggcacttg atgtaattct ccttggaatt tgcccttttt gagtttggat   1140

cttggttcat tctcaagcct cagacagtgg ttcaaagttt ttttcttcca tttcaggtgt   1200

cgtgagttaa ttaattatcg atacgtcgac ccaccatgaa aatggacaag aaaaccatcg   1260

tgtggttcag gagggatctg agaatcgagg ataatcccgc cctcgccgca gctgctcacg   1320

aagggagtgt gtttccggtg ttcatttggt gtccagagga agaggggcag ttctaccctg   1380

gacgagcaag tcgctggtgg atgaaacagt ccctggccca tctgtctcag agcctcaagg   1440

cccttggctc tgatctcacc ctgatcaaga cgcataatac aatctccgca attctcgatt   1500

gcattcgcgt cacaggtgcg acgaaagtgg ttttcaacca cctgtatgat ccagtttcac   1560

tggtccgtga tcacaccgtg aaagagaaac tggtagagag aggcattagt gtgcagagct   1620

acaacgggga tctgctgtac gaaccctggg agatttactg cgaaaagggt aagccattta   1680
```

```
ctagcttcaa ttcctattgg aagaaatgtc tggacatgtc aatcgagagc gtgatgctgc   1740

ctccaccatg gcgactcatg cccataactg ctgctgctga agcgatttgg gcctgctcca   1800

ttgaggagtt gggccttgag aatgaggcgg agaagcccag taatgctctg ctgaccaggg   1860

catggagtcc aggatggtca aatgccgaca aactcctgaa tgagttcata gagaaacagc   1920

tgattgacta tgccaagaac tccaagaagg ttgtgggtaa ctcaacctct cttctcagcc   1980

cctatctgca ctttggggag ataagcgtcc ggcatgtgtt ccagtgtgcg cggatgaagc   2040

agatcatttg ggcgagggat aagaacagcg agggagagga atccgcagac ttgttcctgc   2100

ggggcatcgg gctccgcgaa tatagccggt atatctgctt taacttccct tttactcacg   2160

agcagagcct tctgagccat ctgcgcttct ttccttggga tgcagacgtg gacaaattta   2220

aggcttggcg tcaaggtagg accggctatc cactggtcga tgccggcatg agagaatttt   2280

gggccactgg gtggatgcac aaccggatta gggtgatcgt atcttccttt gccgtcaagt   2340

ttctgttgtt gccctggaaa tggggcatga agtacttttg ggataccctg ttggacgccg   2400

atctggaatg cgacatcctt ggttggcaat acataagtgg ctcaataccc gacggccatg   2460

agctggatag acttgacaat ccggctctgc aaggggctaa gtacgacccc gaaggagaat   2520

acatcagaca gtggctcccc gaattggcca gactccccac agagtggatt caccacccct   2580

gggacgcacc tctgacagtt ctcaaagcca gcggagtaga actgggcact aactacgcca   2640

agccgatagt ggacattgac acagctcggg aactgttggc caaagcaatc tctcgcacac   2700

gagaagccca gatcatgatc ggaactagta cgcgtgagtt ccagtacctg cccgacaccg   2760

acgaccggca ccggatcgag gaaaagcgga agcggaccta cgagacattc aagagcatta   2820

tgaagaagtc cccctcagc ggccccaccg accccagacc cccacctaga agaatcgccg   2880

tgcccagcag atccagcgcc agcgtgccaa agcctgcccc ccagccctac cccttcacca   2940

gcagcctgag caccatcaac tacgatgagt tccccacaat ggtgttcccc agcggccaga   3000

tttctcaggc ctctgctctg gccccagccc ctccacaggt gctgccacag gcccctgctc   3060

cagctcctgc ccctgctatg gtgtctgccc tggcccaggc tccagctcct gtgcctgtgc   3120

tggctcctgg acctccacag gccgtggccc ctccagcccc aaaacctaca caggccggcg   3180

agggcacact gagcgaagcc ctgctccagc tccagttcga cgacgaggat ctgggcgccc   3240

tgctgggcaa cagcaccgac cctgccgtgt tcaccgacct ggccagcgtg gacaacagcg   3300

agttccagca gctcctgaac cagggcatcc ccgtggctcc acacaccacc gagcccatgc   3360

tgatggaata ccccgaggcc atcacccggc tggtcacagg cgctcagagg cctcctgatc   3420

ctgccccagc tccactggga gcccctggcc tgcctaatgg cctgctgagc ggcgacgagg   3480

acttcagctc tatcgccgac atggacttct ccgccctgct gtcccagatc agcagccctc   3540

caaaaaagaa gagaaaggta gtacctccaa aaaagaagag aaaggtataa aagcttgcgg   3600

ccgcccagac atgataagat acattgatga gtttggacaa accacaacta gaatgcagtg   3660

aaaaaaatgc tttatttgtg aaatttgtga tgctattgct ttatttgtaa ccattataag   3720

ctgcaataaa caagttaaca acaacaattg cattcatttt atgtttcagg ttcaggggga   3780

ggtgtgggag gtttttaaa gcaagtaaaa cctctacaaa tgtggtatg             3829
```

<210> SEQ ID NO 12
<211> LENGTH: 5086
<212> TYPE: DNA
<213> ORGANISM: Artificial Sequence
<220> FEATURE:
<223> OTHER INFORMATION: TetR(I194T,1-206)-CIB1(-NLS)-T2A-Cry2

PHR(L348F)-p65AD-NLS?~2 fusion construct
<220> FEATURE:
<221> NAME/KEY: promoter
<222> LOCATION: (1)..(1207)
<223> OTHER INFORMATION: hEF1a promoter
<220> FEATURE:
<222> LOCATION: (1236)..(1238)
<223> OTHER INFORMATION: initiation codon
<220> FEATURE:
<221> NAME/KEY: mat_peptide
<222> LOCATION: (1239)..(1262)
<223> OTHER INFORMATION: FLAG tag
<220> FEATURE:
<221> NAME/KEY: mat_peptide
<222> LOCATION: (1263)..(1892)
<223> OTHER INFORMATION: TetR (no AD) + I194T + SPKKK
<220> FEATURE:
<221> NAME/KEY: CDS
<222> LOCATION: (1905)..(2411)
<223> OTHER INFORMATION: Human optimized CIBN -ATG-stop NO NLS
<220> FEATURE:
<221> NAME/KEY: sig_peptide
<222> LOCATION: (2418)..(2471)
<223> OTHER INFORMATION: T2A
<220> FEATURE:
<221> NAME/KEY: CDS
<222> LOCATION: (2493)..(3980)
<223> OTHER INFORMATION: Human optimized Cry2 PHR L348F -ATG-stop
<220> FEATURE:
<221> NAME/KEY: mat_peptide
<222> LOCATION: (3998)..(4793)
<223> OTHER INFORMATION: Human p65 AD
<220> FEATURE:
<221> NAME/KEY: sig_peptide
<222> LOCATION: (4794)..(4817)
<223> OTHER INFORMATION: NLS
<220> FEATURE:
<221> NAME/KEY: sig_peptide
<222> LOCATION: (4821)..(4844)
<223> OTHER INFORMATION: NLS
<220> FEATURE:
<222> LOCATION: (4845)..(4847)
<223> OTHER INFORMATION: STOP codon
<220> FEATURE:
<221> NAME/KEY: polyA_site
<222> LOCATION: (4862)..(5086)
<223> OTHER INFORMATION: pA

<400> SEQUENCE: 12
tctaggtctt gaaaggagtg ggaattggct ccggtgcccg tcagtgggca gagcgcacat 60
cgcccacagt ccccgagaag ttgggggag gggtcggcaa ttgaaccggt gcctagagaa 120
ggtggcgcgg ggtaaactgg gaaagtgatg tcgtgtactg gctccgcctt tttcccgagg 180
gtgggggaga accgtatata agtgcagtag tcgccgtgaa cgttcttttt cgcaacgggt 240
ttgccgccag aacacaggta agtgccgtgt gtggttcccg cgggcctggc ctctttacgg 300
gttatggccc ttgcgtgcct tgaattactt ccacctggct gcagtacgtg attcttgatc 360
ccgagcttcg ggttggaagt gggtgggaga gttcgaggcc ttgcgcttaa ggagcccctt 420
cgcctcgtgc ttgagttgag gcctggcctg ggcgctgggg ccgccgcgtg cgaatctggt 480
ggcaccttcg cgcctgtctc gctgctttcg ataagtctct agccatttaa aatttttgat 540
gacctgctgc gacgcttttt ttctggcaag atagtcttgt aaatgcgggc caagatctgc 600
acactggtat ttcggttttt ggggccgcgg gcggcgacgg ggcccgtgcg tcccagcgca 660
catgttcggc gaggcggggc ctgcgagcgc ggccaccgag aatcggacgg gggtagtctc 720
aagctggccg gcctgctctg gtgcctggcc tcgcgccgcc gtgtatcgcc ccgccctggg 780
cggcaaggct ggcccggtcg gcaccagttg cgtgagcgga aagatggccg cttcccggcc 840
ctgctgcagg gagctcaaaa tggaggacgc ggcgctcggg agagcgggcg ggtgagtcac 900

```
ccacacaaag gaaaagggcc tttccgtcct cagccgtcgc ttcatgtgac tccacggagt    960
accgggcgcc gtccaggcac ctcgattagt tctcgagctt ttggagtacg tcgtctttag   1020
gttgggggga ggggttttat gcgatggagt ttccccacac tgagtgggtg gagactgaag   1080
ttaggccagc ttggcacttg atgtaattct ccttggaatt tgcccttttt gagtttggat   1140
cttggttcat tctcaagcct cagacagtgg ttcaaagttt ttttcttcca tttcaggtgt   1200
cgtgagttaa ttaattatcg atacgtcgac ccaccatgga ctacaaggac gacgatgaca   1260
aggctagatt agataaaagt aaagtgatta acagcgcatt agagctgctt aatgaggtcg   1320
gaatcgaagg tttaacaacc cgtaaactcg cccagaagct aggtgtagag cagcctacat   1380
tgtattggca tgtaaaaaat aagcgggctt tgctcgacgc cttagccatt gagatgttag   1440
ataggcacca tactcacttt tgccctttag aaggggaaag ctggcaagat tttttacgta   1500
ataacgctaa aagttttaga tgtgctttac taagtcatcg cgatggagca aaagtacatt   1560
taggtacacg gcctacagaa aaacagtatg aaactctcga aaatcaatta gcctttttat   1620
gccaacaagg tttttcacta gagaatgcat tatatgcact cagcgctgtg gggcatttta   1680
ctttaggttg cgtattggaa gatcaagagc atcaagtcgc taaagaagaa agggaaacac   1740
ctactactga tagtatgccg ccattattac gacaagctat cgaattattt gatcaccaag   1800
gtgcagagcc agccttctta ttcggccttg aattgatcac atgcggatta gaaaaacaac   1860
ttaaatgtga aagtgggtcg ccaaaaaaga agcatatgga attcaatggg gcaataggag   1920
gtgatctgtt gctcaacttt cccgacatga gcgtgctcga aaggcaacgc gcacatctga   1980
agtacctgaa tcccaccttt gacagtccat tggcaggctt cttcgccgac agcagcatga   2040
tcacaggagg cgagatggac agttatctga gcactgctgg gctcaacttg cccatgatgt   2100
acggtgaaac aactgtcgag ggtgattcca ggctttccat ctcaccggaa acgacccttg   2160
gaactggcaa ttttaaggct gcgaagtttg acaccgagac taaagattgc aacgaggcag   2220
ccaagaagat gaccatgaat cgggacgatc tggtggaaga aggggaagag gagaaatcca   2280
agattaccga acagaacaat ggcagtacca agtcaatcaa gaagatgaag cacaaagcca   2340
agaaggaaga aaacaacttc agcaatgact ctagcaaagt gacaaaagag ctggagaaaa   2400
cggactacat cacgcgtgag ggcagaggaa gtctgctaac atgcggtgac gtcgaggaga   2460
atcctggccc agccacaacc actagttcta gaatgaaaat ggacaagaaa accatcgtgt   2520
ggttcaggag ggatctgaga atcgaggata atcccgccct cgccgcagct gctcacgaag   2580
ggagtgtgtt tccggtgttc atttggtgtc cagaggaaga ggggcagttc taccctggac   2640
gagcaagtcg ctggtggatg aaacagtccc tggcccatct gtctcagagc ctcaaggccc   2700
ttggctctga tctcaccctg atcaagacgc ataatacaat ctccgcaatt ctcgattgca   2760
ttcgcgtcac aggtgcgacg aaagtggttt tcaaccacct gtatgatcca gtttcactgg   2820
tccgtgatca caccgtgaaa gagaaactgg tagagagagg cattagtgtg cagagctaca   2880
acggggatct gctgtacgaa ccctgggaga tttactgcga aaagggtaag ccatttacta   2940
gcttcaattc ctattggaag aaatgtctgg acatgtcaat cgagagcgtg atgctgcctc   3000
caccatggcg actcatgccc ataactgctg ctgctgaagc gatttgggcc tgctccattg   3060
aggagttggg ccttgagaat gaggcggaga agcccagtaa tgctctgctg accagggcat   3120
ggagtccagg atggtcaaat gccgacaaac tcctgaatga gttcatagag aaacagctga   3180
ttgactatgc caagaactcc aagaaggttg tgggtaactc aacctctctt ctcagcccct   3240
```

```
atctgcactt tggggagata agcgtccggc atgtgttcca gtgtgcgcgg atgaagcaga   3300
tcatttgggc gagggataag aacagcgagg gagaggaatc cgcagacttg ttcctgcggg   3360
gcatcgggct ccgcgaatat agccggtata tctgctttaa cttccctttt actcacgagc   3420
agagccttct gagccatctg cgcttctttc cttgggatgc agacgtggac aaatttaagg   3480
cttggcgtca aggtaggacc ggctatccac tggtcgatgc cggcatgaga gaattttggg   3540
ccactgggtg gatgcacaac cggattaggg tgatcgtatc ttcctttgcc gtcaagtttc   3600
tgttgttgcc ctggaaatgg ggcatgaagt acttttggga taccctgttg gacgccgatc   3660
tggaatgcga catccttggt tggcaataca taagtggctc aatacccgac ggccatgagc   3720
tggatagact tgacaatccg gctctgcaag ggcctaagta cgaccccgaa ggagaataca   3780
tcagacagtg gctccccgaa ttggccagac tccccacaga gtggattcac cacccttggg   3840
acgcacctct gacagttctc aaagccagcg gagtagaact gggcactaac tacgccaagc   3900
cgatagtgga cattgacaca gctcgggaac tgttggccaa agcaatctct cgcacacgag   3960
aagcccagat catgatcgga actagtacgc gtgagttcca gtacctgccc gacaccgacg   4020
accggcaccg gatcgaggaa aagcggaagc ggacctacga gacattcaag agcattatga   4080
agaagtcccc cttcagcggc cccaccgacc ccagaccccc acctagaaga atcgccgtgc   4140
ccagcagatc cagcgccagc gtgccaaagc ctgcccccca gccctacccc ttcaccagca   4200
gcctgagcac catcaactac gatgagttcc ccacaatggt gttccccagc ggccagattt   4260
ctcaggcctc tgctctggcc ccagcccctc cacaggtgct gccacaggcc cctgctccag   4320
ctcctgcccc tgctatggtg tctgccctgg cccaggctcc agctcctgtg cctgtgctgg   4380
ctcctggacc tccacaggcc gtggcccctc cagccccaaa acctacacag gccggcgagg   4440
gcacactgag cgaagccctg ctccagctcc agttcgacga cgaggatctg ggcgccctgc   4500
tgggcaacag caccgaccct gccgtgttca ccgacctggc cagcgtggac aacagcgagt   4560
tccagcagct cctgaaccag ggcatccccg tggctccaca caccaccgag cccatgctga   4620
tggaataccc cgaggccatc acccggctgg tcacaggcgc tcagaggcct cctgatcctg   4680
ccccagctcc actgggagcc cctggcctgc ctaatggcct gctgagcggc gacgaggact   4740
tcagctctat cgccgacatg gacttctccg ccctgctgtc ccagatcagc agccctccaa   4800
aaaagaagag aaaggtagta cctccaaaaa agaagagaaa ggtataaaag cttgcggccg   4860
cccagacatg ataagataca ttgatgagtt tggacaaacc acaactagaa tgcagtgaaa   4920
aaaatgcttt atttgtgaaa tttgtgatgc tattgcttta tttgtaacca ttataagctg   4980
caataaacaa gttaacaaca acaattgcat tcattttatg tttcaggttc agggggaggt   5040
gtgggaggtt ttttaaagca agtaaaacct ctacaaatgt ggtatg                  5086
```

<210> SEQ ID NO 13
<211> LENGTH: 5
<212> TYPE: PRT
<213> ORGANISM: Artificial Sequence
<220> FEATURE:
<223> OTHER INFORMATION: Linker

<400> SEQUENCE: 13

```
Ser Pro Lys Lys Lys
1               5
```

<210> SEQ ID NO 14
<211> LENGTH: 24
<212> TYPE: PRT

```
<213> ORGANISM: Artificial Sequence
<220> FEATURE:
<223> OTHER INFORMATION: Linker

<400> SEQUENCE: 14

Thr Gly Asn Ser Ala Asp Gly Gly Gly Gly Ser Gly Gly Ser Gly Gly
1               5                   10                  15

Ser Gly Gly Gly Ser Thr Gln Gly
            20


<210> SEQ ID NO 15
<211> LENGTH: 16
<212> TYPE: PRT
<213> ORGANISM: Artificial Sequence
<220> FEATURE:
<223> OTHER INFORMATION: Linker

<400> SEQUENCE: 15

Leu Glu Ala Ser Pro Ser Asn Pro Gly Ala Ser Asn Gly Ser Gly Thr
1               5                   10                  15


<210> SEQ ID NO 16
<211> LENGTH: 10
<212> TYPE: PRT
<213> ORGANISM: Artificial Sequence
<220> FEATURE:
<223> OTHER INFORMATION: Linker

<400> SEQUENCE: 16

Gly Tyr Pro Ser His Trp Arg Pro Leu Glu
1               5                   10


<210> SEQ ID NO 17
<211> LENGTH: 10
<212> TYPE: PRT
<213> ORGANISM: Artificial Sequence
<220> FEATURE:
<223> OTHER INFORMATION: Linker

<400> SEQUENCE: 17

Leu Glu Ala Ser Thr Gly Gly Ser Gly Thr
1               5                   10


<210> SEQ ID NO 18
<211> LENGTH: 4350
<212> TYPE: DNA
<213> ORGANISM: Artificial Sequence
<220> FEATURE:
<223> OTHER INFORMATION: CAG-FLAG-TetR-CIBN(-NLS)-T2A-mCherryNLS
      construct (Virus 1)
<220> FEATURE:
<222> LOCATION: (1)..(133)
<223> OTHER INFORMATION: ITR
<220> FEATURE:
<221> NAME/KEY: promoter
<222> LOCATION: (196)..(1132)
<223> OTHER INFORMATION: pCAG
<220> FEATURE:
<222> LOCATION: (1186)..(1188)
<223> OTHER INFORMATION: initiation codon
<220> FEATURE:
<221> NAME/KEY: mat_peptide
<222> LOCATION: (1189)..(1212)
<223> OTHER INFORMATION: FLAG tag
<220> FEATURE:
<221> NAME/KEY: mat_peptide
<222> LOCATION: (1213)..(1842)
<223> OTHER INFORMATION: TetR (no AD) + I194T + SPKKK
<220> FEATURE:
<221> NAME/KEY: CDS
```

<222> LOCATION: (1855)..(2361)
<223> OTHER INFORMATION: Human optimized CIBN -ATG-stop NO NLS
<220> FEATURE:
<221> NAME/KEY: sig_peptide
<222> LOCATION: (2368)..(2421)
<223> OTHER INFORMATION: T2A
<220> FEATURE:
<221> NAME/KEY: mat_peptide
<222> LOCATION: (2437)..(3141)
<223> OTHER INFORMATION: mCherry (no STOP)
<220> FEATURE:
<221> NAME/KEY: sig_peptide
<222> LOCATION: (3142)..(3165)
<223> OTHER INFORMATION: NLS
<220> FEATURE:
<221> NAME/KEY: sig_peptide
<222> LOCATION: (3169)..(3192)
<223> OTHER INFORMATION: NLS
<220> FEATURE:
<222> LOCATION: (3196)..(3198)
<223> OTHER INFORMATION: STOP codon
<220> FEATURE:
<222> LOCATION: (3293)..(3901)
<223> OTHER INFORMATION: WPRE
<220> FEATURE:
<221> NAME/KEY: polyA_site
<222> LOCATION: (3931)..(4050)
<223> OTHER INFORMATION: SV40 early pA
<220> FEATURE:
<222> LOCATION: (4217)..(4350)
<223> OTHER INFORMATION: ITR

<400> SEQUENCE: 18
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtagccatgc 180
tctaggaaga tcgtaccatt gacgtcaata atgacgtatg ttcccatagt aacgccaata 240
gggactttcc attgacgtca atgggtggag tatttacggt aaactgccca cttggcagta 300
catcaagtgt atcatatgcc aagtacgccc cctattgacg tcaatgacgg taaatggccc 360
gcctggcatt atgcccagta catgacctta tgggactttc ctacttggca gtacatctac 420
gtattagtca tcgctattac catggtcgag gtgagcccca cgttctgctt cactctcccc 480
atctcccccc cctccccacc cccaattttg tatttattta tttttttaatt attttgtgca 540 gcgatggggg cggggggggg ggggggggcgc gcgccaggcg gggcggggcg gggcgagggg 600
cggggcgggg cgaggcggag aggtgcggcg gcagccaatc agagcggcgc gctccgaaag 660
tttcctttta tggcgaggcg gcggcggcgg cggccctata aaaagcgaag cgcgcggcgg 720
gcgggagtcg ctgcgacgct gccttcgccc cgtgccccgc tccgccgccg cctcgcgccg 780
cccgccccgg ctctgactga ccgcgttact cccacaggtg agcgggcggg acggcccttc 840
tcctccgggc tgtaattagc gcttggttta atgacggctt gtttcttttc tgtggctgcg 900
tgaaagcctt gaggggctcc gggagggccc tttgtgcggg gggagcggct cggggctgtc 960
cgcgggggga cggctgcctt cgggggggac ggggcagggc ggggttcggc ttctggcgtg 1020
tgaccggcgg ctctagagcc tctgctaacc atgttcatgc cttcttcttt ttcctacagc 1080
tcctgggcaa cgtgctggtt attgtgctgt ctcatcattt tggcaaagaa ttggatcctt 1140
aattaagcta gcctcgaggt cgacgtatcg ataccttaag ccaccatgga ctacaaggac 1200
gacgatgaca aggctagatt agataaaagt aaagtgatta acagcgcatt agagctgctt 1260
aatgaggtcg gaatcgaagg tttaacaacc cgtaaactcg cccagaagct aggtgtagag 1320
cagcctacat tgtattggca tgtaaaaaat aagcgggctt tgctcgacgc cttagccatt 1380

```
gagatgttag ataggcacca tactcacttt tgccctttag aaggggaaag ctggcaagat   1440
tttttacgta ataacgctaa aagttttaga tgtgctttac taagtcatcg cgatggagca   1500
aaagtacatt taggtacacg gcctacagaa aaacagtatg aaactctcga aaatcaatta   1560
gcctttttat gccaacaagg tttttcacta gagaatgcat tatatgcact cagcgctgtg   1620
gggcatttta ctttaggttg cgtattggaa gatcaagagc atcaagtcgc taaagaagaa   1680
agggaaacac ctactactga tagtatgccg ccattattac gacaagctat cgaattattt   1740
gatcaccaag gtgcagagcc agccttctta ttcggccttg aattgatcac atgcggatta   1800
gaaaaacaac ttaaatgtga aagtgggtcg ccaaaaaaga agcatatgga attcaatggg   1860
gcaataggag gtgatctgtt gctcaacttt cccgacatga gcgtgctcga aaggcaacgc   1920
gcacatctga agtacctgaa tcccaccttt gacagtccat tggcaggctt cttcgccgac   1980
agcagcatga tcacaggagg cgagatggac agttatctga gcactgctgg gctcaacttg   2040
cccatgatgt acggtgaaac aactgtcgag ggtgattcca ggctttccat ctcaccggaa   2100
acgacccttg gaactggcaa ttttaaggct gcgaagtttg acaccgagac taaagattgc   2160
aacgaggcag ccaagaagat gaccatgaat cgggacgatc tggtggaaga aggggaagag   2220
gagaaatcca agattaccga acagaacaat ggcagtacca agtcaatcaa gaagatgaag   2280
cacaaagcca agaaggaaga aaacaacttc agcaatgact ctagcaaagt gacaaaaagag   2340
ctggagaaaa cggactacat cacgcgtgag ggcagaggaa gtctgctaac atgcggtgac   2400
gtcgaggaga atcctggccc agccacaacc actagtgtga gcaagggcga ggaggataac   2460
atggccatca tcaaggagtt catgcgcttc aaggtgcaca tggagggctc cgtgaacggc   2520
cacgagttcg agatcgaggg cgagggcgag ggccgcccct acgagggcac ccagaccgcc   2580
aagctgaagg tgaccaaggg tggcccccctg cccttcgcct gggacatcct gtcccctcag   2640
ttcatgtacg gctccaaggc ctacgtgaag caccccgccg acatccccga ctacttgaag   2700
ctgtccttcc ccgagggctt caagtgggag cgcgtgatga acttcgagga cggcggcgtg   2760
gtgaccgtga cccaggactc ctccctgcag gacggcgagt tcatctacaa ggtgaagctg   2820
cgcggcacca acttcccctc cgacggcccc gtaatgcaga agaagaccat gggctgggag   2880
gcctcctccg agcggatgta ccccgaggac ggcgccctga agggcgagat caagcagagg   2940
ctgaagctga aggacggcgg ccactacgac gctgaggtca agaccaccta caaggccaag   3000
aagcccgtgc agctgcccgg cgcctacaac gtcaacatca agttggacat cacctcccac   3060
aacgaggact acaccatcgt ggaacagtac gaacgcgccg agggccgcca ctccaccggc   3120
ggcatggacg agctgtacaa gcctccaaaa aagaagagaa aggtagtacc tccaaaaaag   3180
aagagaaagg tagtctaggc ggccgaaagc ttgataagta atgtcgagga ccgcggtggc   3240
gcgcctgata tcagcggccg ccaccgcggt ggagctccga attcgatatc aagcttatcg   3300
ataatcaacc tctggattac aaaatttgtg aaagattgac tggtattctt aactatgttg   3360
ctccttttac gctatgtgga tacgctgctt taatgccttt gtatcatgct attgcttccc   3420
gtatggcttt cattttctcc tccttgtata aatcctggtt gctgtctctt tatgaggagt   3480
tgtggcccgt tgtcaggcaa cgtggcgtgg tgtgcactgt gtttgctgac gcaaccccca   3540
ctggttgggg cattgccacc acctgtcagc tcctttccgg gactttcgct ttccccctcc   3600
ctattgccac ggcggaactc atcgccgcct gccttgcccg ctgctggaca ggggctcggc   3660
tgttgggcac tgacaattcc gtggtgttgt cggggaaatc atcgtccttt ccttggctgc   3720
```

```
tcgcctgtgt tgccacctgg attctgcgcg ggacgtcctt ctgctacgtc ccttcggccc   3780

tcaatccagc ggaccttcct tcccgcggcc tgctgccggc tctgcggcct cttccgcgtc   3840

ttcgccttcg ccctcagacg agtcggatct ccctttgggc cgcctccccg catcgatacc   3900

gtcgacccgg gcggccgctt cgagcagaca tgataagata cattgatgag tttggacaaa   3960

ccacaactag aatgcagtga aaaaaatgct ttatttgtga aatttgtgat gctattgctt   4020

tatttgtaac cattataagc tgcaataaac aagttaacaa caacaattgc attcatttta   4080

tgtttcaggt tcagggggag atgtgggagg ttttttaaag caagtaaaac ctctacaaat   4140

gtggtaaaat cgataaggat cttcctagag catggctacg tagataagta gcatggcggg   4200

ttaatcatta actacaagga acccctagtg atggagttgg ccactccctc tctgcgcgct   4260

cgctcgctca ctgaggccgg gcgaccaaag gtcgcccgac gcccgggctt tgcccgggcg   4320

gcctcagtga gcgagcgagc gcgcagctgc                                    4350


<210> SEQ ID NO 19
<211> LENGTH: 4578
<212> TYPE: DNA
<213> ORGANISM: Artificial Sequence
<220> FEATURE:
<223> OTHER INFORMATION: CAG-NLS-attached Cry2 PHR(L348F)-p65AD N
      terminal fusion construct (Virus 2)
<220> FEATURE:
<222> LOCATION: (1)..(133)
<223> OTHER INFORMATION: ITR
<220> FEATURE:
<221> NAME/KEY: promoter
<222> LOCATION: (196)..(1132)
<223> OTHER INFORMATION: pCAG
<220> FEATURE:
<222> LOCATION: (1164)..(1166)
<223> OTHER INFORMATION: initiation codon
<220> FEATURE:
<221> NAME/KEY: CDS
<222> LOCATION: (1167)..(2651)
<223> OTHER INFORMATION: Human optimized Cry2 PHR L348F -ATG-stop
<220> FEATURE:
<221> NAME/KEY: mat_peptide
<222> LOCATION: (2664)..(3464)
<223> OTHER INFORMATION: Human p65 AD
<220> FEATURE:
<221> NAME/KEY: sig_peptide
<222> LOCATION: (3465)..(3488)
<223> OTHER INFORMATION: NLS
<220> FEATURE:
<221> NAME/KEY: sig_peptide
<222> LOCATION: (3492)..(3515)
<223> OTHER INFORMATION: NLS
<220> FEATURE:
<222> LOCATION: (3516)..(3518)
<223> OTHER INFORMATION: STOP codon
<220> FEATURE:
<222> LOCATION: (3525)..(4129)
<223> OTHER INFORMATION: WPRE
<220> FEATURE:
<221> NAME/KEY: polyA_site
<222> LOCATION: (4159)..(4278)
<223> OTHER INFORMATION: SV40 early pA
<220> FEATURE:
<222> LOCATION: (4445)..(4578)
<223> OTHER INFORMATION: ITR

<400> SEQUENCE: 19

cagctgcgcg ctcgctcgct cactgaggcc gcccgggcaa agcccgggcg tcgggcgacc     60

tttggtcgcc cggcctcagt gagcgagcga gcgcgcagag agggagtggc caactccatc    120

actaggggtt ccttgtagtt aatgattaac ccgccatgct acttatctac gtagccatgc    180

tctaggaaga tcgtaccatt gacgtcaata atgacgtatg ttcccatagt aacgccaata    240
```

-continued gggactttcc attgacgtca atgggtggag tatttacggt aaactgccca cttggcagta 300
catcaagtgt atcatatgcc aagtacgccc cctattgacg tcaatgacgg taaatggccc 360
gcctggcatt atgcccagta catgacctta tgggactttc ctacttggca gtacatctac 420
gtattagtca tcgctattac catggtcgag gtgagcccca cgttctgctt cactctcccc 480
atctcccccc cctccccacc cccaattttg tatttattta tttttaatt attttgtgca 540 gcgatggggg cggggggggg gggggggcgc gcgccaggcg gggcggggcg gggcgagggg 600
cggggcgggg cgaggcggag aggtgcggcg gcagccaatc agagcggcgc gctccgaaag 660
tttcctttta tggcgaggcg gcggcggcgg cggccctata aaaagcgaag cgcgcggcgg 720
gcgggagtcg ctgcgacgct gccttcgccc cgtgccccgc tccgccgccg cctcgcgccg 780
cccgccccgg ctctgactga ccgcgttact cccacaggtg agcgggcggg acggcccttc 840
tcctccgggc tgtaattagc gcttggttta atgacggctt gtttcttttc tgtggctgcg 900
tgaaagcctt gaggggctcc gggagggccc tttgtgcggg gggagcggct cggggctgtc 960
cgcgggggga cggctgcctt cgggggggac ggggcagggc ggggttcggc ttctggcgtg 1020
tgaccggcgg ctctagagcc tctgctaacc atgttcatgc cttcttcttt ttcctacagc 1080
tcctgggcaa cgtgctggtt attgtgctgt ctcatcattt tggcaaagaa ttggatcctt 1140
aattaagcta gcctcgaccc accatgaaaa tggacaagaa aaccatcgtg tggttcagga 1200
gggatctgag aatcgaggat aatcccgccc tcgccgcagc tgctcacgaa gggagtgtgt 1260
ttccggtgtt catttggtgt ccagaggaag aggggcagtt ctaccctgga cgagcaagtc 1320
gctggtggat gaaacagtcc ctggcccatc tgtctcagag cctcaaggcc cttggctctg 1380
atctcaccct gatcaagacg cataatacaa tctccgcaat tctcgattgc attcgcgtca 1440
caggtgcgac gaaagtggtt ttcaaccacc tgtatgatcc agtttcactg gtccgtgatc 1500
acaccgtgaa agagaaactg gtagagagag gcattagtgt gcagagctac aacggggatc 1560
tgctgtacga accctgggag atttactgcg aaaagggtaa gccatttact agcttcaatt 1620
cctattggaa gaaatgtctg gacatgtcaa tcgagagcgt gatgctgcct ccaccatggc 1680
gactcatgcc cataactgct gctgctgaag cgatttgggc ctgctccatt gaggagttgg 1740
gccttgagaa tgaggcggag aagcccagta atgctctgct gaccagggca tggagtccag 1800
gatggtcaaa tgccgacaaa ctcctgaatg agttcataga gaaacagctg attgactatg 1860
ccaagaactc caagaaggtt gtgggtaact caacctctct tctcagcccc tatctgcact 1920
ttggggagat aagcgtccgg catgtgttcc agtgtgcgcg gatgaagcag atcatttggg 1980
cgagggataa gaacagcgag ggagaggaat ccgcagactt gttcctgcgg ggcatcgggc 2040
tccgcgaata tagccggtat atctgcttta acttcccttt tactcacgag cagagccttc 2100
tgagccatct gcgcttcttt ccttgggatg cagacgtgga caaatttaag gcttggcgtc 2160
aaggtaggac cggctatcca ctggtcgatg ccggcatgag agaattttgg gccactgggt 2220
ggatgcacaa ccggattagg gtgatcgtat cttcctttgc cgtcaagttt ctgttgttgc 2280
cctggaaatg ggcatgaag tacttttggg ataccctgtt ggacgccgat ctggaatgcg 2340
acatccttgg ttggcaatac ataagtggct caatacccga cggccatgag ctggatagac 2400
ttgacaatcc ggctctgcaa ggggctaagt acgaccccga aggagaatac atcagacagt 2460
ggctccccga attggccaga ctccccacag agtggattca ccacccttgg gacgcacctc 2520
tgacagttct caaagccagc ggagtagaac tgggcactaa ctacgccaag ccgatagtgg 2580

```
acattgacac agctcgggaa ctgttggcca aagcaatctc tcgcacacga gaagcccaga   2640

tcatgatcgg aactagtacg cgtgagttcc agtacctgcc cgacaccgac gaccggcacc   2700

ggatcgagga aaagcggaag cggacctacg agacattcaa gagcattatg aagaagtccc   2760

ccttcagcgg ccccaccgac cccagacccc cacctagaag aatcgccgtg cccagcagat   2820

ccagcgccag cgtgccaaag cctgcccccc agccctaccc cttcaccagc agcctgagca   2880

ccatcaacta cgatgagttc cccacaatgg tgttccccag cggccagatt tctcaggcct   2940

ctgctctggc cccagcccct ccacaggtgc tgccacaggc ccctgctcca gctcctgccc   3000

ctgctatggt gtctgccctg gcccaggctc cagctcctgt gcctgtgctg gctcctggac   3060

ctccacaggc cgtggcccct ccagccccaa aacctacaca ggccggcgag ggcacactga   3120

gcgaagccct gctccagctc cagttcgacg acgaggatct gggcgccctg ctgggcaaca   3180

gcaccgaccc tgccgtgttc accgacctgg ccagcgtgga caacagcgag ttccagcagc   3240

tcctgaacca gggcatcccc gtggctccac acaccaccga gcccatgctg atggaatacc   3300

ccgaggccat cacccggctg gtcacaggcg ctcagaggcc tcctgatcct gccccagctc   3360

cactgggagc ccctggcctg cctaatggcc tgctgagcgg cgacgaggac ttcagctcta   3420

tcgccgacat ggacttctcc gccctgctgt cccagatcag cagccctcca aaaaagaaga   3480

gaaaggtagt acctccaaaa aagaagagaa aggtataaaa gcttatcgat aatcaacctc   3540

tggattacaa aatttgtgaa agattgactg gtattcttaa ctatgttgct ccttttacgc   3600

tatgtggata cgctgcttta atgcctttgt atcatgctat tgcttcccgt atggctttca   3660

ttttctcctc cttgtataaa tcctggttgc tgtctcttta tgaggagttg tggcccgttg   3720

tcaggcaacg tggcgtggtg tgcactgtgt ttgctgacgc aacccccact ggttggggca   3780

ttgccaccac ctgtcagctc ctttccggga ctttcgcttt ccccctccct attgccacgg   3840

cggaactcat cgccgcctgc cttgcccgct gctggacagg ggctcggctg ttgggcactg   3900

acaattccgt ggtgttgtcg gggaaatcat cgtcctttcc ttggctgctc gcctgtgttg   3960

ccacctggat tctgcgcggg acgtccttct gctacgtccc ttcggccctc aatccagcgg   4020

accttccttc ccgcggcctg ctgccggctc tgcggcctct tccgcgtctt cgccttcgcc   4080

ctcagacgag tcggatctcc ctttgggccg cctccccgca tcgataccgt cgacccgggc   4140

ggccgcttcg agcagacatg ataagataca ttgatgagtt tggacaaacc acaactagaa   4200

tgcagtgaaa aaaatgcttt atttgtgaaa tttgtgatgc tattgcttta tttgtaacca   4260

ttataagctg caataaacaa gttaacaaca acaattgcat tcattttatg tttcaggttc   4320

agggggagat gtgggaggtt ttttaaagca agtaaaacct ctacaaatgt ggtaaaatcg   4380

ataaggatct tcctagagca tggctacgta gataagtagc atggcgggtt aatcattaac   4440

tacaaggaac ccctagtgat ggagttggcc actccctctc tgcgcgctcg ctcgctcact   4500

gaggccgggc gaccaaaggt cgcccgacgc ccgggctttg cccgggcggc ctcagtgagc   4560

gagcgagcgc gcagctgc                                                 4578
```

<210> SEQ ID NO 20
<211> LENGTH: 2977
<212> TYPE: DNA
<213> ORGANISM: Artificial Sequence
<220> FEATURE:
<223> OTHER INFORMATION: TRE3G-Ub-NLS-luc2-Hes1 3?f UTR reporter (Virus 3)
<220> FEATURE:
<222> LOCATION: (1)..(141)
<223> OTHER INFORMATION: ITR
<220> FEATURE:
<222> LOCATION: (191)..(558)
<223> OTHER INFORMATION: TRE3Gs
<220> FEATURE:
<221> NAME/KEY: CDS
<222> LOCATION: (569)..(2221)
<223> OTHER INFORMATION: luc2
<220> FEATURE:
<221> NAME/KEY: 3'UTR
<222> LOCATION: (2227)..(2758)
<223> OTHER INFORMATION: Hes1 3'UTR
<220> FEATURE:
<222> LOCATION: (2837)..(2977)
<223> OTHER INFORMATION: ITR

<400> SEQUENCE: 20

```
cctgcaggca gctgcgcgct cgctcgctca ctgaggccgc ccgggcaaag cccgggcgtc      60

gggcgacctt tggtcgcccg gcctcagtga gcgagcgagc gcgcagagag ggagtggcca     120

actccatcac taggggttcc ttgtagttaa tgattaaccc gccatgctac ttatctacat     180

cgcggccgcc gagtttactc cctatcagtg atagagaacg tatgaagagt ttactcccta     240

tcagtgatag agaacgtatg cagactttac tccctatcag tgatagagaa cgtataagga     300

gtttactccc tatcagtgat agagaacgta tgaccagttt actccctatc agtgatagag     360

aacgtatcta cagtttactc cctatcagtg atagagaacg tatatccagt ttactcccta     420

tcagtgatag agaacgtata agctttgctt atgtaaacca gggcgcctat aaaagagtgc     480

tgatttttttg agtaaacttc aattccacaa cacttttgtc ttataccaac tttccgtacc     540

acttcctacc ctcgtaaagc tagccaccat ggaagatgcc aaaaacatta agaagggccc     600

agcgccattc tacccactcg aagacgggac cgccggcgag cagctgcaca aagccatgaa     660

gcgctacgcc ctggtgcccg gcaccatcgc ctttaccgac gcacatatcg aggtggacat     720

tacctacgcc gagtacttcg agatgagcgt tcggctggca gaagctatga agcgctatgg     780

gctgaataca aaccatcgga tcgtggtgtg cagcgagaat agcttgcagt tcttcatgcc     840

cgtgttgggt gccctgttca tcggtgtggc tgtggcccca gctaacgaca tctacaacga     900

gcgcgagctg ctgaacagca tgggcatcag ccagcccacc gtcgtattcg tgagcaagaa     960

agggctgcaa aagatcctca acgtgcaaaa gaagctaccg atcatacaaa agatcatcat    1020

catggatagc aagaccgact accagggctt ccaaagcatg tacaccttcg tgacttccca    1080

tttgccaccc ggcttcaacg agtacgactt cgtgcccgag agcttcgacc gggacaaaac    1140

catcgccctg atcatgaaca gtagtggcag taccggattg cccaagggcg tagccctacc    1200

gcaccgcacc gcttgtgtcc gattcagtca tgcccgcgac cccatcttcg gcaaccagat    1260

catccccgac accgctatcc tcagcgtggt gccatttcac cacggcttcg gcatgttcac    1320

cacgctgggc tacttgatct gcggctttcg ggtcgtgctc atgtaccgct tcgaggagga    1380

gctattcttg cgcagcttgc aagactataa gattcaatct gccctgctgg tgcccacact    1440

atttagcttc ttcgctaaga gcactctcat cgacaagtac gacctaagca acttgcacga    1500

gatcgccagc ggcggggcgc cgctcagcaa ggaggtaggt gaggccgtgg ccaaacgctt    1560

ccacctacca ggcatccgcc agggctacgg cctgacagaa acaaccagcg ccattctgat    1620

cacccccgaa ggggacgaca agcctggcgc agtaggcaag gtggtgccct tcttcgaggc    1680

taaggtggtg gacttggaca ccggtaagac actgggtgtg aaccagcgcg gcgagctgtg    1740

cgtccgtggc cccatgatca tgagcggcta cgttaacaac cccgaggcta caaacgctct    1800

catcgacaag gacggctggc tgcacagcgg cgacatcgcc tactgggacg aggacgagca    1860
```

```
cttcttcatc gtggaccggc tgaagagcct gatcaaatac aagggctacc aggtagcccc   1920

agccgaactg gagagcatcc tgctgcaaca ccccaacatc ttcgacgccg ggtcgccgg    1980

cctgcccgac gacgatgccg gcgagctgcc cgccgcagtc gtcgtgctgg aacacggtaa   2040

aaccatgacc gagaaggaga tcgtggacta tgtggccagc caggttacaa ccgccaagaa   2100

gctgcgcggt ggtgttgtgt tcgtggacga ggtgcctaaa ggactgaccg gcaagttgga   2160

cgcccgcaag atccgcgaga ttctcattaa ggccaagaag ggcggcaaga tcgccgtgta   2220

aacgcgtcct caggccactg ctacccgtaa agtccctagc ccacctctct cttctgacgg   2280

acactaaaaa cgaacttgga ttttaggaga gacttttata atttggtggt tattttgttg   2340

cttttttttaa ttctaaaaag ttactttttg tagagagctg tattaagtga ctgaccatgc   2400

actgcatttg tatatatttt atatgttcat attggattgc gcctttgtat tataaaagtt   2460

gagatgacat ttcgtttttt acacgagatt tctttttttta tgtgatgcca aagatgtttg   2520

aaaatgctct taaaatatct tcctttgggg aagtttattt gagaaaatat aataaaagag   2580

tgaaggcttt tatgtcttag aactgattat ttcaaaattt gtaaaaaaaa aaaagtggtg   2640

gggcttgaaa ttcatgtagt ttggcaattc agaaatagga tgtatttttt aaagttttaa   2700

acaggaacca tcaaaccttt cagcaacact caatgatcta agaagaccta atttatgaga   2760

attcgtttcg aagcgtcgac tctccggatt aattaagatg tagataagta gcatggcggg   2820

ttaatcatta actacaagga acccctagtg atggagttgg ccactccctc tctgcgcgct   2880

cgctcgctca ctgaggccgc ccgggcaaag cccgggcgtc gggcgacctt tggtcgcccg   2940

gcctcagtga gcgagcgagc gcgcagctgc ctgcagg                            2977
```

<210> SEQ ID NO 21
<211> LENGTH: 731
<212> TYPE: PRT
<213> ORGANISM: Rhodopseudomonas palustris
<220> FEATURE:
<223> OTHER INFORMATION: RpBphP1

<400> SEQUENCE: 21

```
Met Val Ala Gly His Ala Ser Gly Ser Pro Ala Phe Gly Thr Ala Asp
1               5                   10                  15

Leu Ser Asn Cys Glu Arg Glu Glu Ile His Leu Ala Gly Ser Ile Gln
            20                  25                  30

Pro His Gly Ala Leu Leu Val Val Ser Glu Pro Asp His Arg Ile Ile
        35                  40                  45

Gln Ala Ser Ala Asn Ala Ala Glu Phe Leu Asn Leu Gly Ser Val Leu
    50                  55                  60

Gly Val Pro Leu Ala Glu Ile Asp Gly Asp Leu Leu Ile Lys Ile Leu
65                  70                  75                  80

Pro His Leu Asp Pro Thr Ala Glu Gly Met Pro Val Ala Val Arg Cys
                85                  90                  95

Arg Ile Gly Asn Pro Ser Thr Glu Tyr Asp Gly Leu Met His Arg Pro
            100                 105                 110

Pro Glu Gly Gly Leu Ile Ile Glu Leu Glu Arg Ala Gly Pro Pro Ile
        115                 120                 125

Asp Leu Ser Gly Thr Leu Ala Pro Ala Leu Glu Arg Ile Arg Thr Ala
    130                 135                 140

Gly Ser Leu Arg Ala Leu Cys Asp Asp Thr Ala Leu Leu Phe Gln Gln
145                 150                 155                 160

Cys Thr Gly Tyr Asp Arg Val Met Val Tyr Arg Phe Asp Glu Gln Gly
```

```
                165                 170                 175

His Gly Glu Val Phe Ser Glu Arg His Val Pro Gly Leu Glu Ser Tyr
            180                 185                 190

Phe Gly Asn Arg Tyr Pro Ser Ser Asp Ile Pro Gln Met Ala Arg Arg
        195                 200                 205

Leu Tyr Glu Arg Gln Arg Val Arg Val Leu Val Asp Val Ser Tyr Gln
    210                 215                 220

Pro Val Pro Leu Glu Pro Arg Leu Ser Pro Leu Thr Gly Arg Asp Leu
225                 230                 235                 240

Asp Met Ser Gly Cys Phe Leu Arg Ser Met Ser Pro Ile His Leu Gln
                245                 250                 255

Tyr Leu Lys Asn Met Gly Val Arg Ala Thr Leu Val Val Ser Leu Val
            260                 265                 270

Val Gly Gly Lys Leu Trp Gly Leu Val Ala Cys His His Tyr Leu Pro
        275                 280                 285

Arg Phe Ile His Phe Glu Leu Arg Ala Ile Cys Glu Leu Leu Ala Glu
    290                 295                 300

Ala Ile Ala Thr Arg Ile Thr Ala Leu Glu Ser Phe Ala Gln Ser Gln
305                 310                 315                 320

Ser Glu Leu Phe Val Gln Arg Leu Glu Gln Arg Met Ile Glu Ala Ile
                325                 330                 335

Thr Arg Glu Gly Asp Trp Arg Ala Ala Ile Phe Asp Thr Ser Gln Ser
            340                 345                 350

Ile Leu Gln Pro Leu His Ala Asp Gly Cys Ala Leu Val Tyr Glu Asp
        355                 360                 365

Gln Ile Arg Thr Ile Gly Asp Val Pro Ser Thr Gln Asp Val Arg Glu
    370                 375                 380

Ile Ala Gly Trp Leu Asp Arg Gln Pro Arg Ala Ala Val Thr Ser Thr
385                 390                 395                 400

Ala Ser Leu Gly Leu Asp Val Pro Glu Leu Ala His Leu Thr Arg Met
                405                 410                 415

Ala Ser Gly Val Val Ala Ala Pro Ile Ser Asp His Arg Gly Glu Phe
            420                 425                 430

Leu Met Trp Phe Arg Pro Glu Arg Val His Thr Val Thr Trp Gly Gly
        435                 440                 445

Asp Pro Lys Lys Pro Phe Thr Met Gly Asp Thr Pro Ala Asp Leu Ser
    450                 455                 460

Pro Arg Arg Ser Phe Ala Lys Trp His Gln Val Val Glu Gly Thr Ser
465                 470                 475                 480

Asp Pro Trp Thr Ala Ala Asp Leu Ala Ala Ala Arg Thr Ile Gly Gln
                485                 490                 495

Thr Val Ala Asp Ile Val Leu Gln Phe Arg Ala Val Arg Thr Leu Ile
            500                 505                 510

Ala Arg Glu Gln Tyr Glu Gln Phe Ser Ser Gln Val His Ala Ser Met
        515                 520                 525

Gln Pro Val Leu Ile Thr Asp Ala Glu Gly Arg Ile Leu Leu Met Asn
    530                 535                 540

Asp Ser Phe Arg Asp Met Leu Pro Ala Gly Ser Pro Ser Ala Val His
545                 550                 555                 560

Leu Asp Asp Leu Ala Gly Phe Phe Val Glu Ser Asn Asp Phe Leu Arg
                565                 570                 575

Asn Val Ala Glu Leu Ile Asp His Gly Arg Gly Trp Arg Gly Glu Val
            580                 585                 590
```

```
Leu Leu Arg Gly Ala Gly Asn Arg Pro Leu Pro Leu Ala Val Arg Ala
        595                 600                 605

Asp Pro Val Thr Arg Thr Glu Asp Gln Ser Leu Gly Phe Val Leu Ile
    610                 615                 620

Phe Ser Asp Ala Thr Asp Arg Arg Thr Ala Asp Ala Ala Arg Thr Arg
625                 630                 635                 640

Phe Gln Glu Gly Ile Leu Ala Ser Ala Arg Pro Gly Val Arg Leu Asp
                645                 650                 655

Ser Lys Ser Asp Leu Leu His Glu Lys Leu Leu Ser Ala Leu Val Glu
            660                 665                 670

Asn Ala Gln Leu Ala Ala Leu Glu Ile Thr Tyr Gly Val Glu Thr Gly
        675                 680                 685

Arg Ile Ala Glu Leu Leu Glu Gly Val Arg Gln Ser Met Leu Arg Thr
    690                 695                 700

Ala Glu Val Leu Gly His Leu Val Gln His Ala Ala Arg Thr Ala Gly
705                 710                 715                 720

Ser Asp Ser Ser Ser Asn Gly Ser Gln Asn Lys
                725                 730
```

<210> SEQ ID NO 22
<211> LENGTH: 177
<212> TYPE: PRT
<213> ORGANISM: Artificial Sequence
<220> FEATURE:
<223> OTHER INFORMATION: RpQ-PAS1

<400> SEQUENCE: 22

```
Met Pro Glu Phe Gly Lys Asn Met Gln Ala Val Thr Glu Leu His Ser
1               5                   10                  15

Arg Leu Ile Ala Ala Gln Gln Ala Met Glu Arg Asp Tyr Trp Arg Leu
            20                  25                  30

Arg Glu Leu Glu Thr Arg Tyr Arg Leu Val Phe Asp Ala Ala Ala Asp
        35                  40                  45

Ala Val Met Ile Val Ser Ala Gly Asp Met Arg Ile Val Glu Ala Asn
    50                  55                  60

Arg Ala Ala Val Asn Ala Ile Ser Arg Val Glu Arg Gly Asn Asp Asp
65                  70                  75                  80

Leu Ala Gly Arg Asp Phe Leu Ala Glu Val Ala Ala Ala Asp Arg Asp
                85                  90                  95

Ala Val Arg Asp Met Leu Ala Gln Val Arg Gln Arg Gly Thr Ala Leu
            100                 105                 110

Ser Val Leu Val His Leu Gly Arg Tyr Asp Arg Ala Trp Met Leu Arg
        115                 120                 125

Gly Ser Leu Met Ser Ser Glu Arg Arg Gln Val Phe Leu Leu His Phe
    130                 135                 140

Thr Pro Val Thr Thr Thr Pro Ala Ile Asp Asp Asp Asp Lys Gly Val
145                 150                 155                 160

Val Ala Ser Ala Ala Asp Gly Ala Glu Gly Ala Ser Asp Asp Ala Glu
                165                 170                 175

Asp
```

<210> SEQ ID NO 23
<211> LENGTH: 4
<212> TYPE: PRT
<213> ORGANISM: Artificial Sequence
<220> FEATURE:

<223> OTHER INFORMATION: Linker

<400> SEQUENCE: 23

His Met Glu Phe

<210> SEQ ID NO 24
<211> LENGTH: 4
<212> TYPE: PRT
<213> ORGANISM: Artificial Sequence
<220> FEATURE:
<223> OTHER INFORMATION: Linker

<400> SEQUENCE: 24

Thr Ser Thr Arg

<210> SEQ ID NO 25
<211> LENGTH: 9
<212> TYPE: PRT
<213> ORGANISM: Artificial Sequence
<220> FEATURE:
<223> OTHER INFORMATION: Linker

<400> SEQUENCE: 25

Ser Pro Lys Lys Lys His Met Glu Phe
1               5

<210> SEQ ID NO 26
<211> LENGTH: 2838
<212> TYPE: DNA
<213> ORGANISM: Artificial Sequence
<220> FEATURE:
<223> OTHER INFORMATION: TetR(I194T,1-206)-SPKKKHMEF-codon humanized
      BphP1 -ATG+Stop fusion construct
<220> FEATURE:
<221> NAME/KEY: mat_peptide
<222> LOCATION: (1)..(618)
<223> OTHER INFORMATION: TetR(I194T,1-206)
<220> FEATURE:
<221> NAME/KEY: CDS
<222> LOCATION: (619)..(645)
<223> OTHER INFORMATION: SPKKKHMEF
<220> FEATURE:
<221> NAME/KEY: CDS
<222> LOCATION: (646)..(2835)
<223> OTHER INFORMATION: codon humanized BphP1 -ATG
<220> FEATURE:
<222> LOCATION: (2836)..(2838)
<223> OTHER INFORMATION: STOP codon

<400> SEQUENCE: 26
atggctagat tagataaaag taaagtgatt aacagcgcat tagagctgct taatgaggtc     60
ggaatcgaag gtttaacaac ccgtaaactc gcccagaagc taggtgtaga gcagcctaca    120
ttgtattggc atgtaaaaaa taagcgggct ttgctcgacg ccttagccat tgagatgtta    180
gataggcacc atactcactt ttgcccttta gaaggggaaa gctggcaaga tttttacgt     240 aataacgcta aaagttttag atgtgcttta ctaagtcatc gcgatggagc aaaagtacat    300
ttaggtacac ggcctacaga aaaacagtat gaaactctcg aaaatcaatt agcctttta     360 tgccaacaag gtttttcact agagaatgca ttatatgcac tcagcgctgt ggggcatttt    420
actttaggtt gcgtattgga agatcaagag catcaagtcg ctaaagaaga aagggaaaca    480
cctactactg atagtatgcc gccattatta cgacaagcta tcgaattatt tgatcaccaa    540
ggtgcagagc cagccttctt attcggcctt gaattgatca catgcggatt agaaaaacaa    600
cttaaatgtg aaagtgggtc gccaaaaaag aagcatatgg aattcgttgc tggtcatgct    660

```
tctggtagcc cggctttcgg gacggcggat cttagtaact gtgaacggga agaaattcat    720

cttgctggct ctattcagcc tcacggagcc ttgctggtcg tttcagagcc tgatcacagg    780

attatccagg cgtctgctaa cgccgccgag ttcctcaacc tcggatcagt gctcggggtt    840

ccccttgctg agatagacgg agacttgctc attaagatcc tccctcatct ggacccgaca    900

gccgaaggaa tgccagttgc agtgagatgt cgaataggca atccgtcaac cgagtacgac    960

gggctcatgc atcggccgcc agagggaggc ctcatcattg aacttgagag agcagggcca   1020

ccgattgatt tgtctggtac actggcgccg gcgctggagc ggataaggac cgccggatca   1080

ttgcgagctt tgtgcgacga tacggccctt ctcttccagc agtgcactgg ctacgatcgg   1140

gtaatggtat ataggttcga tgaacaagga cacggggagg tgtttagcga aaggcatgtt   1200

ccgggcctcg aatcttactt cggcaaccgc tatccaagct cagatatacc ccagatggca   1260

cggagactgt acgaaagaca gagggtgcgc gtattggtcg atgtgtccta tcagcccgtc   1320

cctttggagc ctcgactgtc tcccctgacc ggacgggacc tcgacatgag cggatgtttt   1380

ctgcggtcaa tgtcaccaat ccatcttcag tacttgaaga atatgggagt gagagccacc   1440

ctcgtcgtct ctctggtggt cggagggaag ctgtggggtc tggttgcctg ccatcactac   1500

cttccccggt tcattcactt cgaactgcgc gctatttgcg aactgcttgc tgaggccata   1560

gccacaagaa ttactgcctt ggagagtttt gctcaatccc aaagtgagct gttcgtacag   1620

aggcttgaac agcgaatgat tgaagcaatc accagagagg gcgattggcg ggcagcgata   1680

ttcgacacat cccaaagcat cctgcagcca ctgcatgccg acgggtgcgc tcttgtatat   1740

gaggatcaga ttcggacaat tggcgacgtg ccaagcacgc aggatgtaag ggaaatcgct   1800

gggtggcttg accgacaacc acgggccgct gtgacaagta ccgcaagcct gggacttgac   1860

gtcccagagc tggcgcatct gactagaatg gcatccggtg tcgtagcggc accaatttca   1920

gatcataggg gagagtttct gatgtggttc cgacctgaaa gagttcacac cgtgacgtgg   1980

ggcggcgacc cgaagaaacc cttcactatg ggagataccc cggccgacct cagtccgcga   2040

agatcattcg ctaaatggca ccaggttgtc gagggcacta gcgatccttg gactgcggca   2100

gatttggctg cggcacggac tattggacag actgtggccg atatagtact gcaattcagg   2160

gcggtcagga ccctcatagc gagagagcag tatgagcaat ttagtagtca ggttcatgcc   2220

agcatgcaac ctgtcctcat aaccgatgcc gaaggtcgca ttcttctgat gaacgactca   2280

tttcgagata tgctgcctgc aggctcacca tcagccgtcc acctcgatga tctggcaggc   2340

ttcttcgtag agtccaacga ttttctccgc aacgttgccg aactcattga tcatggccgc   2400

gggtggagag gcgaggtcct cttgcggggc gccggaaaca gacctttgcc attggcagtc   2460

cgggcagacc cagttacacg aacggaagac caaagcctgg ggtttgtcct tatattttca   2520

gatgcaacgg accgacgcac ggcggatgca gctcggacta gattccagga aggaatactg   2580

gccagcgccc gccccggggt tagactcgat tctaagtccg atctgcttca tgagaagctc   2640

ttgtctgcac tcgtcgagaa tgcgcaattg gcggctttgg aaatcactta cggggtggaa   2700

acaggcagaa tagctgaact gctggaaggc gtcagacaga gcatgttgag aacagctgag   2760

gttcttggac atctggtgca gcacgcggct cggactgcgg gtagcgattc ttcttccaat   2820

ggctcacaga ataagtga                                                 2838
```

<210> SEQ ID NO 27
<211> LENGTH: 1401
<212> TYPE: DNA
<213> ORGANISM: Artificial Sequence

```
<220> FEATURE:
<223> OTHER INFORMATION: NLSx2 p65 AD - HMEF - Q-PAS1 +Stop fusion
      construct
<220> FEATURE:
<221> NAME/KEY: sig_peptide
<222> LOCATION: (7)..(30)
<223> OTHER INFORMATION: NLS
<220> FEATURE:
<221> NAME/KEY: sig_peptide
<222> LOCATION: (34)..(57)
<223> OTHER INFORMATION: NLS
<220> FEATURE:
<221> NAME/KEY: mat_peptide
<222> LOCATION: (58)..(858)
<223> OTHER INFORMATION: Human p65 AD
<220> FEATURE:
<221> NAME/KEY: CDS
<222> LOCATION: (859)..(870)
<223> OTHER INFORMATION: HMEF
<220> FEATURE:
<221> NAME/KEY: CDS
<222> LOCATION: (871)..(1398)
<223> OTHER INFORMATION: codon humanized Q-PAS1 -ATG
<220> FEATURE:
<222> LOCATION: (1399)..(1401)
<223> OTHER INFORMATION: STOP codon

<400> SEQUENCE: 27

atggtacctc caaaaaagaa gagaaaggta gtacctccaa aaaagaagag aaaggtagag     60

ttccagtacc tgcccgacac cgacgaccgg caccggatcg aggaaaagcg gaagcggacc    120

tacgagacat tcaagagcat tatgaagaag tccccttca gcggccccac cgaccccaga    180

cccccaccta gaagaatcgc cgtgcccagc agatccagcg ccagcgtgcc aaagcctgcc    240

ccccagccct accccttcac cagcagcctg agcaccatca actacgatga gttccccaca    300

atggtgttcc ccagcggcca gatttctcag gcctctgctc tggccccagc ccctccacag    360

gtgctgccac aggcccctgc tccagctcct gcccctgcta tggtgtctgc cctggcccag    420

gctccagctc ctgtgcctgt gctggctcct ggacctccac aggccgtggc ccctccagcc    480

ccaaaaccta cacaggccgg cgagggcaca ctgagcgaag ccctgctcca gctccagttc    540

gacgacgagg atctgggcgc cctgctgggc aacagcaccg accctgccgt gttcaccgac    600

ctggccagcg tggacaacag cgagttccag cagctcctga accagggcat ccccgtggct    660

ccacacacca ccgagcccat gctgatggaa taccccgagg ccatcacccg gctggtcaca    720

ggcgctcaga ggcctcctga tcctgcccca gctccactgg gagcccctgg cctgcctaat    780

ggcctgctga gcggcgacga ggacttcagc tctatcgccg acatggactt ctccgccctg    840

ctgtcccaga tcagcagcca tatggaattc cccgagtttg gtaagaacat gcaggctgtt    900

acagagttgc actcaagatt gattgcggct caacaggcca tggaacgcga ttactggagg    960

ctgcgcgaat tggaaactcg ataccgcctg gtctttgatg cagcggctga cgcggtaatg   1020

attgtgtccg caggcgacat gaggattgtg gaagccaatc gagctgcggt taacgcgatt   1080

tccagagtgg aacggggaaa tgatgacctt gcaggaaggg attttctcgc cgaagtcgcc   1140

gctgccgaca gggacgcggt ccgggacatg cttgcccagg ttcggcagcg gggaacggcc   1200

ctgtcagtgc tggtccacct ggggagatac gaccgcgcgt ggatgctgag aggcagcctg   1260

atgtcttctg agagaagaca agtgttcctg ctgcacttca ccccagtgac cacaacacca   1320

gcaatagacg atgacgataa aggtgtggtg gccagcgcag cagacggagc cgagggcgcc   1380

agtgatgatg ccgaggattg a                                             1401

<210> SEQ ID NO 28
```

<211> LENGTH: 2838
<212> TYPE: DNA
<213> ORGANISM: Artificial Sequence
<220> FEATURE:
<223> OTHER INFORMATION: codon humanized BphP1-stop - TSTR - TetR(I194T,1-206)-ATG +Stop fusion construct
<220> FEATURE:
<221> NAME/KEY: CDS
<222> LOCATION: (1)..(2193)
<223> OTHER INFORMATION: codon humanized Q-PAS1 -ATG
<220> FEATURE:
<221> NAME/KEY: CDS
<222> LOCATION: (2194)..(2205)
<223> OTHER INFORMATION: TSTR
<220> FEATURE:
<221> NAME/KEY: mat_peptide
<222> LOCATION: (2206)..(2835)
<223> OTHER INFORMATION: TetR(I194T,1-206)
<220> FEATURE:
<222> LOCATION: (2836)..(2838)
<223> OTHER INFORMATION: STOP codon

<400> SEQUENCE: 28

```
atggttgctg gtcatgcttc tggtagcccg gctttcggga cggcggatct tagtaactgt     60

gaacgggaag aaattcatct tgctggctct attcagcctc acggagcctt gctggtcgtt    120

tcagagcctg atcacaggat tatccaggcg tctgctaacg ccgccgagtt cctcaacctc    180

ggatcagtgc tcggggttcc ccttgctgag atagacggag acttgctcat taagatcctc    240

cctcatctgg acccgacagc cgaaggaatg ccagttgcag tgagatgtcg aataggcaat    300

ccgtcaaccg agtacgacgg gctcatgcat cggccgccag agggaggcct catcattgaa    360

cttgagagag cagggccacc gattgatttg tctggtacac tggcgccggc gctggagcgg    420

ataaggaccg ccggatcatt gcgagctttg tgcgacgata cggcccttct cttccagcag    480

tgcactggct acgatcgggt aatggtatat aggttcgatg aacaaggaca cggggaggtg    540

tttagcgaaa ggcatgttcc gggcctcgaa tcttacttcg gcaaccgcta tccaagctca    600

gatatacccc agatggcacg gagactgtac gaaagacaga gggtgcgcgt attggtcgat    660

gtgtcctatc agcccgtccc tttggagcct cgactgtctc ccctgaccgg acgggacctc    720

gacatgagcg gatgttttct gcggtcaatg tcaccaatcc atcttcagta cttgaagaat    780

atgggagtga gagccaccct cgtcgtctct ctggtggtcg gagggaagct gtggggtctg    840

gttgcctgcc atcactacct tccccggttc attcacttcg aactgcgcgc tatttgcgaa    900

ctgcttgctg aggccatagc cacaagaatt actgccttgg agagttttgc tcaatcccaa    960

agtgagctgt tcgtacagag gcttgaacag cgaatgattg aagcaatcac cagagagggc   1020

gattggcggg cagcgatatt cgacacatcc caaagcatcc tgcagccact gcatgccgac   1080

gggtgcgctc ttgtatatga ggatcagatt cggacaattg gcgacgtgcc aagcacgcag   1140

gatgtaaggg aaatcgctgg gtggcttgac cgacaaccac gggccgctgt gacaagtacc   1200

gcaagcctgg gacttgacgt cccagagctg gcgcatctga ctagaatggc atccggtgtc   1260

gtagcggcac caatttcaga tcatagggga gagtttctga tgtggttccg acctgaaaga   1320

gttcacaccg tgacgtgggg cggcgacccg aagaaaccct tcactatggg agataccccg   1380

gccgacctca gtccgcgaag atcattcgct aaatggcacc aggttgtcga gggcactagc   1440

gatccttgga ctgcggcaga tttggctgcg gcacggacta ttggacagac tgtggccgat   1500

atagtactgc aattcagggc ggtcaggacc ctcatagcga gagagcagta tgagcaattt   1560

agtagtcagg ttcatgccag catgcaacct gtcctcataa ccgatgccga aggtcgcatt   1620

cttctgatga acgactcatt tcgagatatg ctgcctgcag gctcaccatc agccgtccac   1680
```

ctcgatgatc tggcaggctt cttcgtagag tccaacgatt ttctccgcaa cgttgccgaa 1740
ctcattgatc atggccgcgg gtggagaggc gaggtcctct tgcggggcgc cggaaacaga 1800
cctttgccat tggcagtccg ggcagaccca gttacacgaa cggaagacca aagcctgggg 1860
tttgtcctta tattttcaga tgcaacggac cgacgcacgg cggatgcagc tcggactaga 1920
ttccaggaag gaatactggc cagcgcccgc cccggggtta gactcgattc taagtccgat 1980
ctgcttcatg agaagctctt gtctgcactc gtcgagaatg cgcaattggc ggctttggaa 2040
atcacttacg gggtggaaac aggcagaata gctgaactgc tggaaggcgt cagacagagc 2100
atgttgagaa cagctgaggt tcttggacat ctggtgcagc acgcggctcg gactgcgggt 2160
agcgattctt cttccaatgg ctcacagaat aagactagta cgcgtgctag attagataaa 2220
agtaaagtga ttaacagcgc attagagctg cttaatgagg tcggaatcga aggtttaaca 2280
acccgtaaac tcgcccagaa gctaggtgta gagcagccta cattgtattg gcatgtaaaa 2340
aataagcggg ctttgctcga cgccttagcc attgagatgt tagataggca ccatactcac 2400
ttttgccctt tagaagggga aagctggcaa gattttttac gtaataacgc taaaagtttt 2460
agatgtgctt tactaagtca tcgcgatgga gcaaaagtac atttaggtac acggcctaca 2520
gaaaaacagt atgaaactct cgaaaatcaa ttagcctttt tatgccaaca aggtttttca 2580
ctagagaatg cattatatgc actcagcgct gtggggcatt ttactttagg ttgcgtattg 2640
gaagatcaag agcatcaagt cgctaaagaa gaaagggaaa cacctactac tgatagtatg 2700
ccgccattat tacgacaagc tatcgaatta tttgatcacc aaggtgcaga gccagccttc 2760
ttattcggcc ttgaattgat cacatgcgga ttagaaaaac aacttaaatg tgaaagtggg 2820
tcgccaaaaa agaagtaa 2838

<210> SEQ ID NO 29
<211> LENGTH: 1347
<212> TYPE: DNA
<213> ORGANISM: Artificial Sequence
<220> FEATURE:
<223> OTHER INFORMATION: p65 AD - HMEF - Q-PAS1 -ATG+Stop fusion construct
<220> FEATURE:
<221> NAME/KEY: mat_peptide
<222> LOCATION: (1)..(804)
<223> OTHER INFORMATION: Human p65 AD
<220> FEATURE:
<221> NAME/KEY: CDS
<222> LOCATION: (805)..(816)
<223> OTHER INFORMATION: HMEF
<220> FEATURE:
<221> NAME/KEY: CDS
<222> LOCATION: (817)..(1344)
<223> OTHER INFORMATION: codon humanized Q-PAS1 -ATG
<220> FEATURE:
<222> LOCATION: (1345)..(1347)
<223> OTHER INFORMATION: STOP codon

<400> SEQUENCE: 29
atggagttcc agtacctgcc cgacaccgac gaccggcacc ggatcgagga aaagcggaag 60
cggacctacg agacattcaa gagcattatg aagaagtccc ccttcagcgg ccccaccgac 120
cccagacccc cacctagaag aatcgccgtg cccagcagat ccagcgccag cgtgccaaag 180
cctgcccccc agccctaccc cttcaccagc agcctgagca ccatcaacta cgatgagttc 240
cccacaatgg tgttccccag cggccagatt tctcaggcct ctgctctggc ccccagcccct 300 ccacaggtgc tgccacaggc ccctgctcca gctcctgccc ctgctatggt gtctgccctg 360

-continued

```
gcccaggctc cagctcctgt gcctgtgctg gctcctggac ctccacaggc cgtggcccct    420

ccagccccaa aacctacaca ggccggcgag ggcacactga gcgaagccct gctccagctc    480

cagttcgacg acgaggatct gggcgccctg ctgggcaaca gcaccgaccc tgccgtgttc    540

accgacctgg ccagcgtgga caacagcgag ttccagcagc tcctgaacca gggcatcccc    600

gtggctccac acaccaccga gcccatgctg atggaatacc ccgaggccat cacccggctg    660

gtcacaggcg ctcagaggcc tcctgatcct gccccagctc cactgggagc ccctggcctg    720

cctaatggcc tgctgagcgg cgacgaggac ttcagctcta tcgccgacat ggacttctcc    780

gccctgctgt cccagatcag cagccatatg gaattccccg agtttggtaa gaacatgcag    840

gctgttacag agttgcactc aagattgatt gcggctcaac aggccatgga acgcgattac    900

tggaggctgc gcgaattgga aactcgatac cgcctggtct ttgatgcagc ggctgacgcg    960

gtaatgattg tgtccgcagg cgacatgagg attgtggaag ccaatcgagc tgcggttaac   1020

gcgatttcca gagtggaacg gggaaatgat gaccttgcag gaagggattt tctcgccgaa   1080

gtcgccgctg ccgacaggga cgcggtccgg gacatgcttg cccaggttcg gcagcgggga   1140

acggccctgt cagtgctggt ccacctgggg agatacgacc gcgcgtggat gctgagaggc   1200

agcctgatgt cttctgagag aagacaagtg ttcctgctgc acttcacccc agtgaccaca   1260

acaccagcaa tagacgatga cgataaaggt gtggtggcca gcgcagcaga cggagccgag   1320

ggcgccagtg atgatgccga ggattga                                       1347
```